(12) United States Patent
Loosararian et al.

(10) Patent No.: US 10,481,608 B2
(45) Date of Patent: Nov. 19, 2019

(54) SYSTEM, METHOD, AND APPARATUS TO PERFORM A SURFACE INSPECTION USING REAL-TIME POSITION INFORMATION

(71) Applicant: Gecko Robotics, Inc., Pittsburgh, PA (US)

(72) Inventors: Mark Loosararian, Pittsburgh, PA (US); Joshua Moore, Pittsburgh, PA (US); Yizhu Gu, Pittsburgh, PA (US); Kevin Low, Pittsburgh, PA (US); Edward Bryner, Pittsburgh, PA (US); Logan MacKenzie, Union City, PA (US); Ian Miller, Aspinwall, PA (US); Alvin Chou, Alpharetta, GA (US); Todd Joslin, Wexford, PA (US)

(73) Assignee: Gecko Robotics, Inc., Pittsburgh, PA (US)

( * ) Notice: Subject to any disclaimer, the term of this patent is extended or adjusted under 35 U.S.C. 154(b) by 0 days.

(21) Appl. No.: 15/988,975

(22) Filed: May 24, 2018

(65) Prior Publication Data
US 2018/0275671 A1    Sep. 27, 2018

Related U.S. Application Data

(63) Continuation of application No. 15/853,391, filed on Dec. 22, 2017.
(Continued)

(51) Int. Cl.
*G05D 1/02* (2006.01)
*B25J 9/16* (2006.01)
*G05D 1/00* (2006.01)

(52) U.S. Cl.
CPC .......... *G05D 1/0227* (2013.01); *B25J 9/1697* (2013.01); *G05D 1/0088* (2013.01);
(Continued)

(58) Field of Classification Search
CPC ....... G01N 29/265; G01N 29/225–226; G01N 29/28; G01N 2291/106; G01N 2291/2694;
(Continued)

(56) References Cited

U.S. PATENT DOCUMENTS 2,694,164 A    11/1954 Geppelt
3,279,242 A    10/1966 Megoloff
(Continued)

FOREIGN PATENT DOCUMENTS

FR    2861457 A1 *  4/2005    ............... B63B 9/00
FR    2970199 A1    7/2012
(Continued)

OTHER PUBLICATIONS

Curran, Make the right choice for metal coating for the right application, Design World, 2016 (Year: 2016).*
(Continued)

*Primary Examiner* — Justin Seo
*Assistant Examiner* — David L Singer
(74) *Attorney, Agent, or Firm* — GTC Law Group PC & Affiliates

(57) ABSTRACT

A system includes an inspection robot for performing an inspection on an inspection surface with ultrasonic and magnetic induction sensors, the apparatus comprising a position definition circuit structured to determine an inspection robot position on the inspection surface; a data positioning circuit structured to interpret inspection data, and to correlate the inspection data to the inspection robot position on the inspection surface; and wherein the data positioning circuit is further structured to determine position informed inspection data in response to the correlating of the inspection data with the inspection robot position.

14 Claims, 31 Drawing Sheets

Related U.S. Application Data

(60) Provisional application No. 62/596,737, filed on Dec. 8, 2017, provisional application No. 62/438,788, filed on Dec. 23, 2016.

(52) U.S. Cl.
CPC ......... *G05D 1/0246* (2013.01); *G05D 1/0272* (2013.01); *G05D 1/0274* (2013.01); *G05B 2219/45066* (2013.01)

(58) Field of Classification Search
CPC ... G01N 2291/2634; G01N 2291/2636; G01N 2291/02854; G01N 2291/0258; G01N 2291/044; G01N 2291/0231; G01N 2291/0289; B25J 5/007; B25J 9/08; B25J 19/02; B25J 19/026–027; B25J 9/1697; G05B 2219/45066; B60B 19/006; G01B 17/02–025; Y10S 901/01; Y10S 901/04; G01M 3/246; G01M 3/2823; G01M 3/005; G21C 17/002; G21C 17/003–013; G21C 17/017; G05D 1/0274; G05D 1/0088; G05D 1/0227; G05D 1/0246; G05D 1/027; G05D 1/0272; G05D 1/0268; F16L 2101/30
USPC ....... 73/622–623, 641, 633–634, 644, 865.8; 376/249
See application file for complete search history.

(56) References Cited

U.S. PATENT DOCUMENTS

| | | | |
|---|---|---|---|
| 3,420,097 A | 1/1969 | Batterman et al. | |
| 3,483,734 A | 12/1969 | Wood | |
| 3,837,202 A | 9/1974 | Hetherington et al. | |
| 4,304,134 A | 12/1981 | Rouse et al. | |
| 4,495,587 A * | 1/1985 | Plante | G01N 27/9093 324/207.25 |
| 4,526,037 A | 7/1985 | Wentzell et al. | |
| 4,537,136 A | 8/1985 | Douglas | |
| 4,706,120 A * | 11/1987 | Slaughter | G05D 1/0234 180/168 |
| 4,862,748 A | 9/1989 | Woodmansee | |
| 5,006,799 A * | 4/1991 | Pfanstiehl | G01B 7/105 324/230 |
| 5,097,710 A | 3/1992 | Palynchuk | |
| 5,440,929 A * | 8/1995 | Huang | G01B 17/02 73/628 |
| 5,549,004 A * | 8/1996 | Nugent | G01N 29/2487 376/249 |
| 5,619,423 A * | 4/1997 | Scrantz | G01N 29/2412 324/220 |
| 5,635,644 A * | 6/1997 | Ishikawa | G01B 17/025 73/614 |
| 5,929,338 A * | 7/1999 | Frankel | G01B 17/02 73/602 |
| 6,076,407 A * | 6/2000 | Levesque | G01N 29/223 324/220 |
| 6,150,809 A * | 11/2000 | Tiernan | G01N 27/82 324/225 |
| 6,220,099 B1 * | 4/2001 | Marti | G01N 29/226 73/633 |
| 6,931,931 B2 | 8/2005 | Graff et al. | |
| 9,586,636 B1 * | 3/2017 | Burmeister | B62D 57/024 |
| 2002/0143421 A1 * | 10/2002 | Wetzer | G06Q 10/06 700/100 |
| 2002/0168532 A1 * | 11/2002 | Sinsel | B32B 38/0008 428/461 |
| 2003/0089267 A1 * | 5/2003 | Ghorbel | F16L 55/26 104/138.1 |
| 2003/0172735 A1 * | 9/2003 | Lam | G01N 29/0609 73/622 |
| 2003/0188589 A1 | 10/2003 | Harthorn et al. | |
| 2004/0207394 A1 * | 10/2004 | Harthorn | G01B 17/02 324/216 |
| 2005/0150300 A1 * | 7/2005 | Nenno | G01N 29/0609 73/618 |
| 2005/0174086 A1 * | 8/2005 | Iwashita | G05B 19/4144 318/641 |
| 2005/0183506 A1 | 8/2005 | Kawabata | |
| 2005/0252296 A1 * | 11/2005 | Hock | G01N 29/041 73/623 |
| 2006/0162610 A1 * | 7/2006 | Reboredo Losada | B60B 3/048 104/138.1 |
| 2007/0006657 A1 * | 1/2007 | Kennedy | G01N 29/225 73/618 |
| 2007/0044562 A1 * | 3/2007 | Sarr | G01N 29/225 73/618 |
| 2007/0044564 A1 * | 3/2007 | Bui | G01N 29/043 73/618 |
| 2007/0227250 A1 | 10/2007 | Kennedy et al. | |
| 2008/0087112 A1 | 4/2008 | Bagley et al. | |
| 2008/0202245 A1 | 8/2008 | Young | |
| 2009/0114025 A1 * | 5/2009 | Sato | G01B 17/02 73/627 |
| 2009/0301203 A1 * | 12/2009 | Brussieux | G01N 29/225 73/627 |
| 2010/0011522 A1 | 1/2010 | Kim et al. | |
| 2010/0126403 A1 * | 5/2010 | Rooney, III | B63B 59/10 114/222 |
| 2011/0169938 A1 | 7/2011 | Webster et al. | |
| 2012/0215348 A1 * | 8/2012 | Skrinde | B08B 9/049 700/245 |
| 2013/0142297 A1 | 6/2013 | Dean et al. | |
| 2015/0153312 A1 * | 6/2015 | Gonzalez | G01D 5/00 73/23.2 |
| 2015/0226369 A1 * | 8/2015 | Troy | F16M 11/18 180/2.1 |
| 2015/0316195 A1 * | 11/2015 | Penza | F16L 55/32 405/184.1 |
| 2015/0369916 A1 | 12/2015 | Nikolov et al. | |
| 2016/0123933 A1 | 5/2016 | Fetzer et al. | |
| 2016/0238565 A1 | 8/2016 | Gonzalez et al. | |
| 2016/0282877 A1 * | 9/2016 | Gonzalez | G01B 21/22 |
| 2016/0349213 A1 * | 12/2016 | Kollgaard | G01N 29/0645 |
| 2018/0181136 A1 | 6/2018 | Loosararian et al. | |
| 2018/0267554 A1 | 9/2018 | Loosararian et al. | |
| 2018/0275670 A1 | 9/2018 | Loosararian et al. | |
| 2018/0275672 A1 | 9/2018 | Loosararian et al. | |
| 2018/0275673 A1 | 9/2018 | Loosararian et al. | |
| 2018/0275674 A1 | 9/2018 | Loosararian et al. | |
| 2018/0275675 A1 | 9/2018 | Loosararian et al. | |
| 2018/0284794 A1 | 10/2018 | Loosararian et al. | |
| 2018/0284795 A1 | 10/2018 | Loosararian et al. | |
| 2018/0284796 A1 | 10/2018 | Loosararian et al. | |
| 2018/0284797 A1 | 10/2018 | Loosararian et al. | |
| 2018/0292838 A1 | 10/2018 | Loosararian et al. | |
| 2019/0242728 A1 | 8/2019 | Low et al. | |

FOREIGN PATENT DOCUMENTS

| | | |
|---|---|---|
| JP | 61090052 | 5/1986 |
| JP | 61144503 A | 7/1986 |
| WO | 2015059916 A1 | 4/2015 |
| WO | 2016051147 A1 | 4/2016 |
| WO | 2018119450 A1 | 6/2018 |
| WO | PCT/US2019/027958 | 4/2019 |

OTHER PUBLICATIONS

All Metals Fabrication, Painting Metal, 2015 (Year: 2015).*
Berendsen, Ship Painting: Current Practice and Systems, Technology Publishing Company, PCE Sep. 1998 (Year: 1998).*
Carlsten, Understanding Corrosion and How to Protect Against It, manufacturing.net, 2002 (Year: 2002).*
PCT/US2017/068326, "International Application Serial No. PCT/US2017/068326, International Search Report and Written Opinion dated May 4, 2018", Gecko Robotics, Inc., 14 pages.

(56) References Cited

OTHER PUBLICATIONS

PCT/US2017068326, "International Application Serial No. PCT/US2017068326, Invitation to Pay Additional Fees and, Where Applicable, Protest Fee dated Feb. 27, 2018", Gecko Robotics, Inc., 2 Pages.
U.S. Appl. No. 16/387,237, filed Apr. 17, 2019, Pending.
"Coordinate Systems in Two and Three Dimensions", Oregon State University, Department of Mathematics, 2015, 3 pages.
"Horizontal definition", Merrian-Webster Dictionary, 2014, 1 page.
"Vertical Definition", Merriam Webster, 2014, 1 page.
General Electric, "BWCI Automated Boiler Wall Cleaning & Inspection", inspection-robotics.com, 2016, 4 pages.
Ginzel, et al., "Acoustic Properties of the Elastomeric Materials Aqualene and ACE", The e-Journal of Nondestructive Testing—ISSN 1435-4934, Dec. 2015, 13 pages.
NDT Resource Center, "Transducer Types", Webpage, 2005, 1 page.
Olympus, "BondMaster Probes and Accessories Catalog", Catalog, 2008, 24 pages.
Olympus, "Flaw Detectors Delay Line", Olympus, Flaw Detectors Delay Line, 2014, Jan. 9, 2014, 1 page.
Olympus, "Ultrasonic Transducers Technical Notes", Notes, 2006.
PCT/US17/68326, "International Application Serial No. PCT/US17/68326, International Preliminary Report on Patentability dated Jul. 4, 2019", Gecko Robotics, Inc., 11 pages.
Schroeder, et al., "Ultrasonic Culvert Thickness Determination", US Army Armament Research Development and Engineering, Technical Report ARCCB-TR-95027, 1995, 36 pages.
PCT/US2019/027958, "International Application Serial No. PCT/US2019/027958, International Search Report and Written Opinion dated Jul. 16, 2019", Gecko Robotics, Inc., 9 pages.

\* cited by examiner

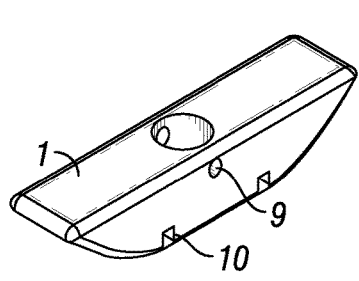 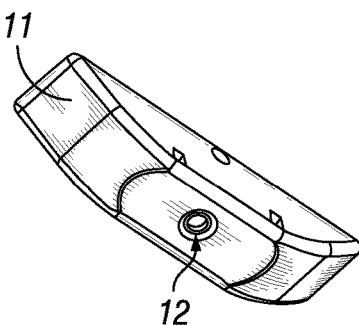 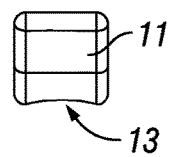
*FIG. 3A*  *FIG. 3B*  *FIG. 3C*
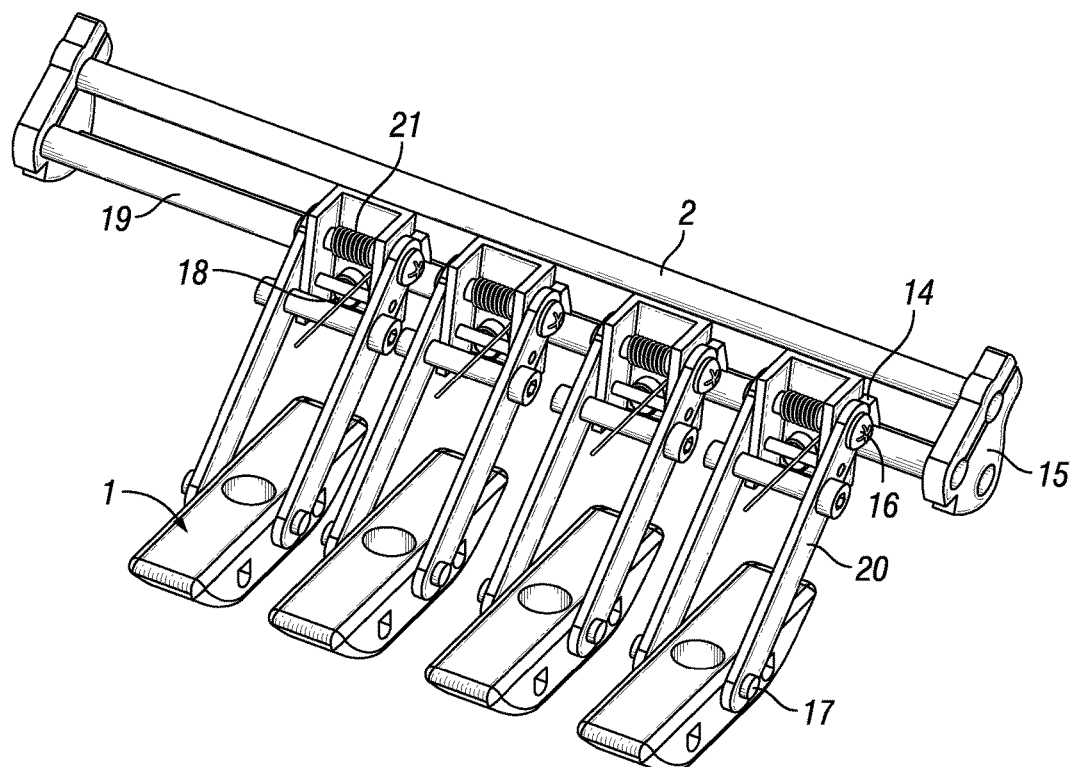
*FIG. 4*

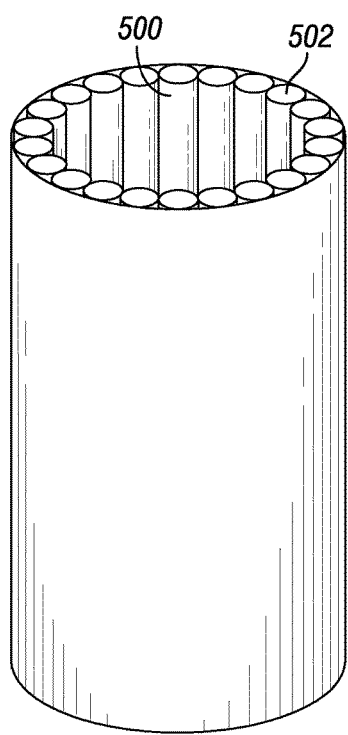 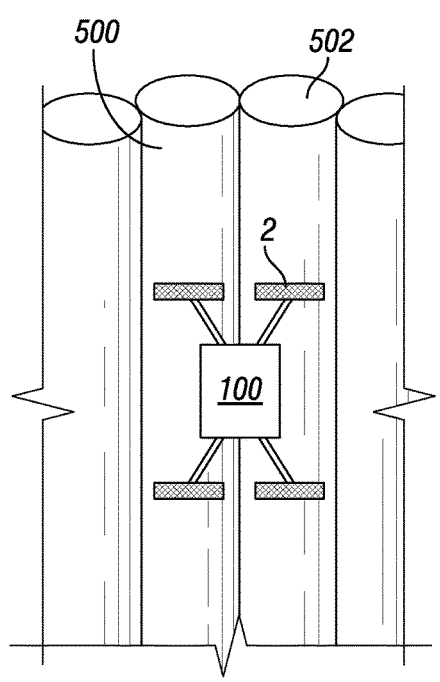
FIG. 5
FIG. 6

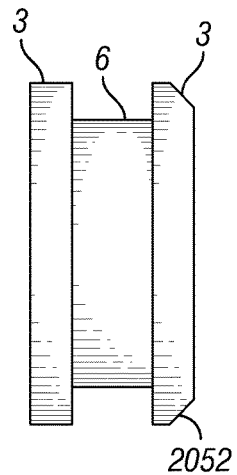
FIG. 11A
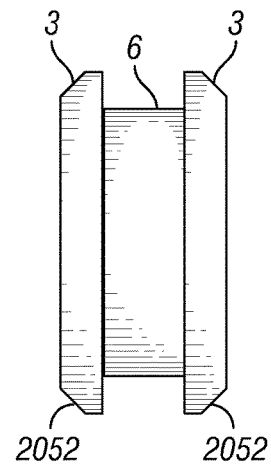
FIG. 11B
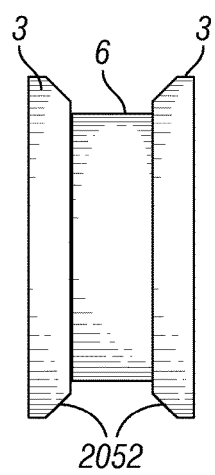
FIG. 11C
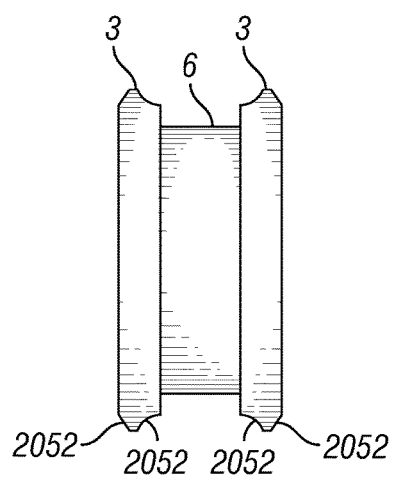
FIG. 11E
FIG. 11D

SYSTEM, METHOD, AND APPARATUS TO PERFORM A SURFACE INSPECTION USING REAL-TIME POSITION INFORMATION

CROSS-REFERENCE TO RELATED APPLICATIONS

This application claims the benefit of priority to U.S. Provisional Patent Application Ser. No. 62/596,737, filed Dec. 8, 2017, and entitled "METHOD AND APPARATUS TO INSPECT A SURFACE UTILITZING REAL-TIME POSITION INFORMATION".

This application also is a continuation of U.S. patent application Ser. No. 15/853,391, filed Dec. 22, 2017, entitled "INSPECTION ROBOT".

U.S. patent application Ser. No. 15/853,391 claims the benefit of priority to the following U.S. Provisional Patent Applications: Ser. No. 62/438,788, filed Dec. 23, 2016, and entitled "STRUCTURE TRAVERSING ROBOT WITH INSPECTION FUNCTIONALITY"; and Ser. No. 62/596, 737, filed Dec. 8, 2017, and entitled "METHOD AND APPARATUS TO INSPECT A SURFACE UTILITZING REAL-TIME POSITION INFORMATION".

Each of the foregoing applications is incorporated herein by reference in its entirety.

BACKGROUND

The present disclosure relates to robotic inspection and treatment of industrial surfaces.

SUMMARY

Previously known inspection and treatment systems for industrial surfaces suffer from a number of drawbacks. Industrial surfaces are often required to be inspected to determine whether a pipe wall, tank surface, or other industrial surface feature has suffered from corrosion, degradation, loss of a coating, damage, wall thinning or wear, or other undesirable aspects. Industrial surfaces are often present within a hazardous location—for example in an environment with heavy operating equipment, operating at high temperatures, in a confined environment, at a high elevation, in the presence of high voltage electricity, in the presence of toxic or noxious gases, in the presence of corrosive liquids, and/or in the presence of operating equipment that is dangerous to personnel. Accordingly, presently known systems require that a system be shutdown, that a system be operated at a reduced capacity, that stringent safety procedures be followed (e.g., lockout/tagout, confined space entry procedures, harnessing, etc.), and/or that personnel are exposed to hazards even if proper procedures are followed. Additionally, the inconvenience, hazards, and/or confined spaces of personnel entry into inspection areas can result in inspections that are incomplete, of low resolution, that lack systematic coverage of the inspected area, and/or that are prone to human error and judgement in determining whether an area has been properly inspected.

In embodiments, an apparatus for performing an inspection on an inspection surface with an inspection robot may comprise a position definition circuit structured to determine an inspection robot position on the inspection surface; a data positioning circuit structured to interpret inspection data, and to correlate the inspection data to the inspection robot position on the inspection surface; and wherein the data positioning circuit is further structured to determine position informed inspection data in response to the correlating of the inspection data with the inspection robot position. In embodiments, the position definition circuit may be further structured to determine the inspection robot position in response to a plant position definition. The position definition circuit may be further structured to interpret a plant shape value, and to determine the inspection robot position in response to the plant shape value. An inspection visualization circuit may be structured to determine an inspection map in response to the position informed inspection data. The inspection map may comprise a visual depiction of the inspection data positioned on a visual representation of the inspection surface. The apparatus may further provide a virtual mark positioned at a location of interest on the inspection map. The inspection visualization circuit may be further structured to interpret a user focus value, and to generate focus data in response to the user focus value. The focus data may comprise at least one value selected from the values consisting of: a date of an inspection operation, a time of an inspection operation, calibration values for sensors used in an inspection operation, a repair time for a location of the inspection surface determined in response to the user focus value, and an image of a location of the inspection surface determined in response to the user focus value.

In embodiments, a system may comprise an inspection robot having a plurality of input sensors, the plurality of input sensors distributed horizontally relative to an inspection surface and configured to provide inspection data; a controller, comprising: a position definition circuit structured to determine an inspection robot position of the inspection robot on the inspection surface; a data positioning circuit structured to interpret the inspection data, and to correlate the inspection data to the inspection robot position on the inspection surface; and wherein the data positioning circuit is further structured to determine position informed inspection data in response to the correlating of the inspection data with the inspection robot position. In embodiments, the system may further comprise, wherein at least a portion of the inspection surface comprises a ferrous substrate having a non-ferrous coating thereupon; wherein at least a portion of the plurality of input sensors comprise magnetic induction sensors, and wherein the inspection data comprises electromagnetic (EM) induction data; wherein the controller further comprises an EM data circuit structured to interpret the EM induction data, and to determine a substrate distance value in response to the EM induction data. The system may further comprise, wherein at least a second portion of the plurality of input sensors comprise ultra-sonic sensors, and wherein the inspection data further comprises ultra-sonic (UT) data; where the controller further comprises a thickness processing circuit structured to determine a thickness value in response to the UT data, wherein the thickness value comprises at least one of a thickness of the ferrous substrate, a total thickness of the ferrous substrate and the non-ferrous coating, or a thickness of the non-ferrous coating. The thickness processing circuit may be further structured to determine the thickness value in response to the substrate distance value. The system may further comprise a facility wear circuit structured to access a facility wear model, and to determine a facility wear value for the inspection surface in response to the thickness value. The inspection surface may comprise a surface at a first facility, and wherein the facility wear model includes data from an offset facility. Each of the plurality of input sensors may be positioned on one of a plurality of sleds, and wherein a plurality of the sleds are positioned on an arm operationally coupled to the inspection robot, and wherein the system further includes a biasing member providing a down force on each of the arms. The plurality of input sensors are horizontally distributed relative to the inspection surface at selected horizontal positions, wherein the selected horizontal positions comprise an inspection distance between two horizontally adjacent sensors of the plurality of input sensors that is not greater than a selected horizontal resolution.

In embodiments, a method may comprise operating an inspection robot having a plurality of horizontally distributed magnetic induction sensors; interrogating an inspection surface with the plurality of horizontally distributed magnetic induction sensors to determine electromagnetic (EM) induction data; determining a substrate distance value in response to the EM induction data. The method may further comprise providing a horizontal distribution of the distributed magnetic induction sensors to provide a selected inspection resolution of the inspection surface. The method may further comprise providing a down force to a plurality of sleds of the inspection robot, wherein each of the plurality of horizontally distributed magnetic induction sensors is mounted on one of the plurality of sleds. The inspection robot may further have a plurality of horizontally distributed ultra-sonic (UT) sensors, the method further comprising: interrogating the inspection surface with the plurality of UT sensors to determine UT data; determining a thickness value in response to the UT data and the substrate distance value, wherein the thickness value comprises at least one of a thickness of a ferrous substrate, a total thickness of the ferrous substrate and a non-ferrous coating, or a thickness of the non-ferrous coating. Determining the thickness value may comprise diagnosing a determination of the thickness value utilizing the substrate distance value. Determining the thickness value may comprise adjusting UT modes utilized to determine the thickness value in response to the substrate distance value. Each of the plurality of horizontally distributed magnetic induction sensors may be vertically aligned with a corresponding one of the plurality of horizontally aligned UT sensors, the method further comprising interrogating a selected location of the inspection surface with the magnetic induction sensors before the interrogating the selected location of the inspection surface with the UT sensors. The thickness value may comprise a thickness of the ferrous substrate, and determining a wear value in response to the thickness of the ferrous substrate. The thickness value may comprise a thickness of the non-ferrous coating, and determining a wear value in response to the thickness of the non-ferrous coating.

BRIEF DESCRIPTION OF THE FIGURES

FIGS. 3A to 3C are schematic views of a sled consistent with certain embodiments of the present disclosure.

FIG. 4 is a schematic depiction of a payload consistent with certain embodiments of the present disclosure.

FIG. 5 is a schematic depiction of an inspection surface.

FIG. 6 is a schematic depiction of an inspection robot positioned on an inspection surface.

FIGS. 11A to 11E are schematic depictions of wheels for an inspection robot.

DETAILED DESCRIPTION

Figure 1:
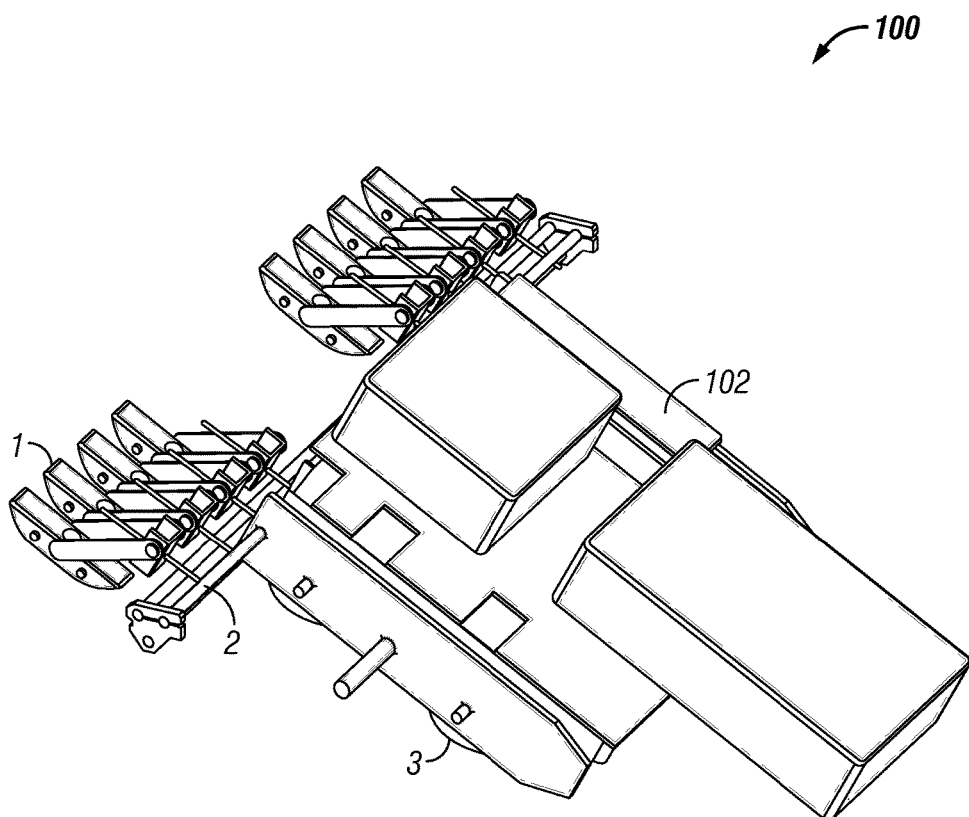
FIG. 1 is a schematic depiction of an inspection robot consistent with certain embodiments of the present disclosure.

The present disclosure relates to a system developed for traversing, climbing, or otherwise traveling over walls (curved or flat), or other industrial surfaces. Industrial surfaces, as described herein, include any tank, pipe, housing, or other surface utilized in an industrial environment, including at least heating and cooling pipes, conveyance pipes or conduits, and tanks, reactors, mixers, or containers. In certain embodiments, an industrial surface is ferromagnetic, for example including iron, steel, nickel, cobalt, and alloys thereof. In certain embodiments, an industrial surface is not ferromagnetic.

Certain descriptions herein include operations to inspect a surface, an inspection robot or inspection device, or other descriptions in the context of performing an inspection. Inspections, as utilized herein, should be understood broadly. Without limiting any other disclosures or embodiments herein, inspection operations herein include operating one or more sensors in relation to an inspected surface, electromagnetic radiation inspection of a surface (e.g., operating a camera) whether in the visible spectrum or otherwise (e.g., infrared, UV, X-Ray, gamma ray, etc.), high-resolution inspection of the surface itself (e.g., a laser profiler, caliper, etc.), performing a repair operation on a surface, performing a cleaning operation on a surface, and/or marking a surface for a later operation (e.g., for further inspection, for repair, and/or for later analysis). Inspection operations include operations for a payload carrying a sensor or an array of sensors (e.g. on sensor sleds) for measuring characteristics of a surface being traversed such as thickness of the surface, curvature of the surface, ultrasound (or ultra-sonic) measurements to test the integrity of the surface and/or the thickness of the material forming the surface, heat transfer, heat profile/mapping, profiles or mapping any other parameters, the presence of rust or other corrosion, surface defects or pitting, the presence of organic matter or mineral deposits on the surface, weld quality and the like. Sensors may include magnetic induction sensors, acoustic sensors, laser sensors, LIDAR, a variety of image sensors, and the like. The inspection sled may carry a sensor for measuring characteristics near the surface being traversed such as emission sensors to test for gas leaks, air quality monitoring, radioactivity, the presence of liquids, electro-magnetic interference, visual data of the surface being traversed such as uniformity, reflectance, status of coatings such as epoxy coatings, wall thickness values or patterns, wear patterns, and the like. The term inspection sled may indicate one or more tools for repairing, welding, cleaning, applying a treatment or coating the surface being treated. Treatments and coatings may include rust proofing, sealing, painting, application of a coating, and the like. Cleaning and repairing may include removing debris, sealing leaks, patching cracks, and the like. The term inspection sled, sensor sled, and sled may be used interchangeably throughout the present disclosure.

In certain embodiments, for clarity of description, a sensor is described in certain contexts throughout the present disclosure, but it is understood explicitly that one or more tools for repairing, cleaning, and/or applying a treatment or coating to the surface being treated are likewise contemplated herein wherever a sensor is referenced. In certain embodiments, where a sensor provides a detected value (e.g., inspection data or the like), a sensor rather than a tool may be contemplated, and/or a tool providing a feedback value (e.g., application pressure, application amount, nozzle open time, orientation, etc.) may be contemplated as a sensor in such contexts.

Inspections are conducted with a robotic system 100 (e.g., an inspection robot, a robotic vehicle, etc.) which may utilize sensor sleds 1 and a sled array system 2 which enables accurate, self-aligning, and self-stabilizing contact with a surface (not shown) while also overcoming physical obstacles and maneuvering at varying or constant speeds. In certain embodiments, mobile contact of the system 100 with the surface includes a magnetic wheel 3. In certain embodiments, a sled array system 2 is referenced herein as a payload 2—wherein a payload 2 is an arrangement of sleds 1 with sensor mounted thereon, and wherein, in certain embodiments, an entire payload 2 can be changed out as a unit. The utilization of payloads 2, in certain embodiments, allows for a pre-configured sensor array that provides for rapid re-configuration by swapping out the entire payload 2. In certain embodiments, sleds 1 and/or specific sensors on sleds 1, are changeable within a payload 2 to reconfigure the sensor array.

An example sensor sled 1 includes, without limitation, one or more sensors mounted thereon such that the sensor(s) is operationally couplable to an inspection surface in contact with a bottom surface of the corresponding one of the sleds. For example, the sled 1 may include a chamber or mounting structure, with a hole at the bottom of the sled 1 such that the sensor can maintain line-of-sight and/or acoustic coupling with the inspection surface. The sled 1 as described throughout the present disclosure is mounted on and/or operationally coupled to the inspection robot 100 such that the sensor maintains a specified alignment to the inspection surface 100—for example a perpendicular arrangement to the inspection surface, or any other specified angle. In certain embodiments, a sensor mounted on a sled 1 may have a line-of-sight or other detecting arrangement to the inspection surface that is not through the sled 1—for example a sensor may be mounted at a front or rear of a sled 1, mounted on top of a sled 1 (e.g., having a view of the inspection surface that is forward, behind, to a side, and/or oblique to the sled 1). It will be seen that, regardless of the sensing orientation of the sensor to the inspection surface, maintenance of the sled 1 orientation to the inspection surface will support more consistent detection of the inspection surface by the sensor, and/or sensed values (e.g., inspection data) that is more consistently comparable over the inspection surface and/or that has a meaningful position relationship compared to position information determined for the sled 1 or inspection robot 100. In certain embodiments, a sensor may be mounted on the inspection robot 100 and/or a payload 2—for example a camera mounted on the inspection robot 100.

The present disclosure allows for gathering of structural information from a physical structure. Example physical structures include industrial structures such as boilers, pipelines, tanks, ferromagnetic structures, and other structures. An example system 100 is configured for climbing the outside of tube walls.

As described in greater detail below, in certain embodiments, the disclosure provides a system that is capable of integrating input from sensors and sensing technology that may be placed on a robotic vehicle. The robotic vehicle is capable of multi-directional movement on a variety of surfaces, including flat walls, curved surfaces, ceilings, and/or floors (e.g., a tank bottom, a storage tank floor, and/or a recovery boiler floor). The ability of the robotic vehicle to operate in this way provides unique access especially to traditionally inaccessible or dangerous places, thus permitting the robotic vehicle to gather information about the structure it is climbing on.

The system 100 (e.g., an inspection robot, a robotic vehicle, and/or supporting devices such as external computing devices, couplant or fluid reservoirs and delivery systems, etc.) in FIG. 1 includes the sled 1 mounted on a payload 2 to provide for an array of sensors having selectable contact (e.g., orientation, down force, sensor spacing from the surface, etc.) with an inspected surface. The payload 2 includes mounting posts mounted to a main body 102 of the system 100. The payload 2 thereby provides a convenient mounting position for a number of sleds 1, allowing for multiple sensors to be positioned for inspection in a single traverse of the inspected surface. The number and distance of the sleds 1 on the payload 2 are readily adjustable—for example by sliding the sled mounts on the payload 2 to adjust spacing. Referencing FIG. 3, an example sled 1 has an aperture 12, for example to provide for couplant communication (e.g., an acoustically and/or optically continuous path of couplant) between the sensor mounted on the sled 1 and a surface to be inspected, to provide for line-of-sight availability between the sensor and the surface, or the like.

Referencing FIG. 4, an example system 100 includes the sled 1 held by an arm 20 that is connected to the payload 2 (e.g., a sensor array or sensor suite). An example system includes the sled 1 coupled to the arm 20 at a pivot point 17, allowing the sensor sled to rotate and/or tilt. On top of the arm 20, an example payload 2 includes a biasing member 21 (e.g., a torsion spring) with another pivot point 16, which provides for a selectable down-force of the arm 20 to the surface being inspected, and for an additional degree of freedom in sled 1 movement to ensure the sled 1 orients in a desired manner to the surface. In certain embodiments, down-force provides for at least a partial seal between the sensor sled 1 and surface to reduce or control couplant loss (e.g., where couplant loss is an amount of couplant consumed that is beyond what is required for operations), control distance between the sensor and the surface, and/or to ensure orientation of the sensor relative to the surface. Additionally or alternatively, the arm 20 can lift in the presence of an obstacle, while traversing between surfaces, or the like, and return to the desired position after the maneuver is completed. In certain embodiments, an additional pivot 18 couples the arm 20 to the payload 2, allowing for an additional rolling motion. In certain embodiments, pivots 16, 17, 18 provide for three degrees of freedom on arm 20 motion, allowing the arm 20 to be responsive to almost any obstacle or surface shape for inspection operations. In certain embodiments, various features of the system 100, including one or more pivots 16, 17, 18, co-operate to provide self-alignment of the sled 1 (and thus, the sensor mounted on the sled) to the surface. In certain embodiments, the sled 1 self-aligns to a curved surface and/or to a surface having variability in the surface shape.

In certain embodiments, the system is also able to collect information at multiple locations at once. This may be accomplished through the use of a sled array system. Modular in design, the sled array system allows for mounting sensor mounts, like the sleds, in fixed positions to ensure thorough coverage over varying contours. Furthermore, the sled array system allows for adjustment in spacing between sensors, adjustments of sled angle, and traveling over obstacles. In certain embodiments, the sled array system was designed to allow for multiplicity, allowing sensors to be added to or removed from the design, including changes in the type, quantity, and/or physical sensing arrangement of sensors. The sensor sleds that may be employed within the context of the present invention may house different sensors for diverse modalities useful for inspection of a structure. These sensor sleds are able to stabilize, align, travel over obstacles, and control, reduce, or optimize couplant delivery which allows for improved sensor feedback, reduced couplant loss, reduced post-inspection clean-up, reduced downtime due to sensor re-runs or bad data, and/or faster return to service for inspected equipment.

Figure 13:
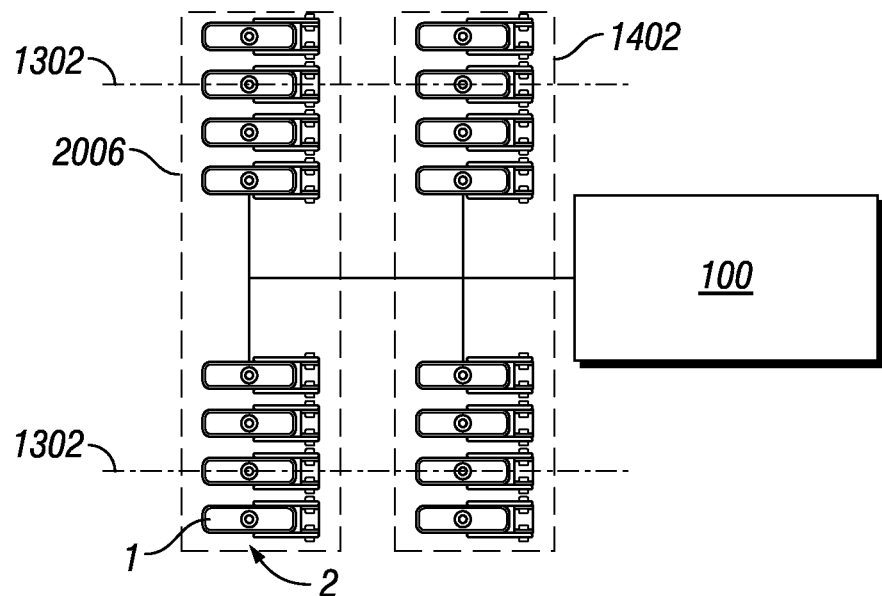
FIG. 13 is a schematic diagram of a payload arrangement.

There may be advantages to maintaining a sled with associated sensors or tools in contact and/or in a fixed orientation relative to the surface being traversed even when that surface is contoured, includes physical features, obstacles, and the like. In embodiments, there may be sled assemblies which are self-aligning to accommodate variabilities in the surface being traversed (e.g., an inspection surface) while maintaining the bottom surface of the sled (and/or a sensor or tool, e.g. where the sensor or tool protrudes through or is flush with a bottom surface of the sled) in contact with the inspection surface and the sensor or tool in a fixed orientation relative to the inspection surface. In an embodiment, as shown in FIG. 13 there may be a number of payloads 2, each payload 2 including a sled 1 positioned between a pair of sled arms 20, with each side exterior of the sled 1 attached to one end of each of the sled arms 20 at a pivot point 17 so that the sled 1 is able to rotate around an axis that would run between the pivot points 17 on each side of the sled 1. As described elsewhere herein, the payload 2 may include one or more inspection sleds 1 being pushed ahead of the payload 2, pulled behind the payload 2, or both. The other end of each sled arm 20 is attached to an inspection sled mount 14 with a pivot connection 16 which allows the sled arms to rotate around an axis running through the inspection sled mount 14 between the two pivot connections 16. Accordingly, each pair of sled arms 20 can raise or lower independently from other sled arms 20, and with the corresponding sled 1. The inspection sled mount 14 attaches to the payload 2, for example by mounting on shaft 19. The inspection sled mount 14 may connect to the payload shaft 19 with a connection 18 which allows the sled 1 and corresponding arms 20 to rotate from side to side in an arc around a perpendicular to the shaft 19. Together the up and down and side to side arc, where present, allow two degrees of rotational freedom to the sled arms. Connection 18 is illustrated as a gimbal mount in the example of FIG. 4, although any type of connection providing a rotational degree of freedom for movement is contemplated herein, as well as embodiments that do not include a rotational degree of freedom for movement. The gimbal mount 18 allows the sled 1 and associated arms 20 to rotate to accommodate side to side variability in the surface being traversed or obstacles on one side of the sled 1. The pivot points 17 between the sled arms 20 and the sled 1 allow the sled 1 to rotate (e.g., tilt in the direction of movement of the inspection robot 100) to conform to the surface being traversed and accommodate to variations or obstacles in the surface being traversed. Pivot point 17, together with the rotational freedom of the arms, provides the sled three degrees of rotational freedom relative to the inspection surface. The ability to conform to the surface being traversed facilitated the maintenance of a perpendicular interface between the sensor and the surface allowing for improved interaction between the sled 1 and the inspection surface. Improved interaction may include ensuring that the sensor is operationally couplable to the inspection surface.

Within the inspection sled mount 14 there may be a biasing member (e.g., torsion spring 21) which provides a down force to the sled 1 and corresponding arms 20. In the example, the down force is selectable by changing the torsion spring, and/or by adjusting the configuration of the torsion spring (e.g., confining or rotating the torsion spring to increase or decrease the down force). Analogous operations or structures to adjust the down force for other biasing members (e.g., a cylindrical spring, actuator for active down force control, etc.) are contemplated herein.

In certain embodiments, the inspection robot 100 includes a tether (not shown) to provide power, couplant or other fluids, and/or communication links to the robot 100. It has been demonstrated that a tether to support at least 200 vertical feet of climbing can be created, capable of couplant delivery to multiple ultra-sonic sensors, sufficient power for the robot, and sufficient communication for real-time processing at a computing device remote from the robot. Certain aspects of the disclosure herein, such as but not limited to utilizing couplant conservation features such as sled downforce configurations, the acoustic cone, and water as a couplant, support an extended length of tether. In certain embodiments, multiple ultra-sonic sensors can be provided with sufficient couplant through a ⅛" couplant delivery line, and/or through a ¼" couplant delivery line to the inspection robot 100, with ⅛" final delivery lines to individual sensors. While the inspection robot 100 is described as receiving power, couplant, and communications through a tether, any or all of these, or other aspects utilized by the inspection robot 100 (e.g., paint, marking fluid, cleaning fluid, repair solutions, etc.) may be provided through a tether or provided in situ on the inspection robot 100. For example, the inspection robot 100 may utilize batteries, a fuel cell, and/or capacitors to provide power; a couplant reservoir and/or other fluid reservoir on the robot to provide fluids utilized during inspection operations, and/or wireless communication of any type for communications, and/or store data in a memory location on the robot for utilization after an inspection operation or a portion of an inspection operation.

In certain embodiments, maintaining sleds 1 (and sensors or tools mounted thereupon) in contact and/or selectively oriented (e.g., perpendicular) to a surface being traversed provides for: reduced noise, reduced lost-data periods, fewer false positives, and/or improved quality of sensing; and/or improved efficacy of tools associated with the sled (less time to complete a repair, cleaning, or marking operation; lower utilization of associated fluids therewith; improved confidence of a successful repair, cleaning, or marking operation, etc.). In certain embodiments, maintaining sleds 1 in contacts and/or selectively oriented to the surface being traversed provides for reduced losses of couplant during inspection operations.

In certain embodiments, the combination of the pivot points 16, 17, 18) and torsion spring 21 act together to position the sled 1 perpendicular to the surface being traversed. The biasing force of the spring 21 may act to extend the sled arms 20 downward and away from the payload shaft 19 and inspection sled mount 14, pushing the sled 1 toward the inspection surface. The torsion spring 21 may be passive, applying a constant downward pressure, or the torsion spring 21 or other biasing member may be active, allowing the downward pressure to be varied. In an illustrative and non-limiting example, an active torsion spring 21 might be responsive to a command to relax the spring tension, reducing downward pressure and/or to actively pull the sled 1 up, when the sled 1 encounters an obstacle, allowing the sled 1 to more easily move over the obstacle. The active torsion spring 21 may then be responsive to a command to restore tension, increasing downward pressure, once the obstacle is cleared to maintain the close contact between the sled 1 and the surface. The use of an active spring may enable changing the angle of a sensor or tool relative to the surface being traversed during a traverse. Design considerations with respect to the surfaces being inspected may be used to design the active control system. If the spring 21 is designed to fail closed, the result would be similar to a passive spring and the sled 1 would be pushed toward the surface being inspected. If the spring 21 is designed to fail open, the result would be increased obstacle clearance capabilities. In embodiments, spring 21 may be a combination of passive and active biasing members.

The downward pressure applied by the torsion spring 21 may be supplemented by a spring within the sled 1 further pushing a sensor or tool toward the surface. The downward pressure may be supplemented by one or more magnets in/on the sled 1 pulling the sled 1 toward the surface being traversed. The one or more magnets may be passive magnets that are constantly pulling the sled 1 toward the surface being traversed, facilitating a constant distance between the sled 1 and the surface. The one or magnets may be active magnets where the magnet field strength is controlled based on sensed orientation and/or distance of the sled 1 relative to the inspection surface. In an illustrative and non-limiting example, as the sled 1 lifts up from the surface to clear an obstacle and it starts to roll, the strength of the magnet may be increased to correct the orientation of the sled 1 and draw it back toward the surface.

The connection between each sled 1 and the sled arms 20 may constitute a simple pin or other quick release connect/disconnect attachment. The quick release connection at the pivot points 17 may facilitate attaching and detaching sleds 1 enabling a user to easily change the type of inspection sled attached, swapping sensors, types of sensors, tools, and the like.

Figure 16:
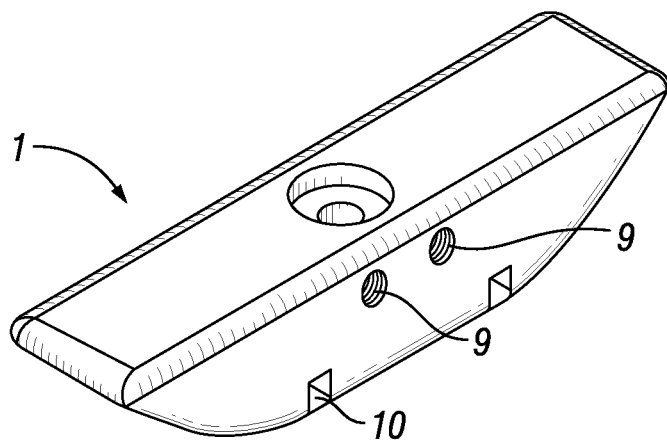
FIG. 16 is a schematic perspective view of a sled.

In embodiments, as depicted in FIG. 16, there may be multiple attachment or pivot point accommodations 9 available on the sled 1 for connecting the sled arms 20. The location of the pivot point accommodations 9 on the sled 1 may be selected to accommodate conflicting goals such as sled 1 stability and clearance of surface obstacles. Positioning the pivot point accommodations 9 behind the center of sled in the longitudinal direction of travel may facilitate clearing obstacles on the surface being traversed. Positioning the pivot point accommodation 9 forward of the center may make it more difficult for the sled 1 to invert or flip to a position where it cannot return to a proper inspection operation position. It may be desirable to alter the connection location of the sled arms 20 to the pivot point accommodations 9 (thereby defining the pivot point 17) depending on the direction of travel. The location of the pivot points 17 on the sled 1 may be selected to accommodate conflicting goals such as sensor positioning relative to the surface and avoiding excessive wear on the bottom of the sled. In certain embodiments, where multiple pivot point accommodations 9 are available, pivot point 17 selection can occur before an inspection operation, and/or be selectable during an inspection operation (e.g., arms 20 having an actuator to engage a selected one of the pivot points 9, such as extending pegs or other actuated elements, thereby selecting the pivot point 17).

Figure 17:
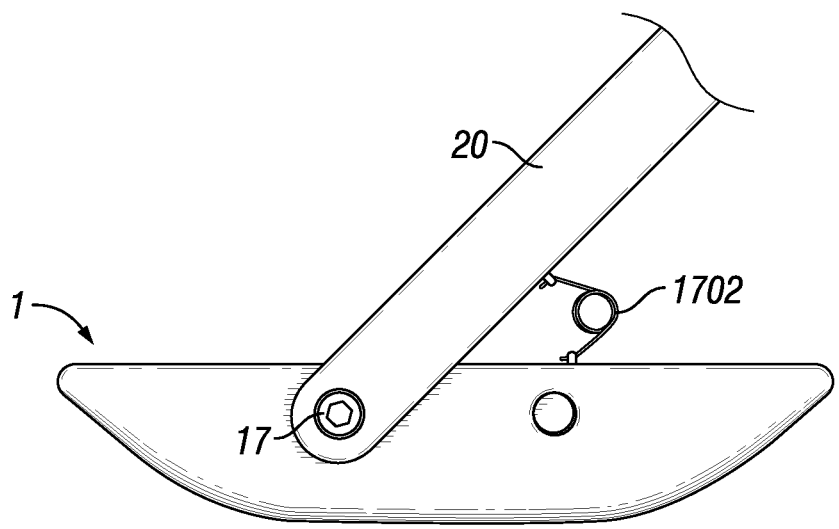
FIG. 17 is a schematic side view of a sled.

In embodiments, the degree of rotation allowed by the pivot points 17 may be adjustable. This may be done using mechanical means such as a physical pin or lock. In embodiments, as shown in FIG. 17, the connection between the sled 1 and the sled arms 20 may include a spring 1702 that biases the pivot points 17 to tend to pivot in one direction or another. The spring 1702 may be passive, with the selection of the spring based on the desired strength of the bias, and the installation of the spring 1702 may be such as to preferentially push the front or the back of the sled 1 down. In embodiments, the spring 1702 may be active and the strength and preferential pivot may be varied based on direction of travel, presence of obstacles, desired pivoting responsiveness of the sled 1 to the presence of an obstacle or variation in the inspection surface, and the like. In certain embodiments, opposing springs or biasing members may be utilized to bias the sled 1 back to a selected position (e.g., neutral/flat on the surface, tilted forward, tilted rearward, etc.). Where the sled 1 is biased in a given direction (e.g., forward or rearward), the sled 1 may nevertheless operate in a neutral position during inspection operations, for example due to the down force from the arm 20 on the sled 1.

Figure 18:
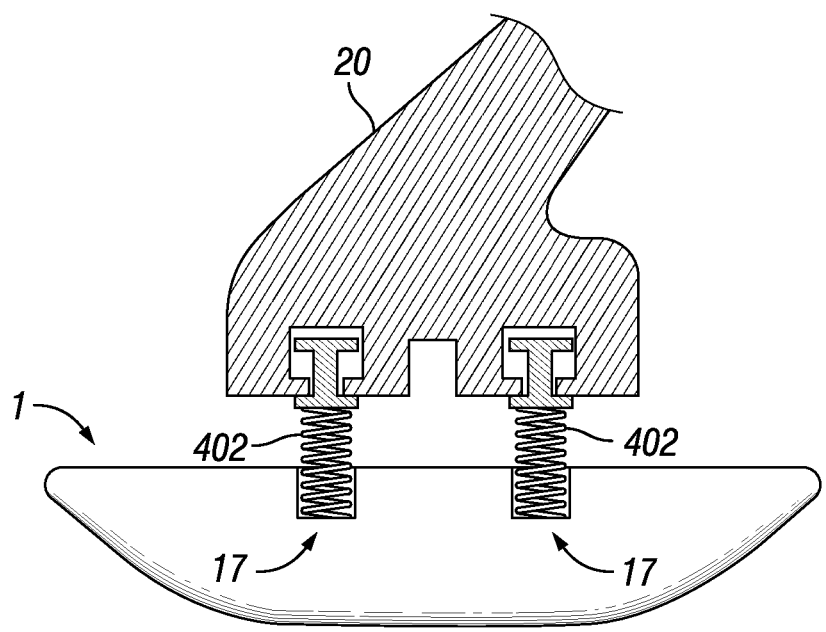
FIG. 18 is a schematic cutaway view of a sled.

An example sled 1, for example as shown in FIG. 18, includes more than one pivot point 17, for example utilizing springs 402 to couple to the sled arm 20. In the example of FIG. 16, the two pivot points 17 provide additional clearance for the sled 1 to clear obstacles. In certain embodiments, both springs 402 may be active, for example allowing some rotation of each pivot simultaneously, and/or a lifting of the entire sled. In certain embodiments, springs 402 may be selectively locked—for example before inspection operations and/or actively controlled during inspection operations. Additionally or alternatively, selection of pivot position, spring force and/or ease of pivoting at each pivot may be selectively controlled—for example before inspection operations and/or actively controlled during inspection operations (e.g., using a controller 802). The utilization of springs 402 is a non-limiting example of simultaneous multiple pivot points, and leaf springs, electromagnets, torsion springs, or other flexible pivot enabling structures are contemplated herein. The spring tension or pivot control may be selected based on the uniformity of the surface to be traversed. The spring tension may be varied between the front and rear pivot points depending on the direction of travel of the sled 1. In an illustrative and non-limiting example, the rear spring (relative to the direction of travel) might be locked and the front spring active when traveling forward to better enable obstacle accommodation. When direction of travel is reversed, the active and locked springs 402 may be reversed such that what was the rear spring 402 may now be active and what was the front spring 402 may now be locked, again to accommodate obstacles encountered in the new direction of travel.

Figure 19A:
FIGS. 19A and 19B depict schematic side views of alternate embodiments of a sled.
Figure 19B:

In embodiments, the bottom surface of the sled 1 may be shaped, as shown in FIGS. 19A, 19B, with one or more ramps 1902 to facilitate the sled 1 moving over obstacles encountered along the direction of travel. The shape and slope of each ramp 1902 may be designed to accommodate conflicting goals such as sled 1 stability, speed of travel, and the size of the obstacle the sled 1 is designed to accommodate. A steep ramp angle might be better for accommodating large obstacles but may be required to move more slowly to maintain stability and a good interaction with the surface. The slope of the ramp 1902 may be selected based on the surface to be traversed and expected obstacles. If the sled 1 is interacting with the surface in only one direction, the sled 1 may be designed with only one ramp 1902. If the sled 1 is interacting with the surface going in two directions, the sled 1 may be designed with two ramps 1902, e.g., a forward ramp and a rearward ramp, such that the sled 1 leads with a ramp 1902 in each direction of travel. Referencing FIG. 19B, the front and rear ramps 1902 may have different angles and/or different total height values. While the ramps 1902 depicted in FIGS. 19A and 19B are linear ramps, a ramp 1902 may have any shape, including a curved shape, a concave shape, a convex shape, and/or combinations thereof. The selection of the ramp angle, total ramp height, and bottom surface shape is readily determinable to one of skill in the art having the benefit of the disclosure herein and information ordinarily available when contemplating a system. Certain considerations for determining the ramp angle, ramp total height, and bottom surface shape include considerations of manufacturability, obstacle geometries likely to be encountered, obstacle materials likely to be encountered, materials utilized in the sled 1 and/or ramp 1902, motive power available to the inspection robot 100, the desired response to encountering obstacles of a given size and shape (e.g., whether it is acceptable to stop operations and re-configure the inspection operations for a certain obstacle, or whether maximum obstacle traversal capability is desired), and/or likely impact speed with obstacles for a sled.

Figure 20A:
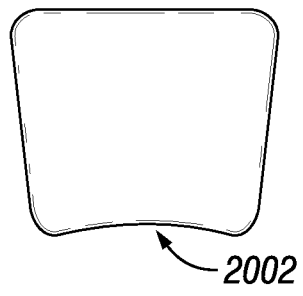
FIGS. 20A and 20B depict schematic front views of alternate embodiments of a sled.
Figure 20B:
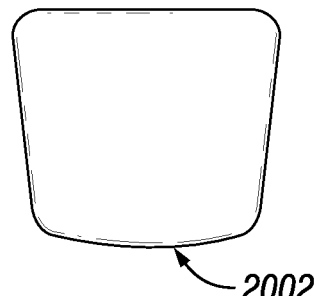

In embodiments, as shown in FIGS. 20A and 20B, the bottom surface 2002 of the sled 1 may be contoured or curved to accommodate a known texture or shape of the surface being traversed, for example such that the sled 1 will tend to remain in a desired orientation (e.g., perpendicular) with the inspection surface as the sled 1 is moved. The bottom surface 2002 of the sled 1 may be shaped to reduce rotation, horizontal translation and shifting, and/or yaw or rotation of the sled 1 from side to side as it traverses the inspection surface. Referencing FIG. 20B, the bottom surface 2002 of the sled 1 may be convex for moving along a rounded surface, on the inside of a pipe or tube, and/or along a groove in a surface. Referencing FIG. 20A, the bottom surface 2002 of the sled 1 may be concave for the exterior of a rounded surface, such as riding on an outer wall of a pipe or tube, along a rounded surface, and/or along a ridge in a surface. The radius of curvature of the bottom surface 2002 of the sled 1 may be selected to facilitate alignment given the curvature of the surface to be inspected. The bottom surface 2002 of the sled 1 may be shaped to facilitate maintaining a constant distance between sensors or tools in the sled 1 and the inspection surface being traversed. In embodiments, at least a portion the bottom of the sled 1 may be flexible such that the bottom of the sled 1 may comply to the shape of the surface being traversed. This flexibility may facilitate traversing surfaces that change curvature over the length of the surface without the adjustments to the sled 1.

For a surface having a variable curvature, a chamfer or curve on the bottom surface 2002 of a sled 1 tends to guide the sled 1 to a portion of the variable curvature matching the curvature of the bottom surface 2002. Accordingly, the curved bottom surface 2002 supports maintaining a selected orientation of the sled 1 to the inspection surface. In certain embodiments, the bottom surface 2002 of the sled 1 is not curved, and one or more pivots 16, 17, 18 combined with the down force from the arms 20 combine to support maintaining a selected orientation of the sled 1 to the inspection surface. In some embodiments, the bottom of the sled 1 may be flexible such that the curvature may adapt to the curvature of the surface being traversed.

Figure 21:
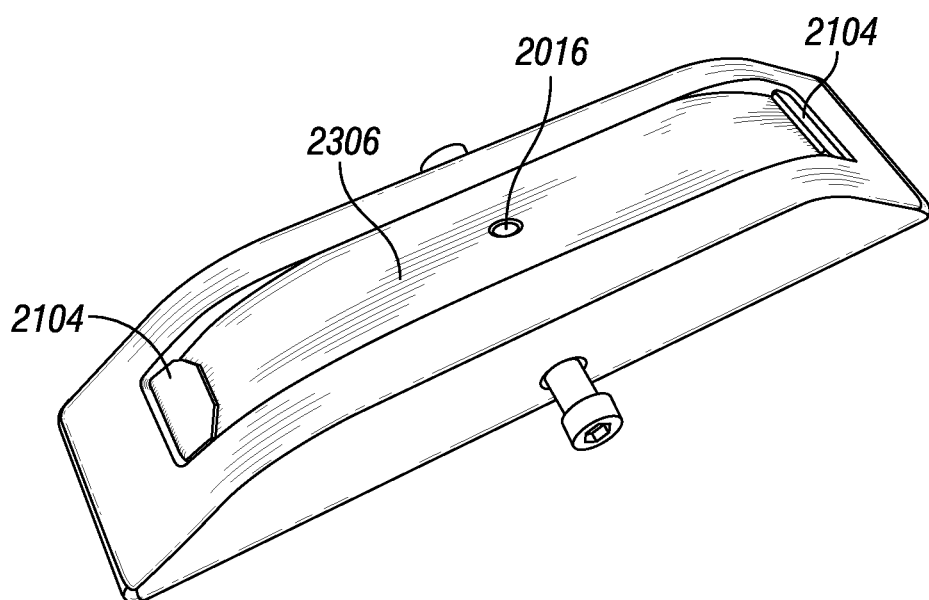
FIG. 21 is a schematic bottom view of a sled.
Figure 22:
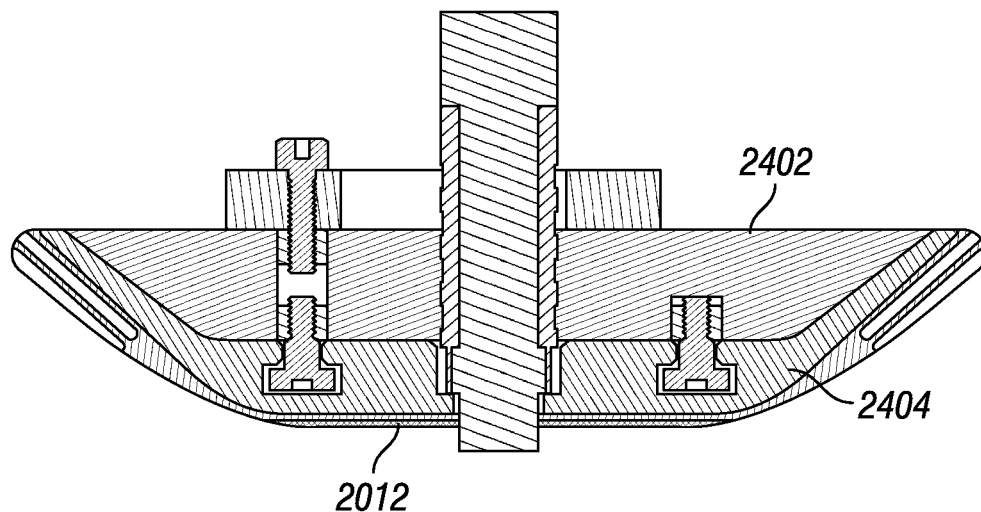
FIG. 22 is a schematic cutaway side view of a sled.

The material on the bottom of the sled 1 may be chosen to prevent wear on the sled 1, reduce friction between the sled 1 and the surface being traversed, or a combination of both. Materials for the bottom of the sled may include materials such as plastic, metal, or a combination thereof. Materials for the bottom of the sled may include an epoxy coat, a replaceable layer of polytetrafluoroethylene (e.g., Teflon, acetyl (e.g., Delrin® acetyl resin), ultrafine molecular weight polyethylene (PMW), and the like. In embodiments, as shown in FIG. 22, the material on the bottom of the sled 1 may be removable layer such as a sacrificial film 2012 (or layer, and/or removable layer) that is applied to the bottom of the sled 1 and then lifted off and replaced at selected intervals, before each inspection operation, and/or when the film 2012 or bottom of the sled begin to show signs of wear or an increase in friction. An example sled 1 includes an attachment mechanism 2104, such as a clip, to hold the sacrificial film 2012 in place. Referencing FIG. 21, an example sled 1 includes a recess 2306 in the bottom surface of the sled to retain the sacrificial film 2012 and allow the sacrificial film 2012 to have a selected spatial orientation between the inspection contact side (e.g., the side of the sacrificial film 2012 exposed to the inspection surface) with the bottom surface 2002 of the sled 1 (e.g., flush with the bottom, extending slightly past the bottom, etc.). In certain embodiments, the removable layer may include a thickness that provides a selected spatial orientation between an inspection contact side in contact with the inspection surface and the bottom surface of the sled. In certain embodiments, the sacrificial film 2012 includes an adhesive, for example with an adhesive backing to the layer, and/or may be applied as an adhesive (e.g., an epoxy layer or coating that is refreshed or reapplied from time to time). An example sacrificial film 2012 includes a hole therethrough, for example allowing for visual and/or couplant contact between a sensor 2202 attached to the sled 1 and the inspection surface. The hole may be positioned over the sensor 2202, and/or may accommodate the sensor 2202 to extend through the sacrificial film 2012, and/or may be aligned with a hole 2016 (e.g., FIG. 21) or aperture 12 (e.g., FIG. 3B) in the sled bottom.

Figure 23:
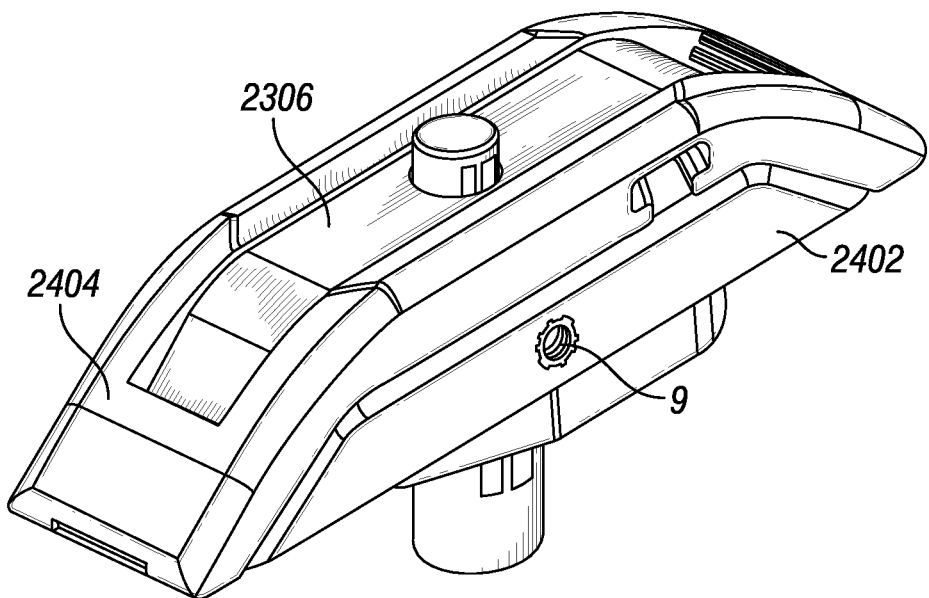
FIG. 23 is a schematic bottom view of a sled.
Figure 24:
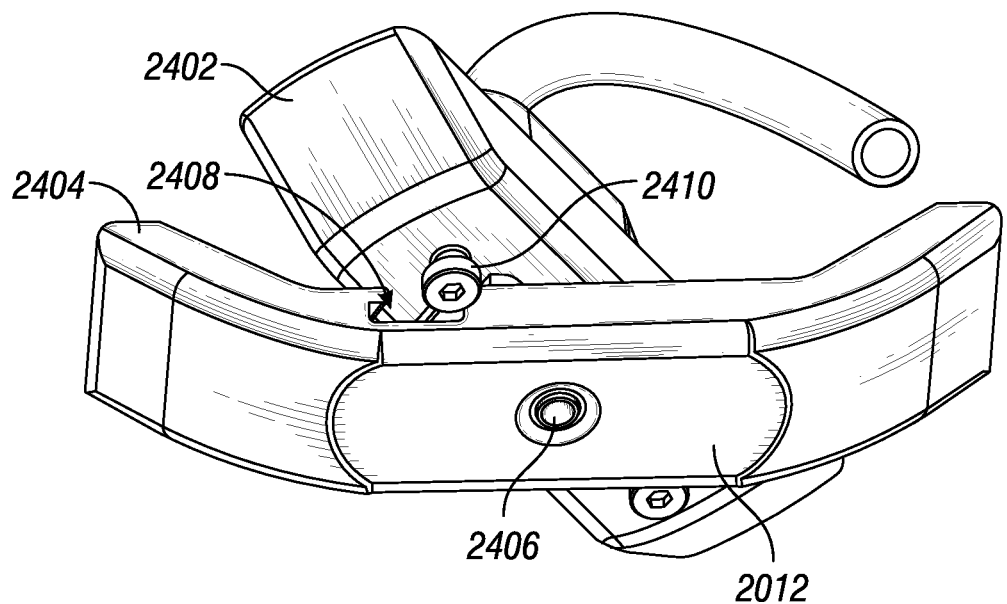
FIG. 24 is a schematic view of a sled having separable top and bottom portions.

In embodiments, as shown in FIG. 22-24, an example sled 1 includes an upper portion 2402 and a replaceable lower portion 2404 having a bottom surface. In some embodiments, the lower portion 2404 may be designed to allow the bottom surface and shape to be changed to accommodate the specific surface to be traversed without having to disturb or change the upper portion 2402. Accordingly, where sensors or tools engage the upper portion 2402, the lower portion 2404 can be rapidly changed out to configure the sled 1 to the inspection surface, without disturbing sensor connections and/or coupling to the arms 20. The lower portion 2404 may additionally or alternatively be configured to accommodate a sacrificial layer 2012, including potentially with a recess 2306. An example sled 1 includes a lower portion 2404 designed to be easily replaced by lining up the upper portion 2402 and the lower portion 2404 at a pivot point 2406, and then rotating the pieces to align the two portions. In certain embodiments, the sensor, installation sleeve, cone tip, or other portion protruding through aperture 12 forms the pivot point 2406. One or more slots 2408 and key 2410 interfaces or the like may hold the two portions together.

The ability to quickly swap the lower portion 2404 may facilitate changing the bottom surface of the sled 1 to improve or optimize the bottom surface of the sled 1 for the surface to be traversed. The lower portion may be selected based on bottom surface shape, ramp angle, or ramp total height value. The lower portion may be selected from a multiplicity of pre-configured replaceable lower portions in response to observed parameters of the inspection surface after arrival to an inspection site. Additionally or alternatively, the lower portion 2404 may include a simple composition, such as a wholly integrated part of a single material, and/or may be manufactured on-site (e.g., in a 3-D printing operation) such as for a replacement part and/or in response to observed parameters of the inspection surface after arrival to an inspection site. Improvement and/or optimization may include: providing a low friction material as the bottom surface to facilitate the sled 1 gliding over the surface being traversed, having a hardened bottom surface of the sled 1 if the surface to be traversed is abrasive, producing the lower portion 2404 as a wear material or low-cost replacement part, and the like. The replacement lower portion 2404 may allow for quick replacement of the bottom surface when there is wear or damage on the bottom surface of the sled 1. Additionally or alternatively, a user may alter a shape/curvature of the bottom of the sled, a slope or length of a ramp, the number of ramps, and the like. This may allow a user to swap out the lower portion 2404 of an individual sled 1 to change a sensor to a similar sensor having a different sensitivity or range, to change the type of sensor, manipulate a distance between the sensor and the inspection surface, replace a failed sensor, and the like. This may allow a user to swap out the lower portion 2404 of an individual sled 1 depending upon the surface curvature of the inspection surface, and/or to swap out the lower portion 2404 of an individual sled 1 to change between various sensors and/or tools.

Figure 25:
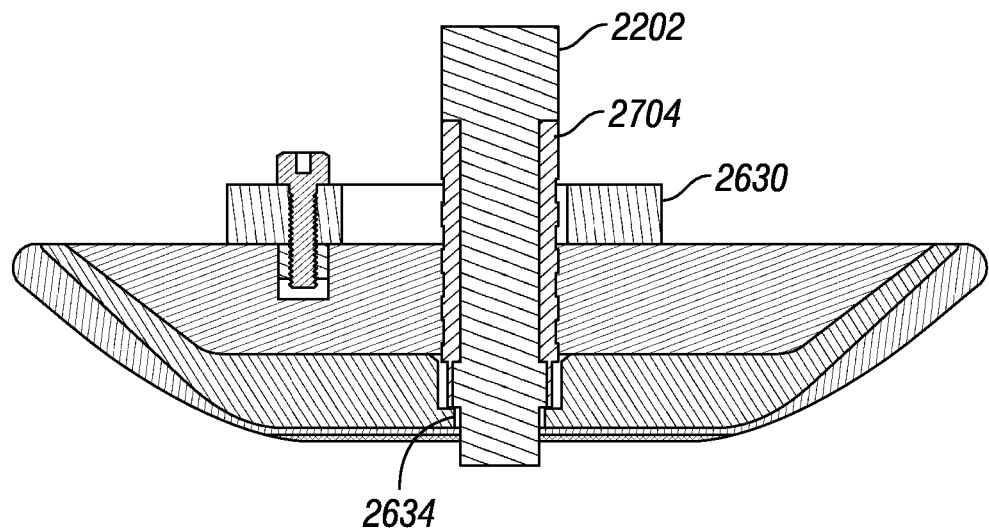
FIG. 25 is a schematic cutaway side view of a sled.
Figure 26:
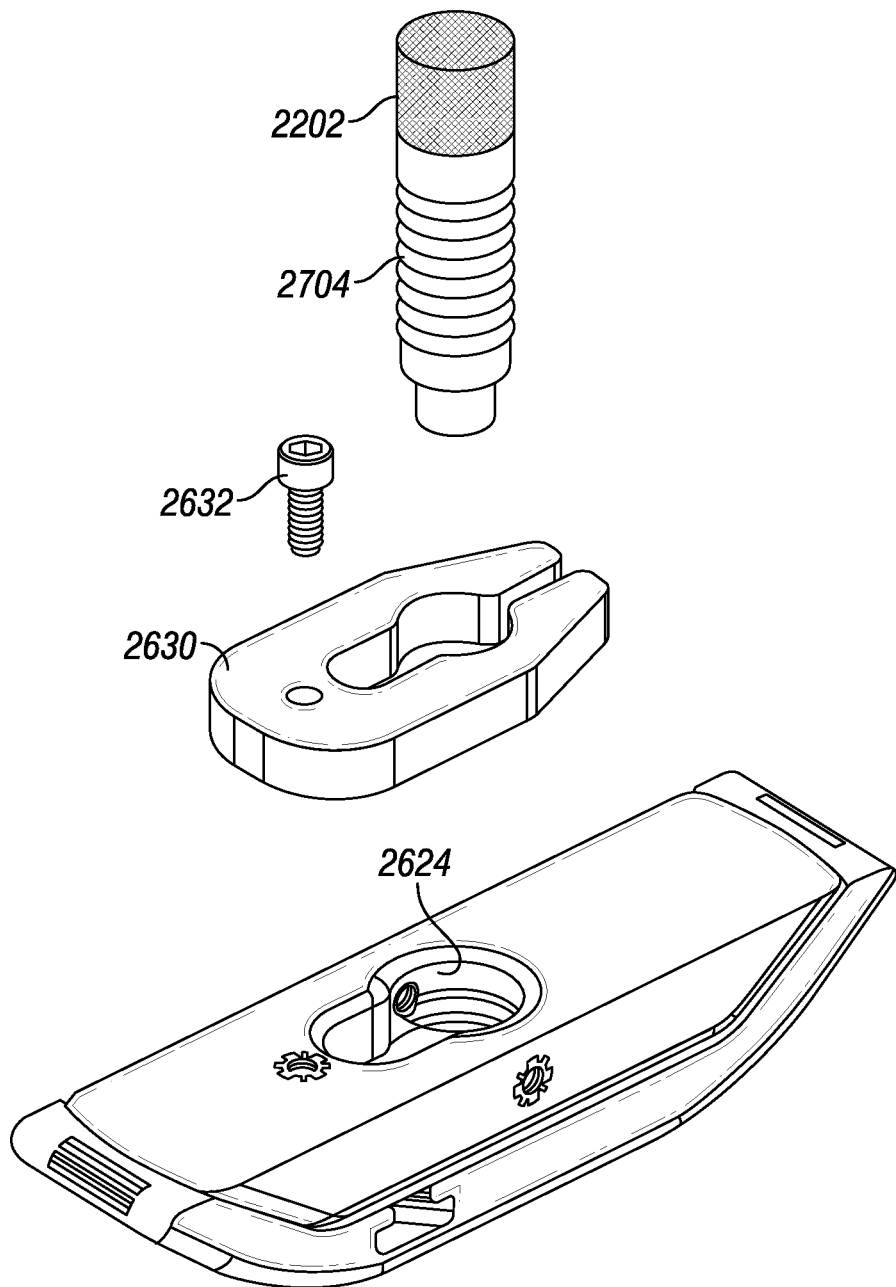
FIG. 26 is a schematic exploded view of a sled with a sensor.
Figure 27:
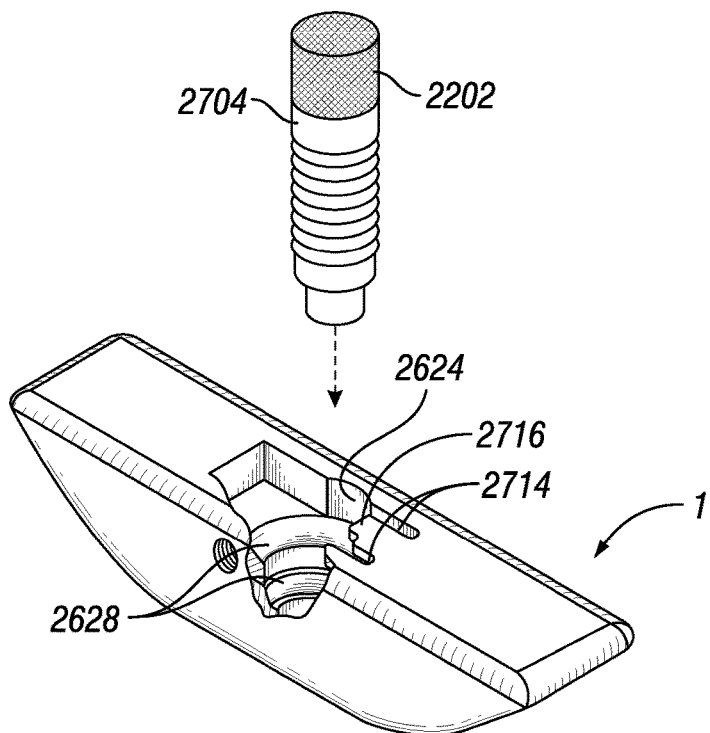
FIG. 27 is a schematic, partially exploded, partially cutaway view of a sled with a sensor.

In embodiments, as shown in FIGS. 25-27, a sled 1 may have a chamber 2624 sized to accommodate a sensor 2202, and/or into which a sensor 2202 may be inserted. The chamber 2624 may have chamfers 2628 on at least one side of the chamber to facilitate ease of insertion and proper alignment of the sensor 2202 in the chamber 2624. An example sled 1 includes a holding clamp 2630 that accommodates the sensor 2202 to pass therethrough, and is attached to the sled 1 by a mechanical device 2632 such as a screw or the like. An example sled 1 includes stops 2634 at the bottom of the chamber 2624, for example to ensure a fixed distance between the sensor 2202 and bottom surface of the sled and/or the inspection surface, and/or to ensure a specific orientation of the sensor 2202 to the bottom surface of the sled and/or the inspection surface.

Referencing FIG. 27, an example sled 1 includes a sensor installation sleeve 2704, which may be positioned, at least partially, within the chamber. The example sensor installation sleeve 2704 may be formed from a compliant material such as neoprene, rubber, an elastomeric material, and the like, and in certain embodiments may be an insert into a chamber 2624, a wrapper material on the sensor 2202, and/or formed by the substrate of the sled 1 itself (e.g., by selecting the size and shape of the chamber 2624 and the material of the sled 1 at least in the area of the chamber 2624). An example sleeve 2704 includes an opening 2 sized to receive a sensor 2202 and/or a tool (e.g., marking, cleaning, repair, and/or spray tool). In the example of FIG. 27, the sensor installation sleeve 2704 flexes to accommodate the sensor 2202 as the sensor 2202 is inserted. Additionally or alternatively, a sleeve 2704 may include a material wrapping the sensor 2202 and slightly oversized for the chamber 2624, where the sleeve compresses through the hole into the chamber 2624, and expands slightly when released, thereby securing the sensor 2202 into the sled 1. In the example of FIG. 27, an installation tab 2716 is formed by relief slots 2714. The tab 2716 flexes to engage the sensor 2202, easing the change of the sensor 2202 while securing the sensor 2202 in the correct position once inserted into the sled 1.

It can be seen that a variety of sensor and tool types and sizes may be swapped in and out of a single sled 1 using the same sensor installation sleeve 2704. The opening of the chamber 2624 may include the chamfers 2628 to facilitate insertion, release, and positioning of the sensor 2202, and/or the tab 2716 to provide additional compliance to facilitate insertion, release, and positioning of the sensor 2202 and/or to accommodate varying sizes of sensors 2202. Throughout the present disclosure, a sensor 2202 includes any hardware of interest for inserting or coupling to a sled 1, including at least: a sensor, a sensor housing or engagement structure, a tool (e.g., a sprayer, marker, fluid jet, etc.), and/or a tool housing or engagement structure.

Figure 28:
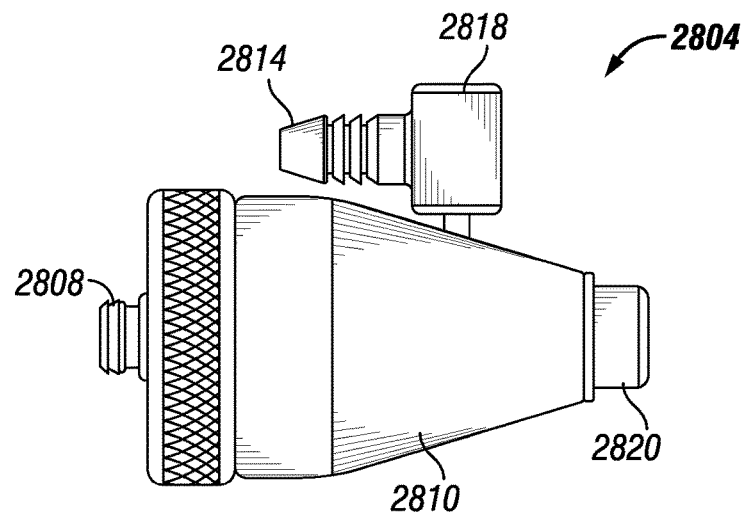
FIG. 28 is a schematic depiction of an acoustic cone.

Referencing FIG. 28, an acoustic cone 2804 is depicted. The acoustic cone 2804 includes a sensor interface 2808, for example to couple an acoustic sensor with the cone 2804. The example acoustic cone 2804 includes a couplant interface 2814, with a fluid chamber 2818 coupling the couplant interface 2814 to the cone fluid chamber 2810. In certain embodiments, the cone tip 2820 of the acoustic cone 2804 is kept in contact with the inspection surface, and/or kept at a predetermined distance from the inspection surface while the acoustic sensor is mounted at the opposite end of the acoustic cone 2804 (e.g., at sensor interface 2808). The cone tip 2820 may define a couplant exit opening between the couplant chamber and the inspection surface. The couplant exit opening may be flush with the bottom surface or extend through the bottom of the sled. Accordingly, a delay line (e.g., acoustic or vibration coupling of a fixed effective length) between the sensor and the inspection surface is kept at a predetermined distance throughout inspection operations. Additionally, the acoustic cone 2804 couples to the sled 1 in a predetermined arrangement, allowing for replacement of the sensor, and/or swapping of a sled 1 without having to recalibrate acoustic and/or ultra-sonic measurements. The volume between the sensor and the inspection surface is maintained with couplant, providing a consistent delay line between the sensor and the inspection surface. Example and non-limiting couplant fluids include alcohol, a dye penetrant, an oil-based liquid, an ultra-sonic gel, or the like. An example couplant fluid includes particle sizes not greater than 1/16 of an inch. In certain embodiments, the couplant is filtered before delivery to the sled 1. In certain embodiments, the couplant includes water, which is low cost, low viscosity, easy to pump and compatible with a variety of pump types, and may provide lower resistance to the movement of the inspection sled over the surface than gels. In certain embodiments, water may be an undesirable couplant, and any type of couplant fluid may be provided.

An example acoustic cone 2804 provides a number of features to prevent or remove air bubbles in the cone fluid chamber 2810. An example acoustic cone 2804 includes entry of the fluid chamber 2818 into a vertically upper portion of the cone fluid chamber 2810 (e.g., as the inspection robot 100 is positioned on the inspection surface, and/or in an intended orientation of the inspection robot 100 on the inspection surface, which may toward the front of the robot where the robot is ascending vertically), which tends to drive air bubbles out of the cone fluid chamber 2810. In certain embodiments, the utilization of the acoustic cone 2804, and the ability to minimize sensor coupling and de-coupling events (e.g., a sled can be swapped out without coupling or decoupling the sensor from the cone) contributes to a reduction in leaks and air bubble formation. In certain embodiments, a controller 802 periodically and/or in response to detection of a potential air bubble (e.g., due to an anomalous sensor reading) commands a de-bubbling operation, for example increasing a flow rate of couplant through the cone 2804. In certain embodiments, the arrangements described throughout the present disclosure provide for sufficient couplant delivery to be in the range of 0.06 to 0.08 gallons per minute using a 1/8" fluid delivery line to the cone 2804. In certain embodiments, nominal couplant flow and pressure is sufficient to prevent the formation of air bubbles in the acoustic cone 2804.

Figure 29:
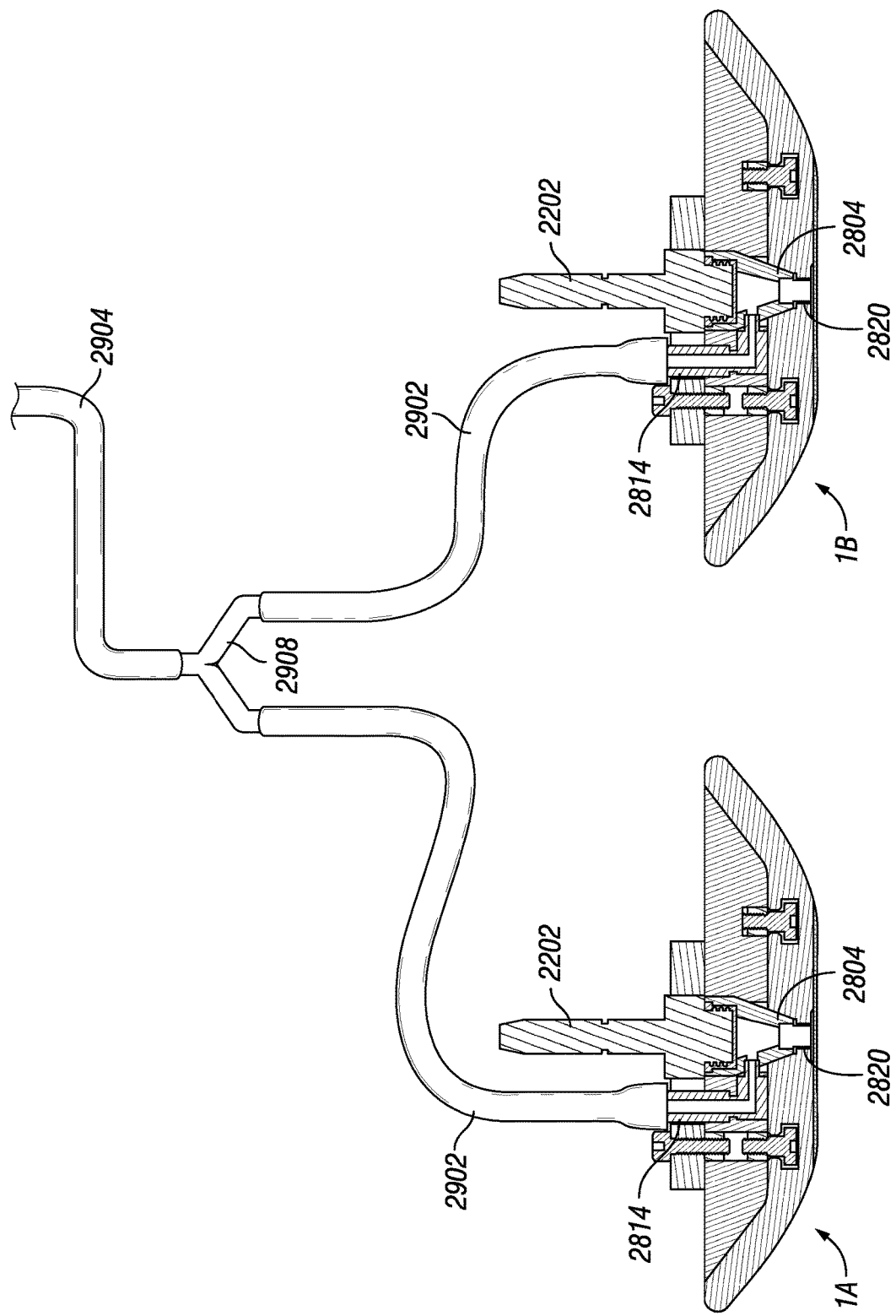
FIG. 29 is a schematic view of couplant lines to a number of sleds.

As shown in FIG. 29, individual tubing 2902 may be connected to each couplant interface 2814. In some embodiments, the individual tubing 2902 may be connected directly to a sled 1A, 1B rather than the individual tubing 2902, for example with sled 1A, 1B plumbing permanently coupled to the couplant interface 2814. Two or more individual tubing 2902 sections may then be joined together in a tubing junction 2908 with a single tube 2904 leaving the junction. In this way, a number of individual tubes 2902 may be reduced to a single tube 2904 that may be easily connected/disconnected from the source of the couplant. In certain embodiments, an entire payload 2 may include a single couplant interface, for example to the inspection robot 100. The inspection robot 100 may include a couplant reservoir and/or a delivery pump thereupon, and/or the inspection robot 100 may be connected to an external couplant source. In certain embodiments, an entire payload 2 can be changed out with a single couplant interface change, and without any of the cone couplant interfaces and/or sensor couplant interface being disconnected. In certain embodiments, the integration of the sensor 2202, acoustic cone 2804, and cone tip 2820 is designed to maintain a constant distance between the surface being measured and the acoustic sensor 2202. The constant distance facilitates in the interpretation of the data recorded by the acoustic sensor 2202. In certain embodiments, the distance between the surface being measured and the acoustic sensor 2202 may be described as the "delay line."

Certain embodiments include an apparatus for providing acoustic coupling between a carriage (or sled) mounted sensor and an inspection surface. Example and non-limiting structures to provide acoustic coupling between a carriage mounted sensor and an inspection surface include an acoustic (e.g., an ultra-sonic) sensor mounted on a sled 1, the sled 1 mounted on a payload 2, and the payload 2 coupled to an inspection robot. An example apparatus further includes providing the sled 1 with a number of degrees of freedom of motion, such that the sled 1 can maintain a selected orientation with the inspection surface—including a perpendicular orientation and/or a selected angle of orientation. Additionally or alternatively, the sled 1 is configured to track the surface, for example utilizing a shaped bottom of the sled 1 to match a shape of the inspection surface or a portion of the inspection surface, and/or the sled 1 having an orientation such that, when the bottom surface of the sled 1 is positioned against the inspection surface, the sensor maintains a selected angle with respect to the inspection surface.

Certain additional embodiments of an apparatus for providing acoustic coupling between a carriage mounted sensor and an inspection surface include utilization of a fixed-distance structure that ensures a consistent distance between the sensor and the inspection surface. For example, the sensor may be mounted on a cone, wherein an end of the cone touches the inspection surface and/or is maintained in a fixed position relative to the inspection surface, and the sensor mounted on the cone thereby is provided at a fixed distance from the inspection surface. In certain embodiments, the sensor may be mounted on the cone, and the cone mounted on the sled 1, such that a change-out of the sled 1 can be performed to change out the sensor, without engaging or disengaging the sensor from the cone. In certain embodiments, the cone may be configured such that couplant provided to the cone results in a filled couplant chamber between a transducer of the sensor and the inspection surface. In certain additional embodiments, a couplant entry position for the cone is provided at a vertically upper position of the cone, between the cone tip portion and the sensor mounting end, in an orientation of the inspection robot as it is positioned on the surface, such that couplant flow through the cone tends to prevent bubble formation in the acoustic path between the sensor and the inspection surface. In certain further embodiments, the couplant flow to the cone is adjustable, and is capable, for example, to be increased in response to a determination that a bubble may have formed within the cone and/or within the acoustic path between the sensor and the inspection surface. In certain embodiments, the sled 1 is capable of being lifted, for example with an actuator that lifts an arm 20, and/or that lifts a payload 2, such that a free fluid path for couplant and attendant bubbles to exit the cone and/or the acoustic path is provided. In certain embodiments, operations to eliminate bubbles in the cone and/or acoustic path are performed periodically, episodically (e.g., after a given inspection distance is completed, at the beginning of an inspection run, after an inspection robot pauses for any reason, etc.), and/or in response to an active determination that a bubble may be present in the cone and/or the acoustic path.

An example apparatus provides for low or reduced fluid loss of couplant during inspection operations. Example and non-limiting structures to provide for low or reduced fluid loss include providing for a limited flow path of couplant out of the inspection robot system—for example utilizing a cone having a smaller exit couplant cross-sectional area than a cross-sectional area of a couplant chamber within the cone. In certain embodiments, an apparatus for low or reduced fluid loss of couplant includes structures to provide for a selected down force on a sled 1 which the sensor is mounted on, on an arm 20 carrying a sled 1 which the sensor is mounted on, and/or on a payload 2 which the sled 1 is mounted on. Additionally or alternatively, an apparatus providing for low or reduced fluid loss of couplant includes a selected down force on a cone providing for couplant connectivity between the sensor and the inspection surface—for example a leaf spring or other biasing member within the sled 1 providing for a selected down force directly to the cone. In certain embodiments, low or reduced fluid loss includes providing for an overall fluid flow of between 0.12 to 0.16 gallons per minute to the inspection robot to support at least 10 ultra-sonic sensors. In certain embodiments, low or reduced fluid loss includes providing for an overall fluid flow of less than 50 feet per minute, less than 100 feet per minute, and less than 200 feet per minute fluid velocity in a tubing line feeding couplant to the inspection robot. In certain embodiments, low or reduced fluid loss includes providing sufficient couplant through a ¼" tubing line to feed couplant to at least 6, at least 8, at least 10, at least 12, or at least 16 ultra-sonic sensors to a vertical height of at least 25 feet, at least 50 feet, at least 100 feet, at least 150 feet, or at least 200 feet. An example apparatus includes a ¼" feed line to the inspection robot and/or to the payload 2, and a ⅛" feed line to individual sleds 1 and/or sensors (or acoustic cones associated with the sensors). In certain embodiments, larger and/or smaller diameter feed and individual fluid lines are provided.

Figure 30:
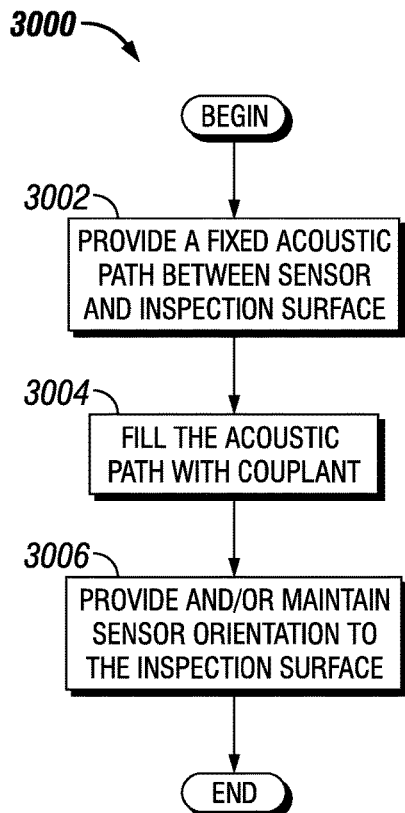
FIG. 30 is a schematic flow diagram of a procedure to provide sensors for inspection of an inspection surface.

Referencing FIG. 30, an example procedure 3000 to provide acoustic coupling between a sensor and an inspection surface is depicted schematically. The example procedure 3000 includes an operation 3002 to provide a fixed acoustic path between the sensor and the inspection surface. The example procedure 3000 further includes an operation 3004 to fill the acoustic path with a couplant. The example procedure 3000 further includes an operation 3006 to provide for a selected orientation between the sensor and the inspection surface. In certain embodiments, certain operations of the procedure 3000 are performed iteratively throughout inspection operations—for example operations 3006 may include maintaining the orientation throughout inspection operations—such as providing the sensor on a sled having a bottom surface and/or maneuverability to passively or actively self-align to the inspection surface, and/or to return to alignment after a disturbance such as traversal of an obstacle. In another example, operations 3004 include providing a couplant flow to keep the acoustic path between the sensor and the inspection surface filled with couplant, and/or adjusting the couplant flow during inspection operations. Certain operations of procedure 3000 may be performed by a controller 802 during inspection operations.

Figure 31:
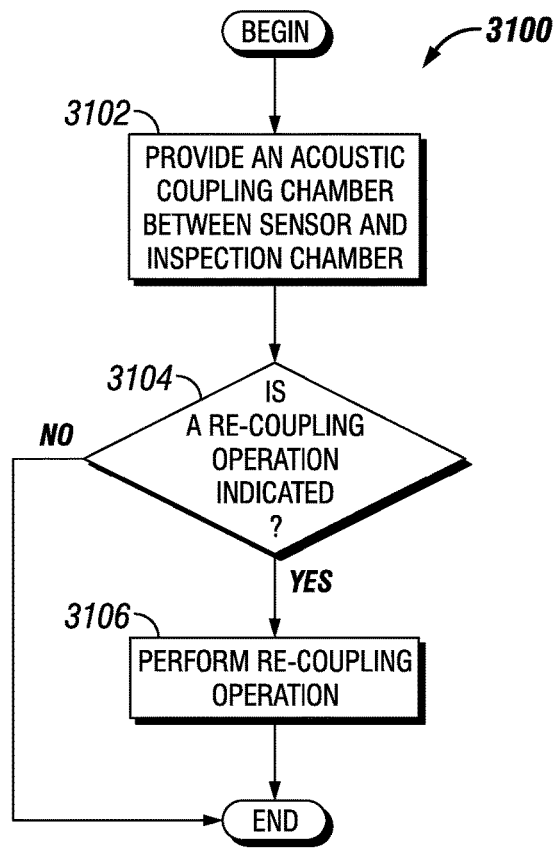
FIG. 31 is a schematic flow diagram of a procedure to re-couple a sensor to an inspection surface.

Referencing FIG. 31, an example procedure 3100 to ensure acoustic engagement between a sensor and an inspection surface is depicted schematically. The example procedure 3100 includes an operation 3102 to provide an acoustic coupling chamber between the sensor and the inspection surface. Example and non-limiting operations 3102 include providing the acoustic coupling chamber with an arrangement that tends to reduce bubble formation within the acoustic path between the sensor and the inspection surface. The example procedure 3100 further includes an operation 3104 to determine that the sensor should be re-coupled to the inspection surface. Example and non-limiting operations 3104 include determining that a time has elapsed since a last re-coupling operation, determining that an event has occurred and performing a re-coupling operation in response to the event, and/or actively determining that the acoustic path has been interrupted. Example and non-limiting events include a pausing of the inspection robot, a beginning of inspection operations and/or completion of a selected portion of inspection operations, and/or an interruption of couplant flow to the inspection robot. Example and non-limiting operation to actively determine that the acoustic path has been interrupted include an observation of a bubble (e.g., in an acoustic cone), an indication that couplant may have exited the acoustic path (e.g., the sled 1 has lifted either for an obstacle or for another operation, observation of an empty cone, etc.), and/or an indication that a sensor reading is off-nominal (e.g., signal seems to have been lost, anomalous reading has occurred, etc.). The example procedure 3100 further includes an operation 3106 to re-couple the sensor to the inspection surface. Example and non-limiting operations 3106 include resuming and/or increasing a couplant flow rate, and/or briefly raising a sled, sled arm, and/or payload from the inspection surface. The procedure 3100 and/or portions thereof may be repeated iteratively during inspection operations. Certain operations of procedure 3100 may be performed by a controller 802 during inspection operations.

Figure 32:
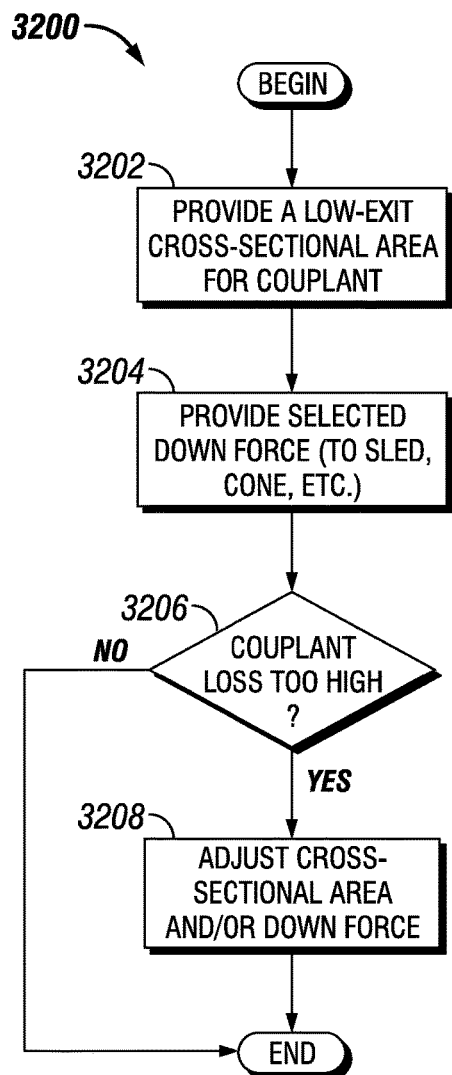
FIG. 32 is a schematic flow diagram of a procedure to provide for low couplant loss.

Referencing FIG. 32, an example procedure 3200 to provide low fluid loss (and/or fluid consumption) between an acoustic sensor and an inspection surface is depicted schematically. An example procedure 3200 includes an operation 3202 to provide for a low exit cross-sectional area for couplant from an acoustic path between the sensor and the inspection surface—including at least providing an exit from a couplant chamber formed by a cone as the exit cross-sectional area—and/or providing an exit cross-sectional area that is in a selected proximity to, and/or in contact with, the inspection surface. The example procedure 3200 further includes an operation 3204 to provide a selected down force to a sled having the sensor mounted thereon, and/or to a couplant chamber. In certain embodiments, the example procedure 3200 includes an operation 3206 to determine if fluid loss for the couplant is excessive (e.g., as measured by replacement couplant flow provided to an inspection robot, and/or by observed couplant loss), and an operation 3208 to increase a down force and/or reduce a couplant exit cross-sectional area from a couplant chamber. In certain embodiments, an inspection robot includes a configurable down force, such as: an active magnet strength control; a biasing member force adjustment (e.g., increasing confinement of a spring to increase down force); sliding of a weight in a manner to adjust down force on the sled and/or cone; combinations of these; or the like. In certain embodiments, an exit cross-sectional are for couplant is adjustable—for example an iris actuator (not shown), gate valve, or cross-sectional area adjustment is provided. In certain embodiments, cross-sectional area is related to the offset distance of the couplant chamber exit (e.g., cone tip) from the inspection surface, whereby a reduction of the selected offset distance of the couplant chamber exit to the inspection surface reduces the effective exit flow area of the couplant chamber. Example operations to adjust the selected offset distance include lowering the couplant chamber within the sled and/or increasing a down force on the sled and/or couplant chamber. Certain operations of procedure 3200 may be performed by a controller 802 during inspection operations.

Figure 2A:
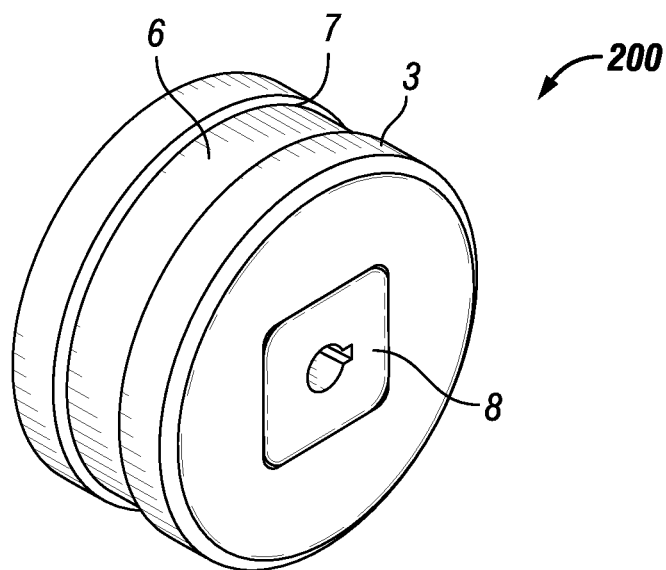
FIG. 2A is a schematic depiction of a wheel and splined hub design consistent with certain embodiments of the present disclosure.
Figure 2B:
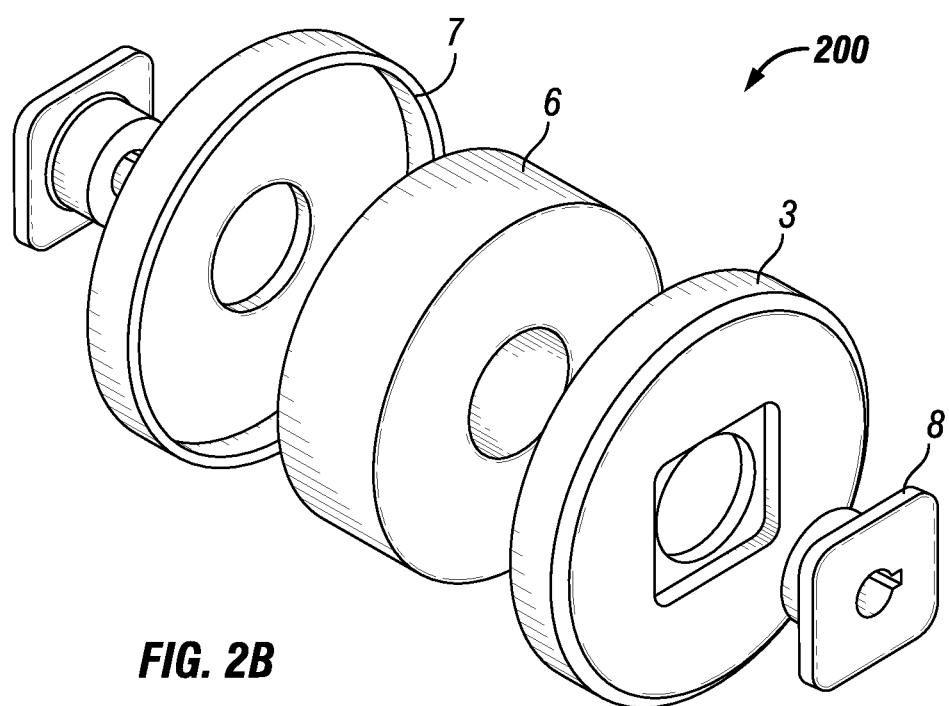
FIG. 2B is an exploded view of a wheel and splined hub design consistent with certain embodiments of the present disclosure.

Referencing FIGS. 2A and 2B, an example system includes a wheel 200 design that enables modularity, adhesion to the structure's surface, and obstacle traversing. A splined hub, wheel size, and the use of magnets allow the system to be effective on many different surfaces. In some embodiments, the wheel 200 includes a splined hub 8. The wheel 200 permits a robotic vehicle 100 to climb on walls, ceilings, and other ferromagnetic surfaces. As shown in the embodiment depicted in FIGS. 2A and 2B, this may be accomplished by embedding magnets 6 in a ferromagnetic enclosure 3 and/or an electrically conductive enclosure to protect the magnet 6, improve alignment, and allow for ease of assembly. For example, the magnet 6 may be a permanent magnet and/or a controllable electromagnet, and may further include a rare earth magnet. The ferromagnetic enclosure 3 protects the magnet 6 from directly impacting the inspected surface, reduces impacts and damage to the magnet 6, and reduces wear on the surface and the magnet 6. The ferromagnetic and/or electrical conductivity of the enclosure 3 reduces magnetic field lines in not-useful directions (e.g., into the housing 102, electrical lines or features that may be present near the inspected surface, etc.) and guides the magnetic field lines to the inspected surface. In certain embodiments, the enclosure 3 may not be ferromagnetic or conductive, and/or the enclosure 3 may be at least partially covered by a further material (e.g., molded plastic, a coating, paint, etc.), for example to protect the inspected surface from damage, to protect the enclosure 3 from wear, for aesthetic reasons, or for any other reason. In certain embodiments, the magnet 6 is not present, and the system 100 stays in contact with the surface in another manner (e.g., surface tension adhesion, gravity such as on a horizontal or slightly inclined inspection surface, movement along a track fixed to the surface, or the like). Any arrangements of an inspection surface, including vertical surfaces, overhang or upside-down surfaces, curved surfaces, and combinations of these, are contemplated herein.

The wheel 200 includes a channel 7 formed between enclosures 3, for example at the center of the wheel 200. In certain embodiments, the channel 7 provides for self-alignment on surfaces such as tubes or pipes. In certain embodiments, the enclosures 300 include one or more chamfered edges or surfaces (e.g., the outer surface in the example of FIG. 3), for example to improve contact with a rough or curved surface, and/or to provide for a selected surface contact area to avoid damage to the surface and/or the wheel 200. The flat face along the rim also allows for adhesion and predictable movement on flat surfaces.

The wheel 200 may be connected to the shaft using a splined hub 8. This design makes the wheel modular and also prevents it from binding due to corrosion. The splined hub 8 transfers the driving force from the shaft to the wheel. An example wheel 200 includes a magnetic aspect (e.g., magnet 6) capable to hold the robot on the wall, and accept a driving force to propel the robot, the magnet 6 positioned between conductive and/or ferromagnetic plates or enclosures, a channel 7 formed by the enclosures or plates, one or more chamfered and/or shaped edges, and/or a splined hub attachment to a shaft upon which the wheel is mounted.

The robotic vehicle may utilize a magnet-based wheel design that enables the vehicle to attach itself to and operate on ferromagnetic surfaces, including vertical and inverted surfaces (e.g., walls and ceilings). As shown in FIGS. 2A and 2B, the wheel design may comprise a cylindrical magnet 6 mounted between two wheel enclosures 3 with a splined hub 8 design for motor torque transfer, where the outer diameter of the two enclosures 3 is greater than the outer diameter of the magnet 6. Once assembled, this configuration creates a channel 7 between the two wheel enclosures 3 that prevents the magnet 6 from making physical contact with the surface as the wheel rolls on the outer diameter surface of the wheel enclosures 3. In certain embodiments, the material of the magnet 6 may include a rare earth material (e.g., neodymium, yttrium-cobalt, samarium-cobalt, etc.), which may be expensive to produce, handle, and/or may be highly subject to damage or corrosion. Additionally, any permanent magnet material may have a shorter service life if exposed to direct shocks or impacts.

The channel 7 may also be utilized to assist in guiding the robotic vehicle along a feature of an inspection surface 500 (e.g., reference FIG. 5), such as where the channel 7 is aligned along the top of a rounded surface (e.g., pipe, or other raised feature) that the wheel uses to guide the direction of travel. The wheel enclosures 3 may also have guiding features 2052 (reference FIGS. 11A to 11E), such as grooves, concave or convex curvature, chamfers on the inner and/or outer edges, and the like. Referencing FIG. 11A, an example guiding feature 2052 includes a chamfer on an outer edge of one or both enclosures 3, for example providing self-alignment of the wheels along a surface feature, such as between raised features, on top of raised features, between two pipes 502 (which may be adjacent pipes or spaced pipes), and/or a curvature of a tube, pipe, or tank (e.g., when the inspection robot 100 traverses the interior of a pipe 502). For instance, having a chamfer on the outer edge of the outside enclosure may enable the wheel to more easily seat next to and track along a pipe 502 that is located outside the wheel. In another instance, having chamfers on both edges may enable the wheel to track with greater stability between two pipes 502. Referencing FIG. 11B, guiding features 2052 are depicted as chamfers on both sides of the wheel enclosures 3—for example allowing the inspection robot 100 to traverse between pipes 502; on top of a single pipe 502 or on top of a span of pipes 502; along the exterior of a pipe, tube, or tank; and/or along the interior of a pipe, tube, or tank. Referencing FIG. 11C, guiding features 2052 are depicted as chamfers on the interior channel 7 side of the enclosures 3, for example allowing the wheel to self-align on top of a single pipe or other feature. Referencing FIG. 11D, guiding features 2052 are depicted as a concave curved surface, for example sized to match a pipe or other feature to be traversed by the wheel. Referencing FIG. 11E, guiding features 2052 are depicted as a concave curved surface formed on an interior of the channel 7, with chamfers 2052 on the exterior of the enclosure 3—for example allowing the wheel to self-align on a single pipe or feature on the interior of the enclosure, and/or to align between pipes on the exterior of the enclosure.

One skilled in the art will appreciate that a great variety of different guiding features 2052 may be used to accommodate the different surface characteristics to which the robotic vehicle may be applied. In certain embodiments, combinations of features (e.g., reference FIG. 11E) provide for the inspection robot 100 to traverse multiple surfaces for a single inspection operation, reducing change-time for the wheels and the like. In certain embodiments, chamfer angles, radius of curvature, vertical depth of chamfers or curves, and horizontal widths of chamfers or curves are selectable to accommodate the sizing of the objects to be traversed during inspection operations. It can be seen that the down force provided by the magnet 6 combined with the shaping of the enclosure 3 guiding features 2052 combine to provide for self-alignment of the inspection robot 100 on the surface 500, and additionally provide for protection of the magnet 6 from exposure to shock, impacts, and/or materials that may be present on the inspection surface. In certain embodiments, the magnet 6 may be shaped—for example with curvature (reference FIG. 11D), to better conform to the inspection surface 500 and/or prevent impact or contact of the magnet 6 with the surface.

Figure 8:
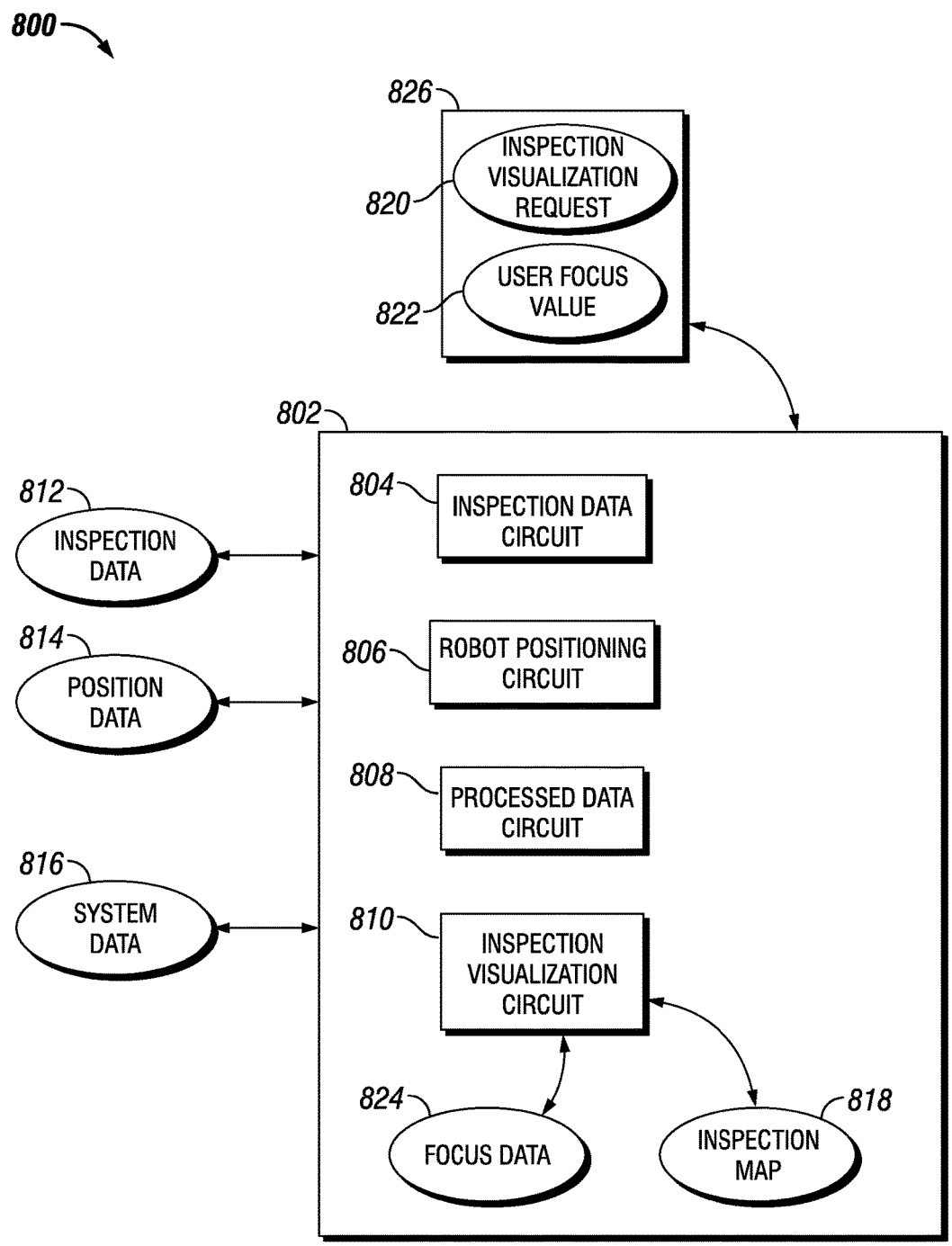
FIG. 8 is a schematic block diagram of an apparatus for providing an inspection map.

Additionally or alternatively, guiding features may be selectable for the inspection surface—for example multiple enclosures 3 (and/or multiple wheel assemblies including the magnet 6 and enclosure 3) may be present for an inspection operation, and a suitable one of the multiple enclosures 3 provided according to the curvature of surfaces present, the spacing of pipes, the presence of obstacles, or the like. In certain embodiments, an enclosure 3 may have an outer layer (e.g., a removable layer—not shown)—for example a snap on, slide over, coupled with set screws, or other coupling mechanism for the outer layer, such that just an outer portion of the enclosure is changeable to provide the guiding features. In certain embodiments, the outer layer may be a non-ferrous material (e.g., making installation and changes of the outer layer more convenient in the presence to the magnet 6, which may complicate quick changes of a fully ferromagnetic enclosure 3), such as a plastic, elastomeric material, aluminum, or the like. In certain embodiments, the outer layer may be a 3-D printable material (e.g., plastics, ceramics, or any other 3-D printable material) where the outer layer can be constructed at an inspection location after the environment of the inspection surface 500 is determined. An example includes the controller 802 (e.g., reference FIG. 8 and the related description) structured to accept inspection parameters (e.g., pipe spacing, pipe sizes, tank dimensions, etc.), and to provide a command to a 3-D printer responsive to the command to provide an outer layer configured for the inspection surface 500. In certain embodiments, the controller 802 further accepts an input for the wheel definition (e.g., where selectable wheel sizes, clearance requirements for the inspection robot 100, or other parameters not necessarily defined by the inspection surface 500), and further provides the command to the 3-D printer, to provide an outer layer configured for the inspection surface 500 and the wheel definition.

An example splined hub 8 design of the wheel assembly may enable modular re-configuration of the wheel, enabling each component to be easily switched out to accommodate different operating environments (e.g., ferromagnetic surfaces with different permeability, different physical characteristics of the surface, and the like). For instance, enclosures with different guiding features may be exchanged to accommodate different surface features, such as where one wheel configuration works well for a first surface characteristic (e.g., a wall with tightly spaced small pipes) and a second wheel configuration works well for a second surface characteristic (e.g., a wall with large pipes). The magnet 6 may also be exchanged to adjust the magnetic strength available between the wheel assembly and the surface, such as to accommodate different dimensional characteristics of the surface (e.g., features that prevent close proximity between the magnet 6 and a surface ferromagnetic material), different permeability of the surface material, and the like. Further, one or both enclosures 3 may be made of ferromagnetic material, such as to direct the flux lines of the magnet toward a surface upon which the robotic vehicle is riding, to direct the flux lines of the magnet away from other components of the robotic vehicle, and the like, enabling the modular wheel configuration to be further configurable for different ferromagnetic environments and applications.

The present disclosure provides for robotic vehicles that include a sensor sled components, permitting evaluation of particular attributes of the structure. As shown in the embodiments depicted in FIGS. 3A to 3C, the sled 1 may hold the sensor that can perform inspection of the structure. The sensor may be perpendicular to the surface being inspected and, in some embodiments, may have a set distance from the surface to protect it from being damaged. In other embodiments, the distance from the surface to the sensor may be adjusted to accommodate the technical requirements of the sensor being utilized A couplant retaining column may be added at the sensor outlet to retain couplant depending on the type of sensor being used. In certain embodiments, an opening 12 may be provided at a bottom of the sled 1 to allow an installed sensor to operatively communicate with an inspection surface.

The sleds of the present disclosure may slide on a flat or curved surface and may perform various types of material testing using the sensors incorporated into the sled. The bottom surface 13 of the sled may be fabricated from numerous types of materials which may be chosen by the user to fit the shape of the surface. Note that depending on the surface condition, a removeable, replaceable, and/or sacrificial layer of thin material may be positioned on the bottom surface of the sled to reduce friction, create a better seal, and protect the bottom of the sled from physical damage incurred by the surface. In certain embodiments, the sled may include ramp surfaces 11 at the front and back of the sled. The ramp and available pivot point accommodation 9 (described below—for example an option for pivot point 17) give the sled the ability to travel over obstacles. This feature allows the sled to work in industrial environments with surfaces that are not clean and smooth. In certain embodiments, one or more apertures 10 may be provided, for example to allow a sacrificial layer to be fixed to the bottom of the sled 1.

In summary, an example robotic vehicle 100 includes sensor sleds having the following properties capable of providing a number of sensors for inspecting a selected object or surface, including a soft or hard bottom surface, including a bottom surface that matches an inspection surface (e.g., shape, contact material hardness, etc.), having a curved surface and/or ramp for obstacle clearance (including a front ramp and/or a back ramp), includes a column and/or couplant insert (e.g., a cone positioned within the sled, where the sensor couples to the cone) that retains couplant, improves acoustic coupling between the sensor and the surface, and/or assists in providing a consistent distance between the surface and the sensor; a plurality of pivot points between the main body 102 and the sled 1 to provide for surface orientation, improved obstacle traversal, and the like, a sled 1 having a mounting position configured to receive multiple types of sensors, and/or magnets in the sled to provide for control of downforce and/or stabilized positioning between the sensor and the surface. In certain implementations of the present invention, it is advantageous to not only be able to adjust spacing between sensors but also to adjust their angular position relative to the surface being inspected. The present invention may achieve this goal by implementing systems having several translational and rotational degrees of freedom.

Referencing FIG. 4, an example payload 2 includes selectable spacing between sleds 1, for example to provide selectable sensor spacing. In certain embodiments, spacing between the sensors may be adjusted using a lockable translational degree of freedom such as a set screw 14 allowing for the rapid adjustment of spacing. Additionally or alternatively, any coupling mechanism between the arm 20 and the payload 2 is contemplated herein. In certain embodiments, a worm gear or other actuator allows for the adjustment of sensor spacing by a controller and/or in real time during operations of the system 100. In certain embodiments, the payload 2 includes a shaft 19 whereupon sleds 1 are mounted (e.g., via the arms 20). In these embodiments, the sensor mounts 14 are mounted on a shaft 19. The example of FIG. 4 includes a shaft cap 15 providing structural support to a number of shafts of the payload 2. In the example of FIG. 4, two shafts are utilized to mount the payload 2 onto the housing 102, and one shaft 19 is utilized to mount the arms 20 onto the payload 2. The arrangement utilizing a payload 2 is a non-limiting example, that allows multiple sensors and sleds 1 to be configured in a particular arrangement, and rapidly changed out as a group (e.g., swapping out a first payload and set of sensors for a second payload and set of sensors, thereby changing an entire sensor arrangement in a single operation). However, in certain embodiments one or more of the payload 2, arms 20, and/or sleds 1 may be fixedly coupled to the respective mounting features, and numerous benefits of the present disclosure are nevertheless achieved in such embodiments.

During operation, an example system 100 encounters obstacles on the surface of the structure being evaluated, and the pivots 16, 17, 18 provide for movement of the arm 20 to traverse the obstacle. In certain embodiments, the system 100 is a modular design allowing various degrees of freedom of movement of sleds 1, either in real-time (e.g., during an inspection operation) and/or at configuration time (e.g., an operator or controller adjusts sensor or sled positions, down force, ramp shapes of sleds, pivot angles of pivots 16, 17, 18 in the system 100, etc.) before an inspection operation or a portion of an inspection operation, and including at least the following degrees of freedom: translation (e.g., payload 2 position relative to the housing 102); translation of the sled arm 20 relative to the payload 2, rotation of the sled arm 20, rotation of the sled arm 20 mount on the payload 2, and/or rotation of the sled 1 relative to the sled arm 20.

In certain embodiments, a system 100 allows for any one or more of the following adjustments: spacing between sensors (perpendicular to the direction of inspection motion, and/or axially along the direction of the inspection motion); adjustments of an angle of the sensor to an outer diameter of a tube or pipe; momentary or longer term displacement to traverse obstacles; provision of an arbitrary number and positioning of sensors; etc.

An example inspection robot 100 may utilize downforce capabilities for sensor sleds 1, such as to control proximity and lateral stabilization of sensors. For instance, an embedded magnet (not shown) positioned within the sled 1 may provide passive downforce that increases stabilization for sensor alignment. In another example, the embedded magnet may be an electromagnet providing active capability (e.g., responsive to commands from a controller 802—reference FIG. 8) that provide adjustable or dynamic control of the downforce provided to the sensor sled. In another example, magnetic downforce may be provided through a combination of a passive permanent magnet and an active electromagnet, providing a default minimum magnetic downforce, but with further increases available through the active electromagnet. In embodiments, the electromagnet may be controlled by a circuit where the downforce is set by the operator, controlled by an on-board processor, controlled by a remote processor (e.g., through wireless communications), and the like, where processor control may utilize sensor data measurements to determine the downforce setting. In embodiments, downforce may be provided through suction force, spring force, and the like. In certain embodiments, downforce may be provided by a biasing member, such as a torsion spring or leaf spring, with active or passive control of the downforce—for example positioning a tension or confinement of the spring to control the downforce. In certain embodiments, the magnet, biasing member, or other downforce adjusting member may adjust the downforce on the entire sled 1, on an entire payload 2, and/or just on the sensor (e.g., the sensor has some flexibility to move within the sled 1, and the downforce adjustment acts on the sensor directly).

An example system 100 includes an apparatus 800 (reference FIG. 8 and the disclosure referencing FIG. 8) for providing enhanced inspection information, including position-based information. The apparatus 800 and operations to provide the position-based information are described in the context of a particular physical arrangement of an industrial system for convenient illustration, however any physical arrangement of an industrial system is contemplated herein. Referencing FIG. 5, an example system includes a number of pipes 502—for example vertically arranged pipes such as steam pipes in a power plant, pipes in a cooling tower, exhaust or effluent gas pipes, or the like. The pipes 502 in FIG. 5 are arranged to create a tower having a circular cross-section for ease of description. In certain embodiments, periodic inspection of the pipes is utilized to ensure that pipe degradation is within limits, to ensure proper operation of the system, to determine maintenance and repair schedules, and/or to comply with policies or regulations. In the example of FIG. 5, an inspection surface 500 includes the inner portion of the tower, whereby an inspection robot 100 traverses the pipes 502 (e.g., vertically, inspecting one or more pipes on each vertical run). An example inspection robot 100 includes configurable payloads 2, and may include ultra-sonic sensors (e.g., to determine wall thickness and/or pipe integrity), magnetic sensors (e.g., to determine the presence and/or thickness of a coating on a pipe), cameras (e.g., to provide for visual inspection, including in EM ranges outside of the visual range, temperatures, etc.), composition sensors (e.g., gas chromatography in the area near the pipe, spectral sensing to detect leaks or anomalous operation, etc.), temperature sensing, pressure sensing (ambient and/or specific pressures), vibration sensing, density sensing, etc. The type of sensing performed by the inspection robot 100 is not limiting to the present disclosure except where specific features are described in relation to specific sensing challenges and opportunities for those sensed parameters as will be understood to one of skill in the art having the benefit of the disclosures herein.

In certain embodiments, the inspection robot 100 has alternatively or additionally, payload(s) 2 configured to provide for marking of aspects of the inspection surface 500 (e.g., a paint sprayer, an invisible or UV ink sprayer, and/or a virtual marking device configured to mark the inspection surface 500 in a memory location of a computing device but not physically), to repair a portion of the inspection surface 500 (e.g., apply a coating, provide a welding operation, apply a temperature treatment, install a patch, etc.), and/or to provide for a cleaning operation. Referencing FIG. 6, an example inspection robot 100 is depicted in position on the inspection surface 500 at a location. In the example, the inspection robot 100 traverses vertically and is positioned between two pipes 502, with payloads 2 configured to clean, sense, treat, and/or mark two adjacent pipes 502 in a single inspection run. The inspection robot 100 in the example includes two payloads 2 at the "front" (ahead of the robot housing in the movement direction) and two payloads 2 at the "rear" (behind the robot housing in the movement direction). The inspection robot 100 may include any arrangement of payloads 2, including just one or more payloads in front or behind, just one or more payloads off to either or both sides, and combinations of these. Additionally or alternatively, the inspection robot 100 may be positioned on a single pipe, and/or may traverse between positions during an inspection operation, for example to inspect selected areas of the inspection surface 502 and/or to traverse obstacles which may be present.

In certain embodiments, a "front" payload 2 includes sensors configured to determine properties of the inspection surface, and a "rear" payload 2 includes a responsive payload, such as an enhanced sensor, a cleaning device such as a sprayer, scrubber, and/or scraper, a marking device, and/or a repair device. The front-back arrangement of payloads 2 provides for adjustments, cleaning, repair, and/or marking of the inspection surface 502 in a single run—for example where an anomaly, gouge, weld line, area for repair, previously repaired area, past inspection area, etc., is sensed by the front payload 2, the anomaly can be marked, cleaned, repaired, etc. without requiring an additional run of the inspection robot 100 or a later visit by repair personnel. In another example, a first calibration of sensors for the front payload may be determined to be incorrect (e.g., a front ultra-sonic sensor calibrated for a particular coating thickness present on the pipes 502) and a rear sensor can include an adjusted calibration to account for the detected aspect (e.g., the rear sensor calibrated for the observed thickness of the coating). In another example, certain enhanced sensing operations may be expensive, time consuming, consume more resources (e.g., a gamma ray source, an alternate coupling such as a non-water or oil-based acoustic coupler, require a high energy usage, require greater processing resources, and/or incur usage charges to an inspection client for any reason) and the inspection robot 100 can thereby only utilize the enhanced sensing operations selectively and in response to observed conditions.

Figure 7:
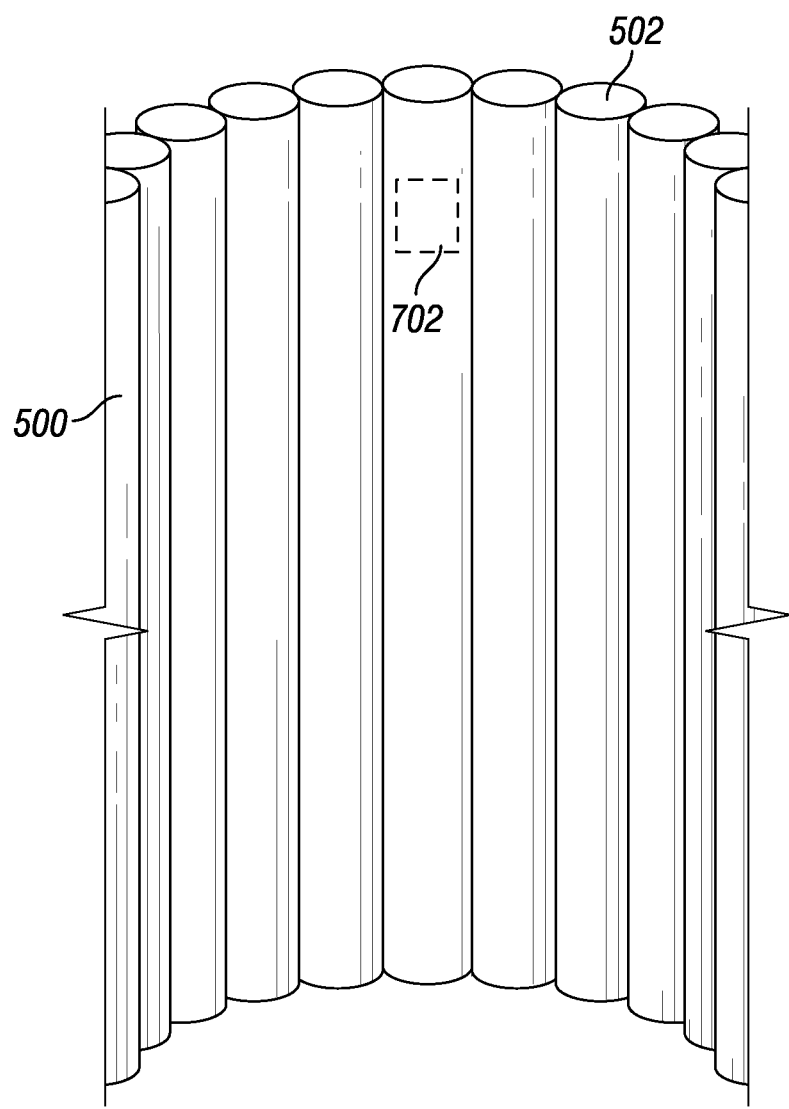
FIG. 7 is a schematic depiction of a location on an inspection surface.

Referencing FIG. 7, a location 702 on the inspection surface 500 is identified for illustration. In certain embodiments, the inspection robot 100 and/or apparatus 800 includes a controller 802 having a number of circuits structured to functionally execute operations of the controller 802. The controller 802 may be a single device (e.g., a computing device present on the robot 100, a computing device in communication with the robot 100 during operations and/or post-processing information communicated after inspection operations, etc.) and/or a combination of devices, such as a portion of the controller 802 positioned on the robot 100, a portion of the controller 802 positioned on a computing device in communication with the robot 100, a portion of the controller 802 positioned on a handheld device (not shown) of an inspection operator, and/or a portion of the controller 802 positioned on a computing device networked with one or more of the preceding devices. Additionally or alternatively, aspects of the controller 802 may be included on one or more logic circuits, embedded controllers, hardware configured to perform certain aspects of the controller 802 operations, one or more sensors, actuators, network communication infrastructure (including wired connections, wireless connections, routers, switches, hubs, transmitters, and/or receivers), and/or a tether between the robot 100 and another computing device. The described aspects of the example controller 802 are non-limiting examples, and any configuration of the robot 100 and devices in communication with the robot 100 to perform all or selected ones of operations of the controller 802 are contemplated herein as aspects of an example controller 802.

An example controller 802 includes an inspection data circuit 804 that interprets inspection data 812—for example sensed information from sensors mounted on the payload and determining aspects of the inspection surface 500, the status, deployment, and/or control of marking devices, cleaning devices, and/or repair devices, and/or post-processed information from any of these such as a wall thickness determined from ultra-sonic data, temperature information determined from imaging data, and the like. The example controller 802 further includes a robot positioning circuit 806 that interprets position data 814. An example robot positioning circuit 806 determines position data by any available method, including at least triangulating (or other positioning methods) from a number of available wireless devices (e.g., routers available in the area of the inspection surface 500, intentionally positioned transmitters/transceivers, etc.), a distance of travel measurement (e.g., a wheel rotation counter which may be mechanical, electro-magnetic, visual, etc.; a barometric pressure measurement; direct visual determinations such as radar, Lidar, or the like), a reference measurement (e.g., determined from distance to one or more reference points); a time-based measurement (e.g., based upon time and travel speed); and/or a dead reckoning measurement such as integration of detection movements. In the example of FIG. 5, a position measurement may include a height determination combined with an azimuthal angle measurement and/or a pipe number value such that the inspection surface 500 location is defined thereby. Any coordinate system and/or position description system is contemplated herein. In certain embodiments, the controller 802 includes a processed data circuit 808 that combines the inspection data 812 with the position data 814 to determine position-based inspection data. The operations of the processed data circuit 808 may be performed at any time—for example during operations of the inspection robot 100 such that inspection data 812 is stored with position data 814, during a post-processing operation which may be completed separately from the inspection robot 100, and/or which may be performed after the inspection is completed, and/or which may be commenced while the inspection is being performed. In certain embodiments, the linking of the position data 814 with the inspection data 812 may be performed if the linked position-inspection data is requested—for example upon a request by a client for an inspection map 818. In certain embodiments, portions of the inspection data 812 are linked to the position data 814 at a first time, and other portions of the inspection data 812 are linked to the position data 814 at a later time and/or in response to post-processing operations, an inspection map 818 request, or other subsequent event.

The example controller 802 further includes an inspection visualization circuit 810 that determines the inspection map 818 in response to the inspection data 812 and the position data 814, for example using post-processed information from the processed data circuit 808. In a further example, the inspection visualization circuit 810 determines the inspection map 818 in response to an inspection visualization request 820, for example from a client computing device 826. In the example, the client computing device 826 may be communicatively coupled to the controller 802 over the internet, a network, through the operations of a web application, and the like. In certain embodiments, the client computing device 826 securely logs in to control access to the inspection map 818, and the inspection visualization circuit 810 may prevent access to the inspection map 818, and/or provide only portions of the inspection map 818, depending upon the successful login from the client computing device 826, the authorizations for a given user of the client computing device 826, and the like.

In certain embodiments, the inspection visualization circuit 810 and/or inspection data circuit 804 further accesses system data 816, such as a time of the inspection, a calendar date of the inspection, the robot 100 utilized during the inspection and/or the configurations of the robot 100, a software version utilized during the inspection, calibration and/or sensor processing options selected during the inspection, and/or any other data that may be of interest in characterizing the inspection, that may be requested by a client, that may be required by a policy and/or regulation, and/or that may be utilized for improvement to subsequent inspections on the same inspection surface 500 or another inspection surface. In certain embodiments, the processed data circuit 808 combines the system data 816 with the processed data for the inspection data 812 and/or the position data 814, and/or the inspection visualization circuit incorporates the system data 816 or portions thereof into the inspection map 818. In certain embodiments, any or all aspects of the inspection data 812, position data 814, and/or system data 816 may be stored as meta-data (e.g., not typically available for display), may be accessible in response to prompts, further selections, and/or requests from the client computing device 826, and/or may be utilized in certain operations with certain identifiable aspects removed (e.g., to remove personally identifiable information or confidential aspects) such as post-processing to improve future inspection operations, reporting for marketing or other purposes, or the like.

In certain embodiments, the inspection visualization circuit 810 is further responsive to a user focus value 822 to update the inspection map 818 and/or to provide further information (e.g., focus data 824) to a user, such as a user of the client computing device 826. For example, a user focus value 822 (e.g., a user mouse position, menu selection, touch screen indication, keystroke, or other user input value indicating that a portion of the inspection map 818 has received the user focus) indicates that a location 702 of the inspection map 818 has the user focus, and the inspection visualization circuit 810 generates the focus data 824 in response to the user focus value 822, including potentially the location 702 indicated by the user focus value 822.

Figure 9:
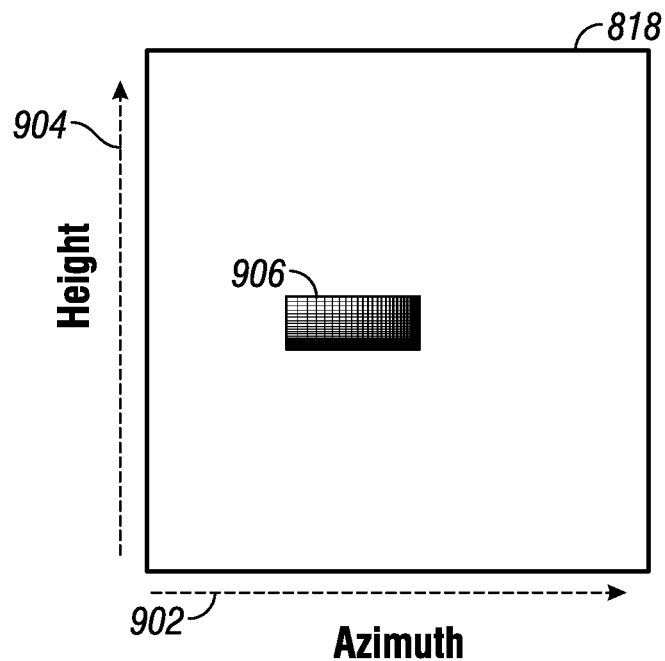
FIG. 9 depicts an illustrative inspection map.

Referencing FIG. 9, an example inspection map 818 is depicted. In the example, the inspection surface 500 may be similar to that depicted in FIG. 5—for example the interior surface of tower formed by a number of pipes to be inspected. The example inspection map 818 includes an azimuthal indication 902 and a height indication 904, with data from the inspection depicted on the inspection map 818 (e.g., shading at 906 indicating inspection data corresponding to that visual location). Example and non-limiting inspection maps 818 include numeric values depicted on the visualization, colors, shading or hatching, and/or any other visual depiction method. In certain embodiments, more than one inspection dimension may be visualized (e.g., temperatures and wall thickness), and/or the inspection dimension may be selected or changed by the user. Additionally or alternatively, physical elements such as obstacles, build up on the inspection surface, weld lines, gouges, repaired sections, photos of the location (e.g., the inspection map 818 laid out over a panoramic photograph of the inspection surface 500 with data corresponding to the physical location depicted), may be depicted with or as a part of the inspection map 818. Additionally or alternatively, visual markers may be positioned on the inspection map 818—for example a red "X" (or any other symbol, including a color, bolded area, highlight, image data, a thumbnail, etc.) at a location of interest on the map—which marking may be physically present on the actual inspection surface 500 or only virtually depicted on the inspection map 818. It can be seen that the inspection map 818 provides for a convenient and powerful reference tool for a user to determine the results of the inspection operation and plan for future maintenance, repair, or inspections, as well as planning logistics in response to the number of aspects of the system requiring further work or analysis and the location of the aspects requiring further work or analysis. Accordingly, inspection results can be analyzed more quickly, regulatory or policy approvals and system up-time can be restored more quickly (if the system was shut-down for the inspection), configurations of an inspection robot 100 for a future inspection can be performed more quickly (e.g. preparing payload 2 configurations, obstacle management, and/or sensor selection or calibration), any of the foregoing can be performed with greater confidence that the results are reliable, and/or any combinations of the foregoing. Additionally or alternatively, less invasive operations can be performed, such as virtual marking which would not leave marks on the inspection surface 500 that might be removed (e.g., accidentally) before they are acted upon, which may remain after being acted upon, or which may create uncertainty as to when the marks were made over the course of multiple inspections and marking generations.

Figure 10:
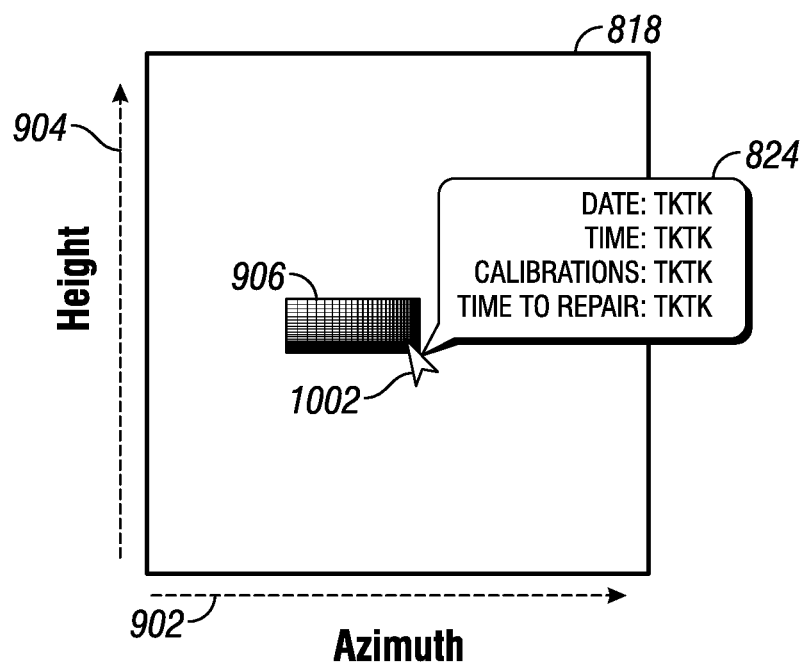
FIG. 10 depicts an illustrative inspection map and focus data.

Referencing FIG. 10, an illustrative example inspection map 818 having focus data 824 is depicted. The example inspection map 818 is responsive to a user focus value 822, such as a mouse cursor 1002 hovering over a portion of the inspection map 818. In the example, the focus data 824 comes up as a tool-tip, although any depiction operations such as output to a file, populating a static window for focus data 824, or any other operations known in the art are contemplated herein. The example focus data 824 includes a date (e.g., of the inspection), a time (e.g., of the inspection), the sensor calibrations utilized for the inspection, and the time to repair (e.g., down-time that would be required, actual repair time that would be required, the estimated time until the portion of the inspection surface 500 will require a repair, or any other description of a "time to repair"). The depicted focus data 824 is a non-limiting example, and any other information of interest may be utilized as focus data 824. In certain embodiments, a user may select the information, or portions thereof, utilized on the inspection map 818—including at least the axes 902, 904 (e.g., units, type of information, relative versus absolute data, etc.) and the depicted data (e.g., units, values depicted, relative versus absolute values, thresholds or cutoffs of interest, processed values such as virtually determined parameters, and/or categorical values such as "PASSED" or "FAILED"). Additionally or alternatively, a user may select the information, or portions thereof, utilized as the focus data 824.

In certain embodiments, an inspection map 818 (or display) provides an indication of how long a section of the inspection surface 500 is expected to continue under nominal operations, how much material should be added to a section of the inspection surface 500 (e.g., a repair coating or other material), and/or the type of repair that is needed (e.g., wall thickness correction, replacement of a coating, fixing a hole, breach, rupture, etc.).

Figure 41:
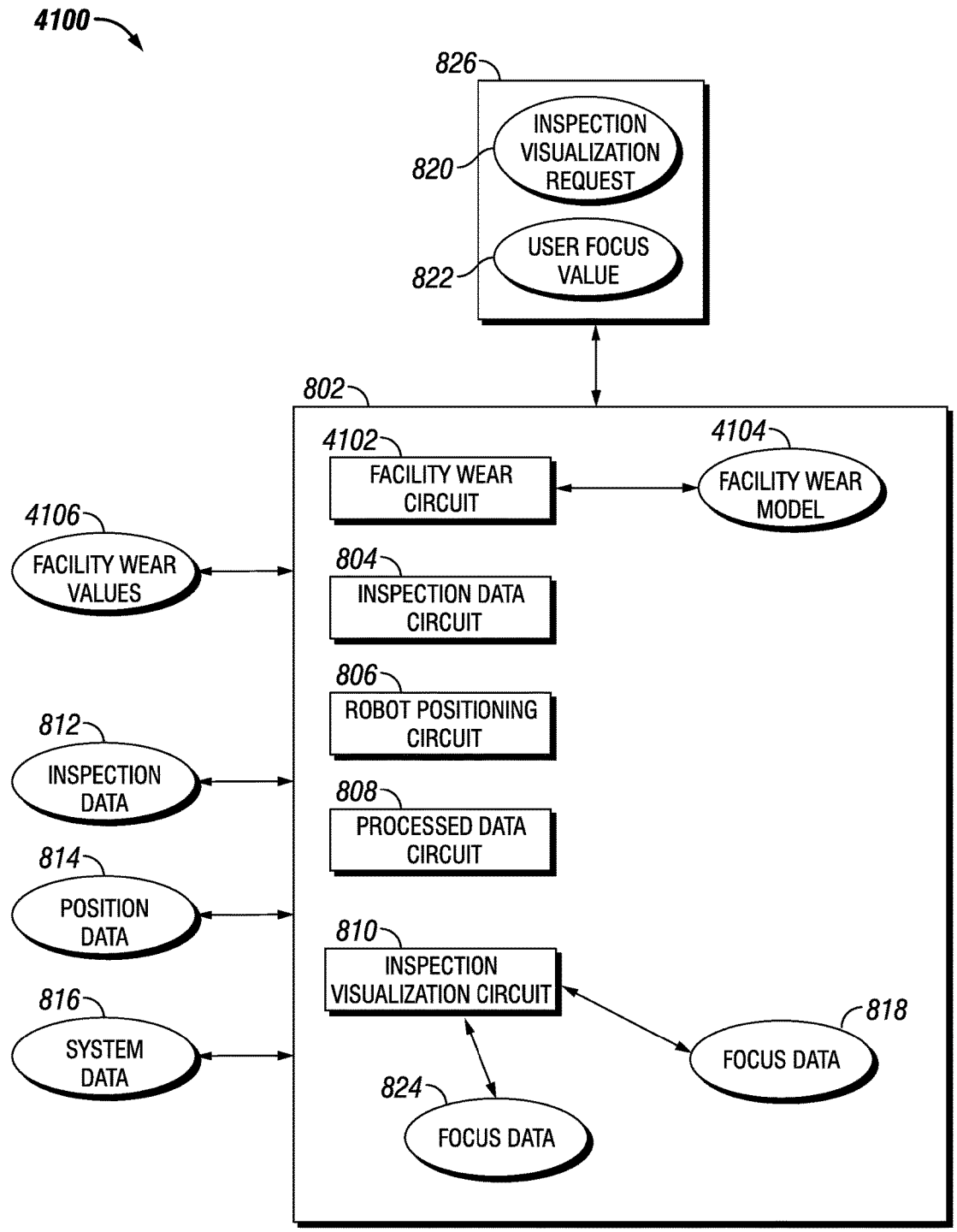
FIG. 41 is a schematic block diagram of an apparatus for providing a facility wear value.

Referencing FIG. 41, an apparatus 4100 for determining a facility wear value 4106 is depicted. The example apparatus 4100 includes a facility wear circuit 4102 that determines a facility wear model 4104 corresponding to the inspection surface 500 and/or an industrial facility, industrial system, and/or plant including the inspection surface 500. An example facility wear circuit 4102 accesses a facility wear model 4104, and utilizes the inspection data 812 to determine which portions of the inspection surface 500 will require repair, when they will require repair, what type of repair will be required, and a facility wear value 4106 including a description of how long the inspection surface 500 will last without repair, and/or with selected repairs. In certain embodiments, the facility wear model 4104 includes historical data for the particular facility, system, or plant having the inspection surface 500—for example through empirical observation of previous inspection data 812, when repairs were performed, what types of repairs were performed, and/or how long repaired sections lasted after repairs.

Additionally or alternatively, the facility wear model 4104 includes data from offset facilities, systems, or plants (e.g., a similar system that operates a similar duty cycle of relevant temperatures, materials, process flow streams, vibration environment, etc. for the inspection surface 500; and which may include inspection data, repair data, and/or operational data from the offset system), canonical data (e.g., pre-entered data based on estimates, modeling, industry standards, or other indirect sources), data from other facilities from the same data client (e.g., an operator, original equipment manufacturer, owner, etc. for the inspection surface), and/or user-entered data (e.g., from an inspection operator and/or client of the data) such as assumptions to be utilized, rates of return for financial parameters, policies or regulatory values, and/or characterizations of experience in similar systems that may be understood based on the experience of the user. Accordingly, operations of the facility wear circuit 4102 can provide an overview of repair operations recommended for the inspection surface 500, including specific time frame estimates of when such repairs will be required, as well as a number of options for repair operations and how long they will last.

In certain embodiments, the facility wear value 4106, and/or facility wear value 4106 displayed on an inspection map 818, allows for strategic planning of repair operations, and/or coordinating the life cycle of the facility including the inspection surface 500—for example performing a short-term repair at a given time, which might not be intuitively the "best" repair operation, but in view of a larger repair cycle that is upcoming for the facility. Additionally or alternatively, we facility wear value 4106 allows for a granular review of the inspection surface 500—for example to understand operational conditions that drive high wear, degradation, and/or failure conditions of aspects of the inspection surface 500. In certain embodiments, repair data and/or the facility wear value 4106 are provided in a context distinct from an inspection map 818—for example as part of an inspection report (not shown), as part of a financial output related to the system having the inspection surface (e.g., considering the costs and shutdown times implicated by repairs, and/or risks associated with foregoing a repair).

Figure 42:
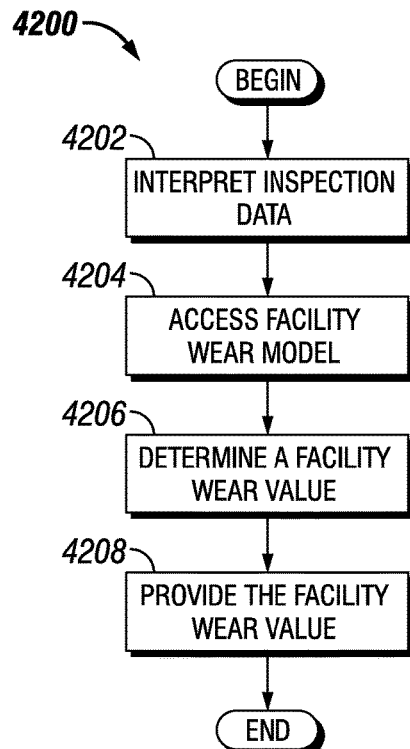
FIG. 42 is a schematic flow diagram of a procedure to provide a facility wear value.

Referencing FIG. 42, a procedure 4200 for determining a facility wear value is depicted schematically. An example procedure 4200 includes an operation 4202 to interpret inspection data for an inspection surface, and an operation 4204 to access a facility wear model. The example procedure 4200 further includes an operation 4206 to determine a facility wear value in response to the inspection data and the facility wear model. The example procedure 4200 further includes an operation 4208 to provide the facility wear value—for example as a portion of an inspection map, an inspection report, and/or a financial report for a facility having the inspection surface.

In embodiments, the robotic vehicle may incorporate a number of sensors distributed across a number of sensor sleds 1, such as with a single sensor mounted on a single sensor sled 1, a number of sensors mounted on a single sensor sled 1, a number of sensor sleds 1 arranged in a linear configuration perpendicular to the direction of motion (e.g., side-to-side across the robotic vehicle), arranged in a linear configuration along the direction of motion (e.g., multiple sensors on a sensor sled 1 or multiple sensor sleds 1 arranged to cover the same surface location one after the other as the robotic vehicle travels). Additionally or alternatively, a number of sensors may be arranged in a two-dimensional surface area, such as by providing sensor coverage in a distributed manner horizontally and/or vertically (e.g., in the direction of travel), including offset sensor positions (e.g., reference FIG. 14). In certain embodiments, the utilization of payloads 2 with sensor sleds mounted thereon enables rapid configuration of sensor placement as desired, sleds 1 on a given payload 2 can be further adjusted, and/or sensor(s) on a given sled can be changed or configured as desired.

In certain embodiments, two payloads 2 side-by-side allow for a wide horizontal coverage of sensing for a given travel of the inspection robot 100—for example as depicted in FIG. 1. In certain embodiments, a payload 2 is coupled to the inspection robot 100 with a pin or other quick-disconnect arrangement, allowing for the payload 2 to be removed, to be reconfigured separately from the inspection robot 100, and/or to be replaced with another payload 2 configured in a desired manner. The payload 2 may additionally have a couplant connection to the inspection robot 100 (e.g., reference FIG. 29—where a single couplant connection provides coupling connectivity to all sleds 1A and 1B) and/or an electrical connection to the inspection robot 100. Each sled may include a couplant connection conduit where the couplant connection conduit is coupled to a payload couplant connection at the upstream end and is coupled to the couplant entry of the cone at the downstream end. Multiple payload couplant connections on a single payload may be coupled together to form a single couplant connection between the payload and the inspection robot. The single couplant connection per payload facilitates the changing of the payload without having to connect/disconnect the couplant line connections at each sled. The couplant connection conduit between the payload couplant connection and the couplant entry of the cone facilitates connecting/disconnecting a sled from a payload without having to connect/disconnect the couplant connection conduit from the couplant entry of the cone. The couplant and/or electrical connections may include power for the sensors as required, and/or communication coupling (e.g., a datalink or network connection). Additionally or alternatively, sensors may communicate wirelessly to the inspection robot 100 or to another computing device, and/or sensors may store data in a memory associated with the sensor, sled 1, or payload 2, which may be downloaded at a later time. Any other connection type required for a payload 2, such as compressed air, paint, cleaning solutions, repair spray solutions, or the like, may similarly be coupled from the payload 2 to the inspection robot 100.

The horizontal configuration of sleds 1 (and sensors) is selectable to achieve the desired inspection coverage. For example, sleds 1 may be positioned to provide a sled running on each of a selected number of pipes of an inspection surface, positioned such that several sleds 1 combine on a single pipe of an inspection surface (e.g., providing greater radial inspection resolution for the pipe), and/or at selected horizontal distances from each other (e.g., to provide 1 inch resolution, 2 inch resolution, 3 inch resolution, etc.). In certain embodiments, the degrees of freedom of the sensor sleds 1 (e.g., from pivots 16, 17, 18) allow for distributed sleds 1 to maintain contact and orientation with complex surfaces.

In certain embodiments, sleds 1 are articulable to a desired horizontal position. For example, quick disconnects may be provided (pins, claims, set screws, etc.) that allow for the sliding of a sled 1 to any desired location on a payload 2, allowing for any desired horizontal positioning of the sleds 1 on the payload 2. Additionally or alternatively, sleds 1 may be movable horizontally during inspection operations. For example, a worm gear or other actuator may be coupled to the sled 1 and operable (e.g., by a controller 802) to position the sled 1 at a desired horizontal location. In certain embodiments, only certain ones of the sleds 1 are moveable during inspection operations—for example outer sleds 1 for maneuvering past obstacles. In certain embodiments, all of the sleds 1 are moveable during inspection operations—for example to support arbitrary inspection resolution (e.g., horizontal resolution, and/or vertical resolution), to configure the inspection trajectory of the inspection surface, or for any other reason. In certain embodiments, the payload 2 is horizontally moveable before or during inspection operations. In certain embodiments, an operator configures the payload 2 and/or sled 1 horizontal positions before inspection operations (e.g., before or between inspection runs). In certain embodiments, an operator or a controller 802 configures the payload 2 and/or sled 1 horizontal positions during inspection operations. In certain embodiments, an operator can configure the payload 2 and/or sled 1 horizontal positions remotely, for example communicating through a tether or wirelessly to the inspection robot.

The vertical configuration of sleds 1 is selectable to achieve the desired inspection coverage (e.g., horizontal resolution, vertical resolution, and/or redundancy). For example, referencing FIG. 13, multiple payloads 2 are positioned on a front side of the inspection robot 100, with forward payloads 2006 and rear payloads 1402. In certain embodiments, a payload 2 may include a forward payload 2006 and a rear payload 1402 in a single hardware device (e.g., with a single mounting position to the inspection robot 100), and/or may be independent payloads 2 (e.g., with a bracket extending from the inspection robot 100 past the rear payload 1402 for mounting the forward payloads 2006). In the example of FIG. 13, the rear payload 1402 and front payload 2006 include sleds 1 mounted thereupon which are in vertical alignment 1302—for example a given sled 1 of the rear payload 1402 traverses the same inspection position (or horizontal lane) of a corresponding sled 1 of the forward payload 2006. The utilization of aligned payloads 2 provides for a number of capabilities for the inspection robot 100, including at least: redundancy of sensing values (e.g., to develop higher confidence in a sensed value); the utilization of more than one sensing calibration for the sensors (e.g., a front sensor utilizes a first calibration set, and a rear sensor utilizes a second calibration set); the adjustment of sensing operations for a rear sensor relative to a forward sensor (e.g., based on the front sensed parameter, a rear sensor can operate at an adjusted range, resolution, sampling rate, or calibration); the utilization of a rear sensor in response to a front sensor detected value (e.g., a rear sensor may be a high cost sensor—either high power, high computing/processing requirements, an expensive sensor to operate, etc.) where the utilization of the rear sensor can be conserved until a front sensor indicates that a value of interest is detected; the operation of a repair, marking, cleaning, or other capability rear payload 1402 that is responsive to the detected values of the forward payload 2006; and/or for improved vertical resolution of the sensed values (e.g., if the sensor has a given resolution of detection in the vertical direction, the front and rear payloads can be operated out of phase to provide for improved vertical resolution).

Figure 14:
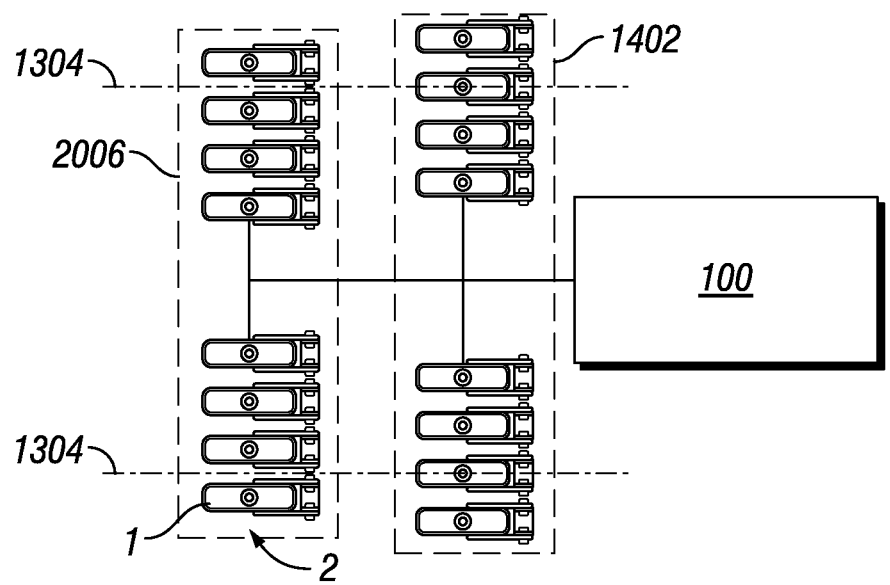
FIG. 14 is another schematic diagram of a payload arrangement.

In another example, referencing FIG. 14, multiple payloads 2 are positioned on the front of the inspection robot 100, with sleds 1 mounted on the front payload 2006 and rear payload 1402 that are not aligned (e.g., lane 1304 is not shared between sleds of the front payload 2006 and rear payload 2002). The utilization of not aligned payloads 2 allows for improved resolution in the horizontal direction for a given number of sleds 1 mounted on each payload 2. In certain embodiments, not aligned payloads may be utilized where the hardware space on a payload 2 is not sufficient to conveniently provide a sufficient number or spacing of sleds 1 to achieve the desired horizontal coverage. In certain embodiments, not aligned payloads may be utilized to limit the number of sleds 1 on a given payload 2, for example to provide for a reduced flow rate of couplant through a given payload-inspection robot connection, to provide for a reduced load on an electrical coupling (e.g., power supply and/or network communication load) between a given payload and the inspection robot. While the examples of FIGS. 13 and 14 depict aligned or not aligned sleds for convenience of illustration, a given inspection robot 100 may be configured with both aligned and not aligned sleds 1, for example to reduce mechanical loads, improve inspection robot balance, in response to inspection surface constraints, or the like.

It can be seen that sensors may be modularly configured on the robotic vehicle to collect data on specific locations across the surface of travel (e.g., on a top surface of an object, on the side of an object, between objects, and the like), repeat collection of data on the same surface location (e.g., two sensors serially collecting data from the same location, either with the same sensor type or different sensor types), provide predictive sensing from a first sensor to determine if a second sensor should take data on the same location at a second time during a single run of the robotic vehicle (e.g., an ultra-sonic sensor mounted on a leading sensor sled taking data on a location determines that a gamma-ray measurement should be taken for the same location by a sensor mounted on a trailing sensor sled configured to travel over the same location as the leading sensor), provide redundant sensor measurements from a plurality of sensors located in leading and trailing locations (e.g., located on the same or different sensor sleds to repeat sensor data collection), and the like.

In certain embodiments, the robotic vehicle includes sensor sleds with one sensor and sensor sleds with a plurality of sensors. A number of sensors arranged on a single sensor sled may be arranged with the same sensor type across the direction of robotic vehicle travel (e.g., perpendicular to the direction of travel, or "horizontal") to increase coverage of that sensor type (e.g., to cover different surfaces of an object, such as two sides of a pipe), arranged with the same sensor type along the direction of robotic vehicle travel (e.g., parallel to the direction of travel, or "vertical") to provide redundant coverage of that sensor type over the same location (e.g., to ensure data coverage, to enable statistical analysis based on multiple measurements over the same location), arranged with a different sensor type across the direction of robotic vehicle travel to capture a diversity of sensor data in side-by-side locations along the direction of robotic vehicle travel (e.g., providing both ultra-sonic and conductivity measurements at side-by-side locations), arranged with a different sensor type along the direction of robotic vehicle travel to provide predictive sensing from a leading sensor to a trailing sensor (e.g., running a trailing gamma-ray sensor measurement only if a leading ultra-sonic sensor measurement indicates the need to do so), combinations of any of these, and the like. The modularity of the robotic vehicle may permit exchanging sensor sleds with the same sensor configuration (e.g., replacement due to wear or failure), different sensor configurations (e.g., adapting the sensor arrangement for different surface applications), and the like.

Providing for multiple simultaneous sensor measurements over a surface area, whether for taking data from the same sensor type or from different sensor types, provides the ability to maximize the collection of sensor data in a single run of the robotic vehicle. If the surface over which the robotic vehicle was moving were perfectly flat, the sensor sled could cover a substantial surface with an array of sensors. However, the surface over which the robotic vehicle travels may be highly irregular, and have obstacles over which the sensor sleds must adjust, and so the preferred embodiment for the sensor sled is relatively small with a highly flexible orientation, as described herein, where a plurality of sensor sleds is arranged to cover an area along the direction of robotic vehicle travel. Sensors may be distributed amongst the sensor sleds as described for individual sensor sleds (e.g., single sensor per sensor sled, multiple sensors per sensor sled (arranged as described herein)), where total coverage is achieved through a plurality of sensor sleds mounted to the robotic vehicle. One such embodiment, as introduced herein, such as depicted in FIG. 1, comprises a plurality of sensor sleds arranged linearly across the direction of robotic vehicle travel, where the plurality of sensor sleds are capable of individually adjusting to the irregular surface as the robotic vehicle travels. Further, each sensor sled may be positioned to accommodate regular characteristics in the surface (e.g., positioning sensor sleds to ride along a selected portion of a pipe aligned along the direction of travel), to provide for multiple detections of a pipe or tube from a number of radial positions, sensor sleds may be shaped to accommodate the shape of regular characteristics in the surface (e.g., rounded surface of a pipe), and the like. In this way, the sensor sled arrangement may accommodate both the regular characteristics in the surface (e.g., a series of features along the direction of travel) and irregular characteristics along the surface (e.g., obstacles that the sensor sleds flexibly mitigate during travel along the surface).

Although FIG. 1 depicts a linear arrangement of sensor sleds with the same extension (e.g., the same connector arm length), another example arrangement may include sensor sleds with different extensions, such as where some sensor sleds are arranged to be positioned further out, mounted on longer connection arms. This arrangement may have the advantage of allowing a greater density of sensors across the configuration, such as where a more leading sensor sled could be positioned linearly along the configuration between two more trailing sensor sleds such that sensors are provided greater linear coverage than would be possible with all the sensor sleds positioned side-by-side. This configuration may also allow improved mechanical accommodation between the springs and connectors that may be associated with connections of sensor sleds to the arms and connection assembly (e.g., allowing greater individual movement of sensor sleds without the sensor sleds making physical contact with one another).

Figure 15:
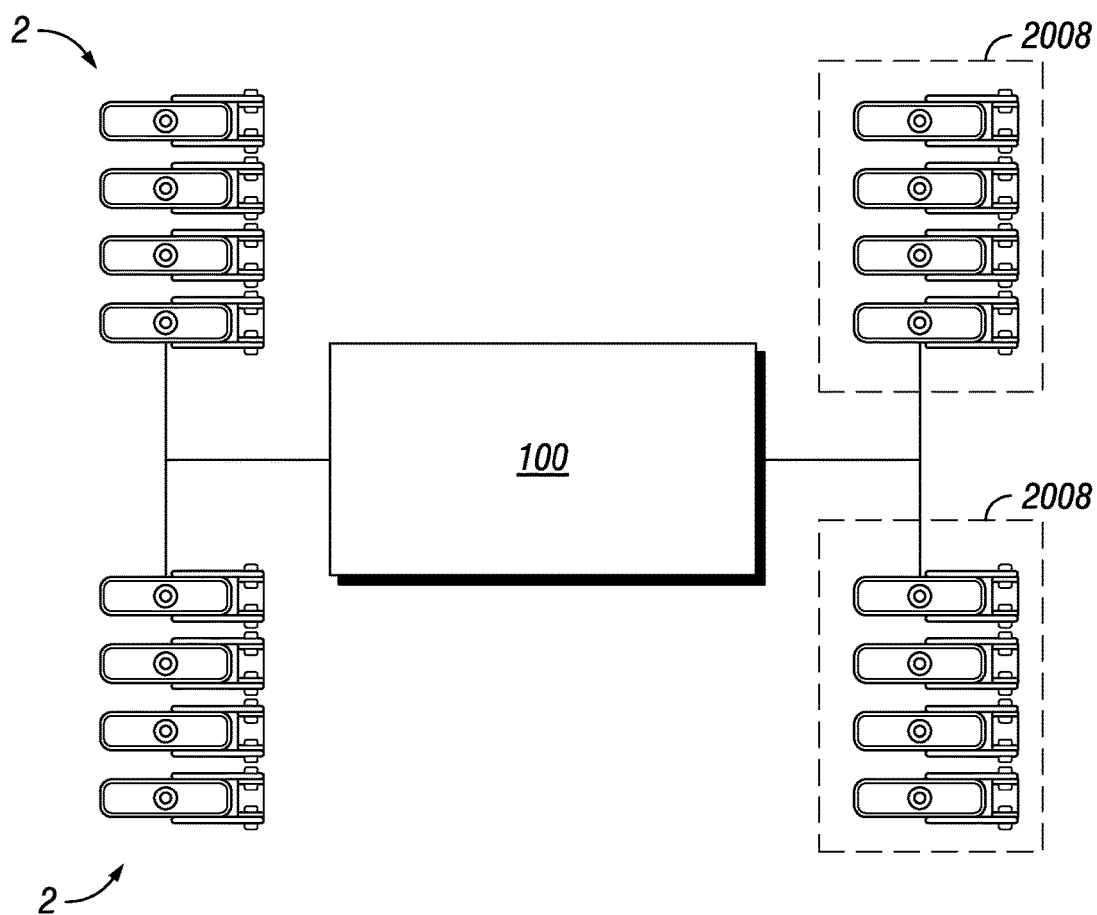
FIG. 15 is another schematic diagram of a payload arrangement.

Referring to FIG. 13, an example configuration of sensor sleds includes the forward sensor sled array 2006 ahead of the rear sled array 1402, such as where each utilizes a sensor sled connector assembly 2004 for mounting the payloads. Again, although FIG. 13 depicts the sensor sleds arranged on the sensor sled connector assembly 2004 with equal length arms, different length arms may be utilized to position, for instance, sensor sleds of sensor sled array 1402 in intermediate positions between rear sensor sleds of rear payload 1402 and forward sensor sleds of the forward payload 2006. As was the case with the arrangement of a plurality of sensors on a single sensor sled to accommodate different coverage options (e.g., maximizing coverage, predictive capabilities, redundancy, and the like), the extended area configuration of sensors in this multiple sensor sled array arrangement allows similar functionality. For instance, a sensor sled positioned in a lateral position on the forward payload 2006 may provide redundant or predictive functionality for another sensor sled positioned in the same lateral position on the rear payload 1402. In the case of a predictive functionality, the greater travel distance afforded by the separation between a sensor sled mounted on the second sensor sled array 2006 and the sensor sled array 1402 may provide for additional processing time for determining, for instance, whether the sensor in the trailing sensor sled should be activated. For example, the leading sensor collects sensor data and sends that data to a processing function (e.g., wired communication to on-board or external processing, wireless communication to external processing), the processor takes a period of time to determine if the trailing sensor should be activated, and after the determination is made, activates the trailing sensor. The separation of the two sensors, divided by the rate of travel of the robotic vehicle, determines the time available for processing. The greater the distance, the greater the processing time allowed. Referring to FIG. 15, in another example, distance is increased further by utilizing a trailing payload 2008, thus increasing the distance and processing time further. Additionally or alternatively, the hardware arrangement of FIG. 15 may provide for more convenient integration of the trailing payload 2008 rather than having multiple payloads 1402, 2006 in front of the inspection robot 100. In certain embodiments, certain operations of a payload 2 may be easier or more desirable to perform on a trailing side of the inspection robot 100—such as spraying of painting, marking, or repair fluids, to avoid the inspection robot 100 having to be exposed to such fluids as a remaining mist, by gravity flow, and/or having to drive through the painted, cleaned, or repaired area. In certain embodiments, an inspection robot 100 may additionally or alternatively include both multiple payloads 1402, 2006 in front of the inspection robot (e.g., as depicted in FIGS. 13 and 14) and/or one or more trailing payloads (e.g., as depicted in FIG. 15).

In another example, the trailing sensor sled array 2008 may provide a greater distance for functions that would benefit the system by being isolated from the sensors in the forward end of the robotic vehicle. For instance, the robotic vehicle may provide for a marking device (e.g., visible marker, UV marker, and the like) to mark the surface when a condition alert is detected (e.g., detecting corrosion or erosion in a pipe at a level exceeding a predefined threshold, and marking the pipe with visible paint).

Embodiments with multiple sensor sled connector assemblies provide configurations and area distribution of sensors that may enable greater flexibility in sensor data taking and processing, including alignment of same-type sensor sleds allowing for repeated measurements (e.g., the same sensor used in a leading sensor sled as in a trailing sensor sled, such as for redundancy or verification in data taking when leading and trailing sleds are co-aligned), alignment of different-type sensor sleds for multiple different sensor measurements of the same path (e.g., increase the number of sensor types taking data, have the lead sensor provide data to the processor to determine whether to activate the trailing sensor (e.g., ultra-sonic/gamma-ray, and the like)), off-set alignment of same-type sensor sleds for increased coverage when leading and trailing sleds are off-set from one another with respect to travel path, off-set alignment of different-type sensor sleds for trailing sensor sleds to measure surfaces that have not been disturbed by leading sensor sleds (e.g., when the leading sensor sled is using a couplant), and the like.

The modular design of the robotic vehicle may provide for a system flexible to different applications and surfaces (e.g., customizing the robot and modules of the robot ahead of time based on the application, and/or during an inspection operation), and to changing operational conditions (e.g., flexibility to changes in surface configurations and conditions, replacement for failures, reconfiguration based on sensed conditions), such as being able to change out sensors, sleds, assemblies of sleds, number of sled arrays, and the like.

Figure 12:
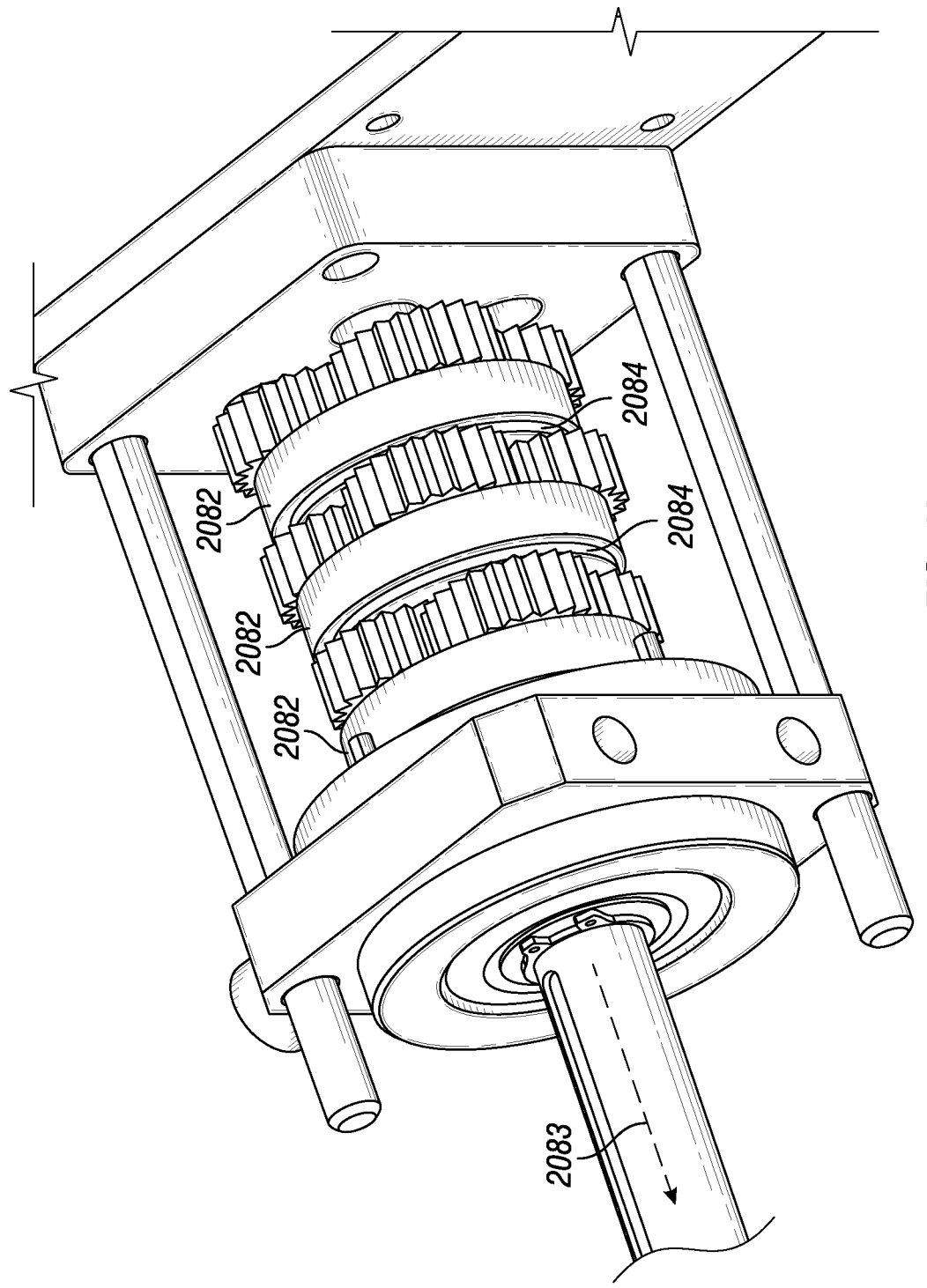
FIG. 12 is a schematic depiction of a gearbox.

An example inspection robot utilizes a magnet-based wheel design (e.g., reference FIG. 2 and the related description). Although the inspection robot may utilize flux directing ferromagnetic wheel components, such as ferromagnetic magnet enclosures 3 to minimize the strength of the extended magnetic field, ferromagnetic components within the inspection robot may be exposed to a magnetic field. One component that may experience negative effects from the magnetic field is the gearbox, which may be mounted proximate to the wheel assembly. FIG. 12 illustrates an example gearbox configuration, showing the direction 2083 of magnetic attraction axially along the drive shaft to the wheel (wheel not shown). The magnetic attraction, acting on, in this instance, ferromagnetic gears, results in an axial load applied to the gears, pulling the gears against the gear carrier plates 2082 with forces that the gears would otherwise not experience. This axial load may result in increased friction, heat, energy loss, and wear.

Referencing FIG. 12, an example arrangement depicts the inclusion of wear-resistant thrust washers 2084, placed to provide a reduced frictional interface between the gears and the adjacent surface. Thus, the negative effects of the axial load are minimized without significant changes to a gearbox design. In a second example, with wheels on opposing sides of the gear box assembly(s), the gearbox configuration of the inspection robot may be spatially arranged such that the net magnetic forces acting on the gears are largely nullified, that is, balanced between forces from a wheel magnet on one side and a second wheel magnet on the other side. Careful layout of the gearbox configuration could thus reduce the net forces acting on the gears. In embodiments, example one and example two may be applied alone or in combination. For instance, the gearbox configuration may be spatially arranged to minimize the net magnetic forces acting on gears, where thrust washers are applied to further reduce the negative effects of any remaining net magnetic forces. In a third example, the negative effects upon the gearbox resulting from magnetic fields may be eliminated by making the gears from non-ferrous materials. Example and non-limiting examples of non-ferrous materials include polyoxymethylene (e.g., Delrin® acetyl resin, etc.), a low- or non-magnetic steel (e.g. 316 stainless steel or 304 stainless steel), and/or aluminum (e.g., 2024 Al). In certain embodiments, other materials such as ceramic, nylon, copper, or brass may be used for gears, depending upon the wear and load requirements of the gearbox, the potential intrusion of water to the gearbox, and/or the acceptable manufacturing costs and tolerances.

Throughout the present description, certain orientation parameters are described as "horizontal," "perpendicular," and/or "across" the direction of travel of the inspection robot, and/or described as "vertical," "parallel," and/or in line with the direction of travel of the inspection robot. It is specifically contemplated herein that the inspection robot may be travelling vertically, horizontally, at oblique angles, and/or on curves relative to a ground-based absolute coordinate system. Accordingly, except where the context otherwise requires, any reference to the direction of travel of the inspection robot is understood to include any orientation of the robot—such as an inspection robot traveling horizontally on a floor may have a "vertical" direction for purposes of understanding sled distribution that is in a "horizontal" absolute direction. Additionally, the "vertical" direction of the inspection robot may be a function of time during inspection operations and/or position on an inspection surface—for example as an inspection robot traverses over a curved surface. In certain embodiments, where gravitational considerations or other context based aspects may indicate—vertical indicates an absolute coordinate system vertical—for example in certain embodiments where couplant flow into a cone is utilized to manage bubble formation in the cone. In certain embodiments, a trajectory through the inspection surface of a given sled may be referenced as a "horizontal inspection lane"—for example, the track that the sled takes traversing through the inspection surface.

Certain embodiments include an apparatus for acoustic inspection of an inspection surface with arbitrary resolution. Arbitrary resolution, as utilized herein, includes resolution of features in geometric space with a selected resolution—for example resolution of features (e.g., cracks, wall thickness, anomalies, etc.) at a selected spacing in horizontal space (e.g., perpendicular to a travel direction of an inspection robot) and/or vertical space (e.g., in a travel direction of an inspection robot). While resolution is described in terms of the travel motion of an inspection robot, resolution may instead be considered in any coordinate system, such as cylindrical or spherical coordinates, and/or along axes unrelated to the motion of an inspection robot. It will be understood that the configurations of an inspection robot and operations described in the present disclosure can support arbitrary resolution in any coordinate system, with the inspection robot providing sufficient resolution as operated, in view of the target coordinate system. Accordingly, for example, where inspection resolution of 6-inches is desired in a target coordinate system that is diagonal to the travel direction of the inspection robot, the inspection robot and related operations described throughout the present disclosure can support whatever resolution is required (whether greater than 6-inches, less than 6-inches, or variable resolution depending upon the location over the inspection surface) to facilitate the 6-inch resolution of the target coordinate system. It can be seen that an inspection robot and/or related operations capable of achieving an arbitrary resolution in the coordinates of the movement of the inspection robot can likewise achieve arbitrary resolution in any coordinate system for the mapping of the inspection surface. For clarity of description, apparatus and operations to support an arbitrary resolution are described in view of the coordinate system of the movement of an inspection robot.

An example apparatus to support acoustic inspection of an inspection surface includes an inspection robot having a payload and a number of sleds mounted thereon, with the sleds each having at least one acoustic sensor mounted thereon. Accordingly, the inspection robot is capable of simultaneously determining acoustic parameters at a range of positions horizontally. Sleds may be positioned horizontally at a selected spacing, including providing a number of sleds to provide sensors positioned radially around several positions on a pipe or other surface feature of the inspection surface. In certain embodiments, vertical resolution is supported according to the sampling rate of the sensors, and/or the movement speed of the inspection robot. Additionally or alternatively, the inspection robot may have vertically displaced payloads, having an additional number of sleds mounted thereon, with the sleds each having at least one acoustic sensor mounted thereon. The utilization of additional vertically displaced payloads can provide additional resolution, either in the horizontal direction (e.g., where sleds of the vertically displaced payload(s) are offset from sleds in the first payload(s)) and/or in the vertical direction (e.g., where sensors on sleds of the vertically displaced payload(s) are sampling such that sensed parameters are vertically offset from sensors on sleds of the first payload(s)). Accordingly, it can be seen that, even where physical limitations of sled spacing, numbers of sensors supported by a given payload, or other considerations limit horizontal resolution for a given payload, horizontal resolution can be enhanced through the utilization of additional vertically displaced payloads. In certain embodiments, an inspection robot can perform another inspection run over a same area of the inspection surface, for example with sleds tracking in an offset line from a first run, with positioning information to ensure that both horizontal and/or vertical sensed parameters are offset from the first run.

Accordingly, an apparatus is provided that achieves significant resolution improvements, horizontally and/or vertically, over previously known systems. Additionally or alternatively, an inspection robot performs inspection operations at distinct locations on a descent operation than on an ascent operation, providing for additional resolution improvements without increasing a number of run operations required to perform the inspection (e.g., where an inspection robot ascends an inspection surface, and descends the inspection surface as a normal part of completing the inspection run). In certain embodiments, an apparatus is configured to perform multiple run operations to achieve the selected resolution. It can be seen that the greater the number of inspection runs required to achieve a given spatial resolution, the longer the down time for the system (e.g., an industrial system) being inspected (where a shutdown of the system is required to perform the inspection), the longer the operating time and greater the cost of the inspection, and/or the greater chance that a failure occurs during the inspection. Accordingly, even where multiple inspection runs are required, a reduction in the number of the inspection runs is beneficial.

In certain embodiments, an inspection robot includes a low fluid loss couplant system, enhancing the number of sensors that are supportable in a given inspection run, thereby enhancing available sensing resolution. In certain embodiments, an inspection robot includes individual down force support for sleds and/or sensors, providing for reduced fluid loss, reduced off-nominal sensing operations, and/or increasing the available number of sensors supportable on a payload, thereby enhancing available sensing resolution. In certain embodiments, an inspection robot includes a single couplant connection for a payload, and/or a single couplant connection for the inspection robot, thereby enhancing reliability and providing for a greater number of sensors on a payload and/or on the inspection robot that are available for inspections under commercially reasonable operations (e.g., configurable for inspection operations with reasonable reliability, checking for leaks, expected to operate without problems over the course of inspection operations, and/or do not require a high level of skill or expensive test equipment to ensure proper operation). In certain embodiments, an inspection robot includes acoustic sensors coupled to acoustic cones, enhancing robust detection operations (e.g., a high percentage of valid sensing data, ease of acoustic coupling of a sensor to an inspection surface, etc.), reducing couplant fluid losses, and/or easing integration of sensors with sleds, thereby supporting an increased number of sensors per payload and/or inspection robot, and enhancing available sensing resolution. In certain embodiments, an inspection robot includes utilizing water as a couplant, thereby reducing fluid pumping losses, reducing risks due to minor leaks within a multiple plumbing line system to support multiple sensors, and/or reducing the impact (environmental, hazard, clean-up, etc.) of performing multiple inspection runs and/or performing an inspection operation with a multiplicity of acoustic sensors operating.

Figure 33:
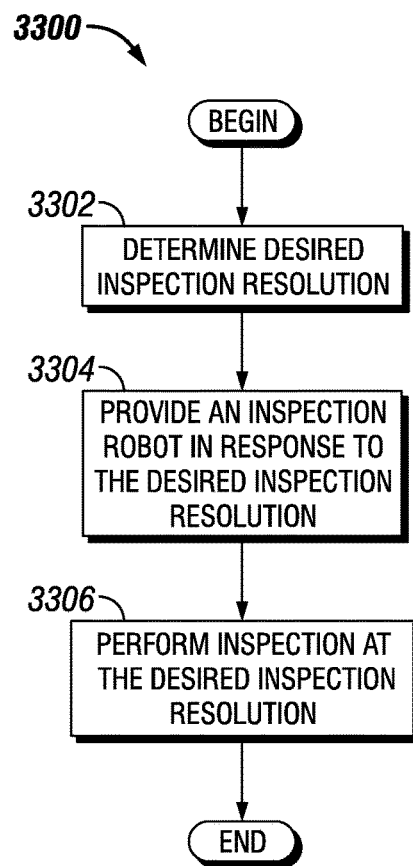
FIG. 33 is a schematic flow diagram of a procedure to perform an inspection at an arbitrary resolution.

Referencing FIG. 33, an example procedure 3300 to acoustically inspect an inspection surface with an arbitrary (or selectable) resolution is schematically depicted. The example procedure 3300 includes an operation 3302 to determine a desired resolution of inspection for the surface. The operation 3302 includes determining the desired resolution in whatever coordinate system is considered for the inspection surface, and translating the desired resolution for the coordinate system of the inspection surface to a coordinate system of an inspection robot (e.g., in terms of vertical and horizontal resolution for the inspection robot), if the coordinate system for the inspection surface is distinct from the coordinate system of the inspection robot. The example procedure 3300 further includes an operation 3304 to provide an inspection robot in response to the desired resolution of inspection, the inspection robot having at least one payload, a number of sleds mounted on the payload, and at least one acoustic sensor mounted on each sled. It will be understood that certain sleds on the payload may not have an acoustic sensor mounted thereupon, but for provision of selected acoustic inspection resolution, only the sleds having an acoustic sensor mounted thereupon are considered. In certain embodiments, operation 3304 additionally or alternatively includes one or more operations such as: providing multiple payloads; providing vertically displaced payloads; providing offset sleds on one or more vertically displaced payloads; providing payloads having a single couplant connection for the payload; providing an inspection robot having a single couplant connection for the inspection robot; providing an inspection robot utilizing water as a couplant; providing a down force to the sleds to ensure alignment and/or reduced fluid loss; providing degrees of freedom of movement to the sleds to ensure alignment and/or robust obstacle traversal; providing the sensors coupled to an acoustic cone; and/or configuring a horizontal spacing of the sleds in response to the selected resolution (e.g., spaced to support the selected resolution, spaced to support the selected resolution between an ascent and a descent, and/or spaced to support the selected resolution with a scheduled number of inspection runs).

The example procedure 3300 further includes an operation 3306 to perform an inspection operation of an inspection surface with arbitrary resolution. For example, operation 3306 includes at least: operating the number of horizontally displaced sensors to achieve the arbitrary resolution; operating vertically displaced payloads in a scheduled manner (e.g., out of phase with the first payload thereby inspecting a vertically distinct set of locations of the inspection surface); operating vertically displaced payloads to enhance horizontal inspection resolution; performing an inspection on a first horizontal track on an ascent, and a second horizontal track distinct from the first horizontal track on a descent; performing an inspection on a first vertical set of points on an ascent, and on a second vertical set of points on a descent (which may be on the same or a distinct horizontal track); and/or performing a plurality of inspection runs where the horizontal and/or vertical inspection positions of the multiple runs are distinct from the horizontal and/or vertical inspection positions of a first run. Certain operations of the example procedure 3300 may be performed by a controller 802.

While operations of procedure 3300, and an apparatus to provide for arbitrary or selected resolution inspections of a system are described in terms of acoustic sensing, it will be understood that arbitrary or selected resolution of other sensed parameters are contemplated herein. In certain embodiments, acoustic sensing provides specific challenges that are addressed by certain aspects of the present disclosure. However, sensing of any parameter, such as temperature, magnetic or electro-magnetic sensing, infra-red detection, UV detection, composition determinations, and other sensed parameters also present certain challenges addressed by certain aspects of the present disclosure. For example, the provision of multiple sensors in a single inspection run at determinable locations, the utilization of an inspection robot (e.g., instead of a person positioned in the inspection space), including an inspection robot with position sensing, and/or the reduction of sensor interfaces including electrical and communication interfaces, provides for ease of sensing for any sensed parameters at a selected resolution. In certain embodiments, a system utilizes apparatuses and operations herein to achieve arbitrary resolution for acoustic sensing. In certain embodiments, a system additionally or alternatively utilizes apparatuses and operations herein to achieve arbitrary resolution for any sensed parameter.

Figure 34:
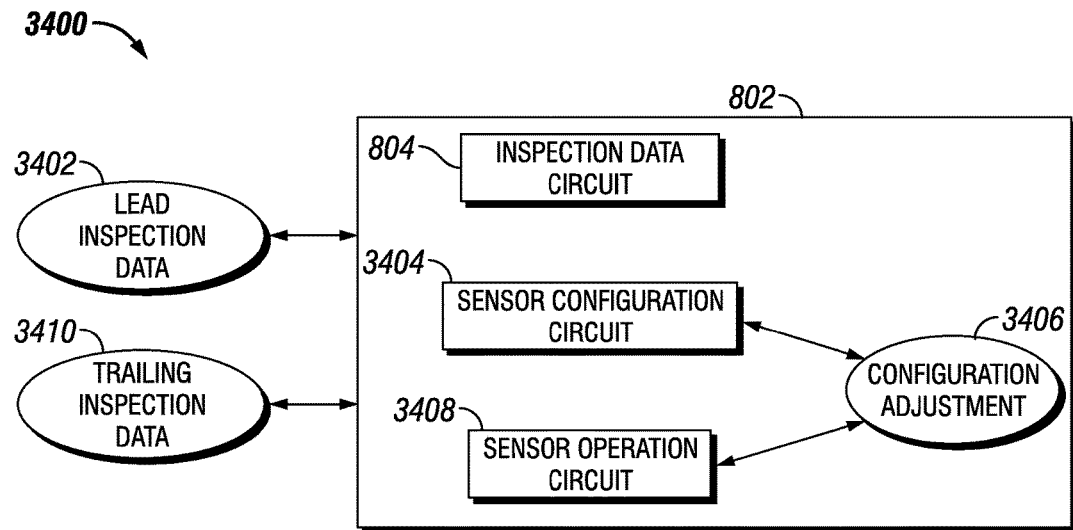
FIG. 34 is a schematic block diagram of an apparatus for adjusting a trailing sensor configuration.

Referencing FIG. 34, an example apparatus 3400 is depicted for configuring a trailing sensor inspection scheme in response to a leading sensor inspection value. The example apparatus 3400 includes a controller 802 having an inspection data circuit 804 that interprets lead inspection data 3402 from a lead sensor. Example and non-limiting lead sensors include a sensor mounted on a sled of a forward payload 2006, a sensor mounted on either a forward payload 2006 or a rear payload 1402 of an inspection robot having a trailing payload 2008, and/or a sensor operated on a first run of an inspection robot, where operations of the apparatus 3400 proceed with adjusting operations of a sensor on a subsequent run of the inspection robot (e.g., the first run is ascending, and the subsequent run is descending; the first run is descending, and the subsequent run is ascending; and/or the first run is performed at a first time, and the subsequent run is performed at a second, later, time).

The example controller 802 further includes a sensor configuration circuit 3404 structured to determine a configuration adjustment 3406 for a trailing sensor. Example and non-limiting trailing sensors include any sensor operating over the same or a substantially similar portion of the inspection surface as the lead sensor, at a later point in time. A trailing sensor may be a sensor positioned on a payload behind the payload having the lead sensor, a physically distinct sensor from the lead sensor operating over the same or a substantially similar portion of the inspection surface after the lead sensor, and/or a sensor that is physically the same sensor as the lead sensor, but reconfigured in some aspect (e.g., sampling parameters, calibrations, inspection robot rate of travel change, etc.). A portion that is substantially similar includes a sensor operating on a sled in the same horizontal track (e.g., in the direction of inspection robot movement) as the lead sensor, a sensor that is sensing a portion of the inspection sensor that is expected to determine the same parameters (e.g., wall thickness in a given area) of the inspection surface as that sensed by the lead sensor, and/or a sensor operating in a space of the inspection area where it is expected that determinations for the lead sensor would be effective in adjusting the trailing sensor. Example and non-limiting determinations for the lead sensor to be effective in adjusting the trailing sensor include pipe thickness determinations for a same pipe and/or same cooling tower, where pipe thickness expectations may affect the calibrations or other settings utilized by the lead and trailing sensors; determination of a coating thickness where the trailing sensor operates in an environment that has experienced similar conditions (e.g., temperatures, flow rates, operating times, etc.) as the conditions experienced by the environment sensed by the lead sensor; and/or any other sensed parameter affecting the calibrations or other settings utilized by the lead and trailing sensors where knowledge gained by the lead sensor could be expected to provide information utilizable for the trailing sensor.

Example and non-limiting configuration adjustments 3406 include changing of sensing parameters such as cut-off times to observe peak values for ultra-sonic processing, adjustments of rationality values for ultra-sonic processing, enabling of trailing sensors or additional trailing sensors (e.g., X-ray, gamma ray, high resolution camera operations, etc.), adjustment of a sensor sampling rate (e.g., faster or slower), adjustment of fault cut-off values (e.g., increase or decrease fault cutoff values), adjustment of any transducer configurable properties (e.g., voltage, waveform, gain, filtering operations, and/or return detection algorithm), and/or adjustment of a sensor range or resolution value (e.g., increase a range in response to a lead sensing value being saturated or near a range limit, decrease a range in response to a lead sensing value being within a specified range window, and/or increase or decrease a resolution of the trailing sensor). In certain embodiments, a configuration adjustment 3406 to adjust a sampling rate of a trailing sensor includes by changing a movement speed of an inspection robot. Example and non-limiting configuration adjustments include any parameters described in relation to FIGS. 39, 40, and 43-48 and the related descriptions. It can be seen that the knowledge gained from the lead inspection data 3402 can be utilized to adjust the trailing sensor plan which can result more reliable data (e.g., where calibration assumptions appear to be off-nominal for the real inspection surface), the saving of one or more inspection runs (e.g., reconfiguring the sensing plan in real-time to complete a successful sensing run during inspection operations), improved operations for a subsequent portion of a sensing run (e.g., a first inspection run of the inspection surface improves the remaining inspection runs, even if the vertical track of the first inspection run must be repeated), and/or efficient utilization of expensive sensing operations by utilizing such operations only when the lead inspection data 3402 indicates such operations are useful or required. The example controller 802 includes a sensor operation circuit 3408 that adjusts parameters of the trailing sensor in response to the configuration adjustment 3406, and the inspection data circuit 804 interpreting trailing inspection data 3410, wherein the trailing sensors are responsive to the adjusted parameters by the sensor operation circuit.

Figure 35:
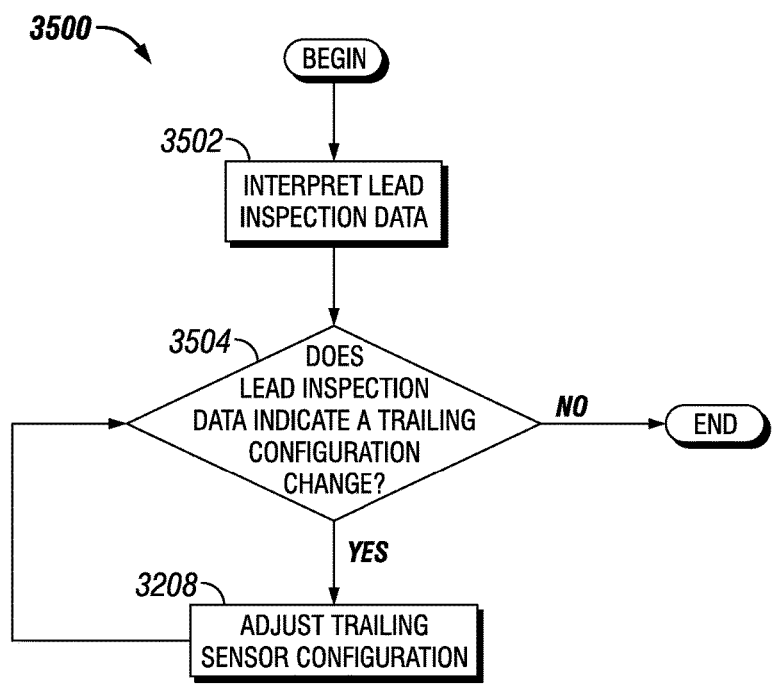
FIG. 35 is a schematic flow diagram of a procedure to adjust a trailing sensor configuration.

Referencing FIG. 35, an example procedure 3500 to configure a trailing sensor in response to a leading sensor value is depicted. The example procedure 3500 includes an operation 3502 to interpret lead inspection data provided by a leading sensor, and an operation 3504 to determine whether the lead inspection data indicates that a trailing sensor configuration should be adjusted. Where the operation 3504 determines that the trailing sensor configuration should be adjusted, the example procedure 3500 includes an operation 3506 to adjust the trailing sensor configuration in response to the lead inspection data. Example and non-limiting operations 3506 to adjust a trailing sensor configuration include changing a calibration for the sensor (e.g., an analog/digital processor configuration, cutoff time values, and/or speed-of-sound values for one or more materials), changing a range or resolution of the trailing sensor, enabling or disabling sensing operations of a trailing sensor, and/or adjusting a speed of travel of an inspection robot. In certain embodiments, operations 3506 include adjusting a horizontal position of a trailing sensor (e.g., where a horizontal position of a sled 1 on a payload 2 is actively controllable by a controller 802, and/or adjusted manually between the lead sensing operation and the trailing sensing operation).

In certain embodiments, lead inspection data 3402 includes ultra-sonic information such as processed ultra-sonic information from a sensor, and the sensor configuration circuit 3404 determines to utilize a consumable, slower, and/or more expensive sensing, repair, and/or marking operation by providing a configuration adjustment 3406 instructing a trailing sensor to operate, or to change nominal operations, in response to the lead inspection data 3402. For example, lead inspection data 3402 may indicate a thin wall, and sensor configuration circuit 3404 provides the configuration adjustment 3406 to alter a trailing operation such as additional sensing with a more capable sensor (e.g., a more expensive or capable ultra-sonic sensor, an X-ray sensor, a gamma ray sensor, or the like) and/or to operate a repair or marking tool (e.g., which may have a limited or consumable amount of coating material, marking material, or the like) at the location determined to have the thin wall. Accordingly, expense, time, and/or operational complication can be added to inspection operations in a controlled manner according to the lead inspection data 3402.

An example apparatus is disclosed to perform an inspection of an industrial surface. Many industrial surfaces are provided in hazardous locations, including without limitation where heavy or dangerous mechanical equipment operates, in the presence of high temperature environments, in the presence of vertical hazards, in the presence of corrosive chemicals, in the presence of high pressure vessels or lines, in the presence of high voltage electrical conduits, equipment connected to and/or positioned in the vicinity of an electrical power connection, in the presence of high noise, in the presence of confined spaces, and/or with any other personnel risk feature present. Accordingly, inspection operations often include a shutdown of related equipment, and/or specific procedures to mitigate fall hazards, confined space operations, lockout-tagout procedures, or the like. In certain embodiments, the utilization of an inspection robot allows for an inspection without a shutdown of the related equipment. In certain embodiments, the utilization of an inspection robot allows for a shutdown with a reduced number of related procedures that would be required if personnel were to perform the inspection. In certain embodiments, the utilization of an inspection robot provides for a partial shutdown to mitigate some factors that may affect the inspection operations and/or put the inspection robot at risk, but allows for other operations to continue. For example, it may be acceptable to position the inspection robot in the presence of high pressure or high voltage components, but operations that generate high temperatures may be shut down.

In certain embodiments, the utilization of an inspection robot provides additional capabilities for operation. For example, an inspection robot having positional sensing within an industrial environment can request shutdown of only certain aspects of the industrial system that are related to the current position of the inspection robot, allowing for partial operations as the inspection is performed. In another example, the inspection robot may have sensing capability, such as temperature sensing, where the inspection robot can opportunistically inspect aspects of the industrial system that are available for inspection, while avoiding other aspects or coming back to inspect those aspects when operational conditions allow for the inspection. Additionally, in certain embodiments, it is acceptable to risk the industrial robot (e.g., where shutting down operations exceed the cost of the loss of the industrial robot) to perform an inspection that has a likelihood of success, where such risks would not be acceptable for personnel. In certain embodiments, a partial shutdown of a system has lower cost than a full shutdown, and/or can allow the system to be kept in a condition where restart time, startup operations, etc. are at a lower cost or reduced time relative to a full shutdown. In certain embodiments, the enhanced cost, time, and risk of performing additional operations beyond mere shutdown, such as compliance with procedures that would be required if personnel were to perform the inspection, can be significant.

Figure 36:
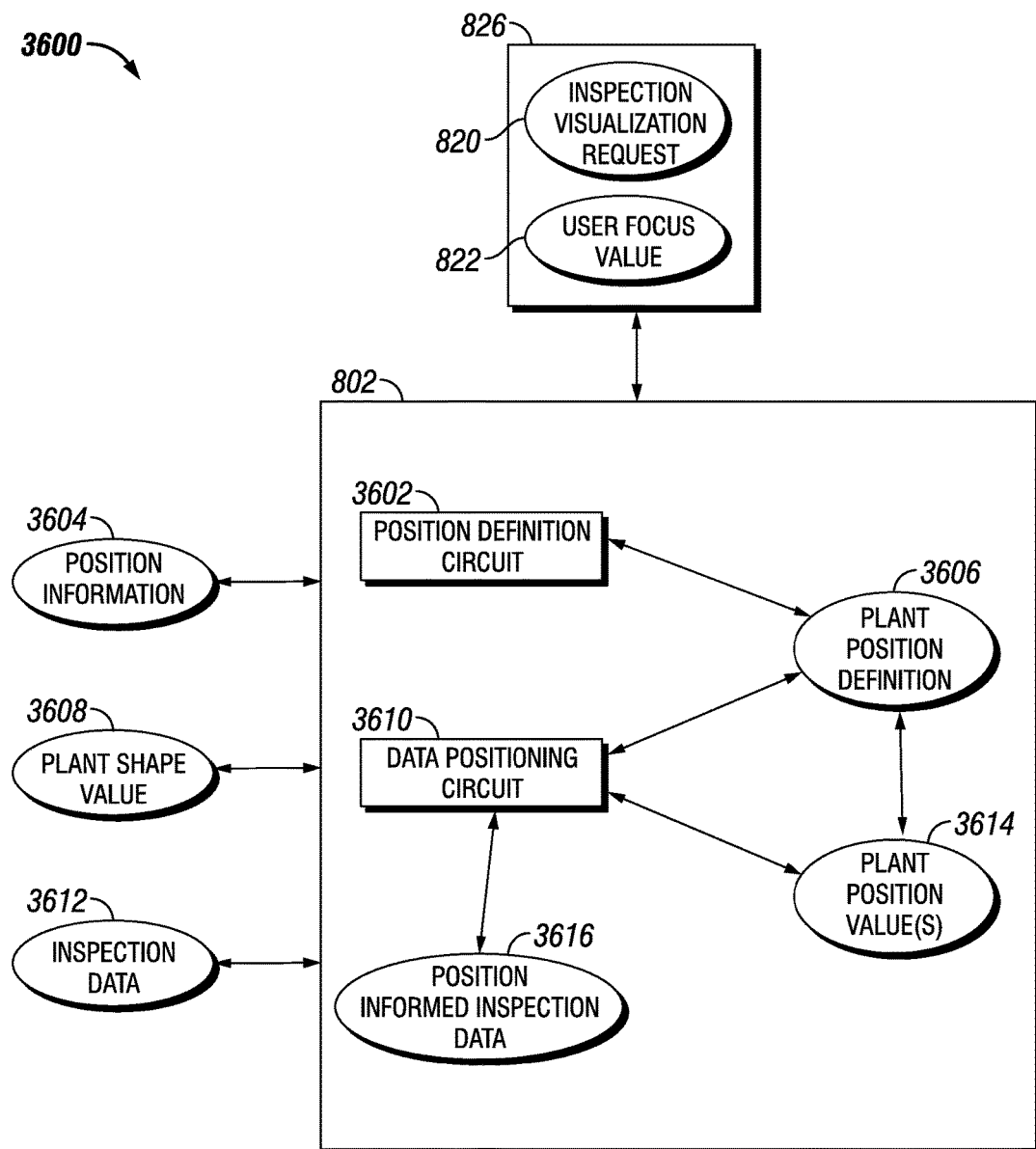
FIG. 36 is a schematic block diagram of an apparatus for providing position informed inspection data.

Referencing FIG. 36, an example apparatus 3600 to inspect a plant, industrial system, and/or inspection surface utilizing position information is depicted schematically. The example apparatus 3600 includes a position definition circuit 3602 that interprets position information 3604, and/or determines a plant position definition 3606 (e.g., a plant definition value) and an inspection robot position (e.g., as one or more plant position values 3614) in response to the position information 3604. Example and non-limiting position information 3604 includes relative and/or absolute position information—for example a distance from a reference position (e.g., a starting point, stopping point, known object in proximity to the plant, industrial system, and/or inspection surface, or the like). In certain embodiments, position information 3604 is determinable according to a global positioning service (GPS) device, ultra-wide band radio frequency (RF) signaling, LIDAR or other direct distance measurement devices (including line-of-sight and/or sonar devices), aggregating from reference points (e.g., routers, transmitters, know devices in communication with the inspection robot, or the like), utilizing known obstacles as a reference point, encoders (e.g., a wheel counter or other device), barometric sensors (e.g., altitude determination), utilization of a known sensed value correlated to position (e.g., sound volume or frequency, temperature, vibration, etc.), and/or utilizing an inertial measurement unit (e.g., measuring and/or calculating utilizing an accelerometer and/or gyroscope). In certain embodiments, values may be combined to determine the position information 3604—for example in 3-D space without further information, four distance measurements are ordinarily required to determine a specific position value. However, utilizing other information, such as a region of the inspection surface that the inspection robot is operating on (e.g., which pipe the inspection robot is climbing), an overlay of the industrial surface over the measurement space, a distance traveled from a reference point, a distance to a reference point, etc., the number of distance measurements required to determine a position value can be reduced to three, two, one, or even eliminated and still position information 3604 is determinable. In certain embodiments, the position definition circuit 3602 determines the position information 3604 completely or partially on dead reckoning (e.g., accumulating speed and direction from a known position, and/or direction combined with a distance counter), and/or corrects the position information 3604 when feedback based position data (e.g., a true detected position) is available.

Example and non-limiting plant position values 3608 include the robot position information 3604 integrated within a definition of the plant space, such as the inspection surface, a defined map of a portion of the plant or industrial system, and/or the plant position definition 3606. In certain embodiments, the plant space is predetermined, for example as a map interpreted by the controller 802 and/or pre-loaded in a data file describing the space of the plant, inspection surface, and/or a portion of the plant or industrial surface. In certain embodiments, the plant position definition 3606 is created in real-time by the position definition circuit 3602—for example by integrating the position information 3604 traversed by the inspection robot, and/or by creating a virtual space that includes the position information 3604 traversed by the inspection robot. For example, the position definition circuit 3602 may map out the position information 3604 over time, and create the plant position definition 3606 as the aggregate of the position information 3604, and/or create a virtual surface encompassing the aggregated plant position values 3614 onto the surface. In certain embodiments, the position definition circuit 3602 accepts a plant shape value 3608 as an input (e.g., a cylindrical tank being inspected by the inspection robot having known dimensions), deduces the plant shape value 3608 from the aggregated position information 3604 (e.g., selecting from one of a number of simple or available shapes that are consistent with the aggregated plant position definition 3606), and/or prompts a user (e.g., an inspection operator and/or a client for the data) to select one of a number of available shapes to determine the plant position definition 3606.

The example apparatus 3600 includes a data positioning circuit 3610 that interprets inspection data 3612 and correlates the inspection data 3612 to the position information 3604 and/or to the plant position values 3614. Example and non-limiting inspection data 3612 includes: sensed data by an inspection robot; environmental parameters such as ambient temperature, pressure, time-of-day, availability and/or strength of wireless communications, humidity, etc.; image data, sound data, and/or video data taken during inspection operations; metadata such as an inspection number, customer number, operator name, etc.; setup parameters such as the spacing and positioning of sleds, payloads, mounting configuration of sensors, and the like; calibration values for sensors and sensor processing; and/or operational parameters such as fluid flow rates, voltages, pivot positions for the payload and/or sleds, inspection robot speed values, downforce parameters, etc. In certain embodiments, the data positioning circuit 3610 determines the positional information 3604 corresponding to inspection data 3612 values, and includes the positional information 3604 as an additional parameter with the inspection data 3612 values and/or stores a correspondence table or other data structure to relate the positional information 3604 to the inspection data values 3612. In certain embodiments, the data positioning circuit 3610 additionally or alternatively determines the plant position definition 3606, and includes a plant position value 3614 (e.g., as a position within the plant as defined by the plant position definition 3606) as an additional parameter with the inspection data 3612 values and/or stores a correspondence table or other data structure to relate the plant position values 3614 to the inspection data values 3612. In certain embodiments, the data positioning circuit 3610 creates position informed data 3616, including one or more, or all, aspects of the inspection data 3612 correlated to the position information 3604 and/or to the plant position values 3614.

In certain embodiments, for example where dead reckoning operations are utilized to provide position information 3604 over a period of time, and then a corrected position is available through a feedback position measurement, the data positioning circuit 3602 updates the position informed inspection data 3616—for example re-scaling the data according to the estimated position for values according to the changed feedback position (e.g., where the feedback position measurement indicates the inspection robot traveled 25% further than expected by dead reckoning, position information 3604 during the dead reckoning period can be extended by 25%) and/or according to rationalization determinations or externally available data (e.g., where over 60 seconds the inspection robot traverses 16% less distance than expected, but sensor readings or other information indicate the inspection robot may have been stuck for 10 seconds, then the position information 3604 may be corrected to represent the 10-seconds of non-motion rather than a full re-scale of the position informed inspection data 3616). In certain embodiments, dead reckoning operations may be corrected based on feedback measurements as available, and/or in response to the feedback measurement indicating that the dead reckoning position information exceeds a threshold error value (e.g., 1%, 0.1%, 0.01%, etc.).

It can be seen that the operations of apparatus 3600 provide for position-based inspection information. Certain systems, apparatuses, and procedures throughout the present disclosure utilize and/or can benefit from position informed inspection data 3616, and all such embodiments are contemplated herein. Without limitation to any other disclosures herein, certain aspects of the present disclosure include: providing a visualization of inspection data 3612 in position information 3604 space and/or in plant position value 3614 space; utilizing the position informed inspection data 3616 in planning for a future inspection on the same or a similar plant, industrial system, and/or inspection surface (e.g., configuring sled number and spacing, inspection robot speed, inspection robot downforce for sleds and/or sensors, sensor calibrations, planning for traversal and/or avoidance of obstacles, etc.); providing a format for storing a virtual mark (e.g., replacing a paint or other mark with a virtual mark as a parameter in the inspection data 3612 correlated to a position); determining a change in a plant condition in response to the position informed inspection data 3616 (e.g., providing an indication that expected position information 3604 did not occur in accordance with the plant position definition 3606—for example indicating a failure, degradation, or unexpected object in a portion of the inspected plant that is not readily visible); and/or providing a health indicator of the inspection surface (e.g., depicting regions that are nominal, passed, need repair, will need repair, and/or have failed). In certain embodiments, it can be seen that constructing the position informed inspection data 3616 using position information 3604 only, including dead reckoning based position information 3604, nevertheless yields many of the benefits of providing the position informed inspection data 3616. In certain further embodiments, the position informed inspection data 3616 is additionally or alternatively constructed utilizing the plant position definition 3606, and/or the plant position values 3614.

Figure 37:
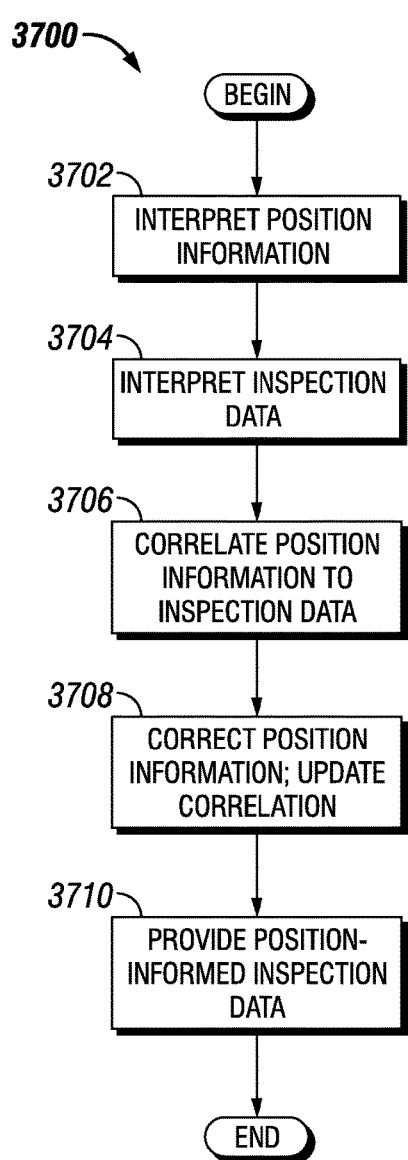
FIG. 37 is a schematic flow diagram of a procedure to provide position informed inspection data.

Referencing FIG. 37, an example procedure 3700 to inspect a plant, industrial system, and/or inspection surface utilizing position information is depicted. The example procedure 3700 includes an operation 3702 to interpret position information, an operation 3704 to interpret inspection data, and an operation 3706 correlate the inspection data to the position information. The example procedure 3700 further includes an operation 3708 to correct the position information (e.g., updating a dead reckoning-based position information), and to update the correlation of the inspection data to the position information. The example procedure further includes an operation 3710 to provide position informed inspection data in response to the correlated inspection data. In certain embodiments, operation 3706 is additionally or alternatively performed on the position informed inspection data, where the position informed inspection data is corrected, and operation 3710 includes providing the position informed inspection data. In certain embodiments, one or more operations of a procedure 3700 are performed by a controller 802.

Figure 38:
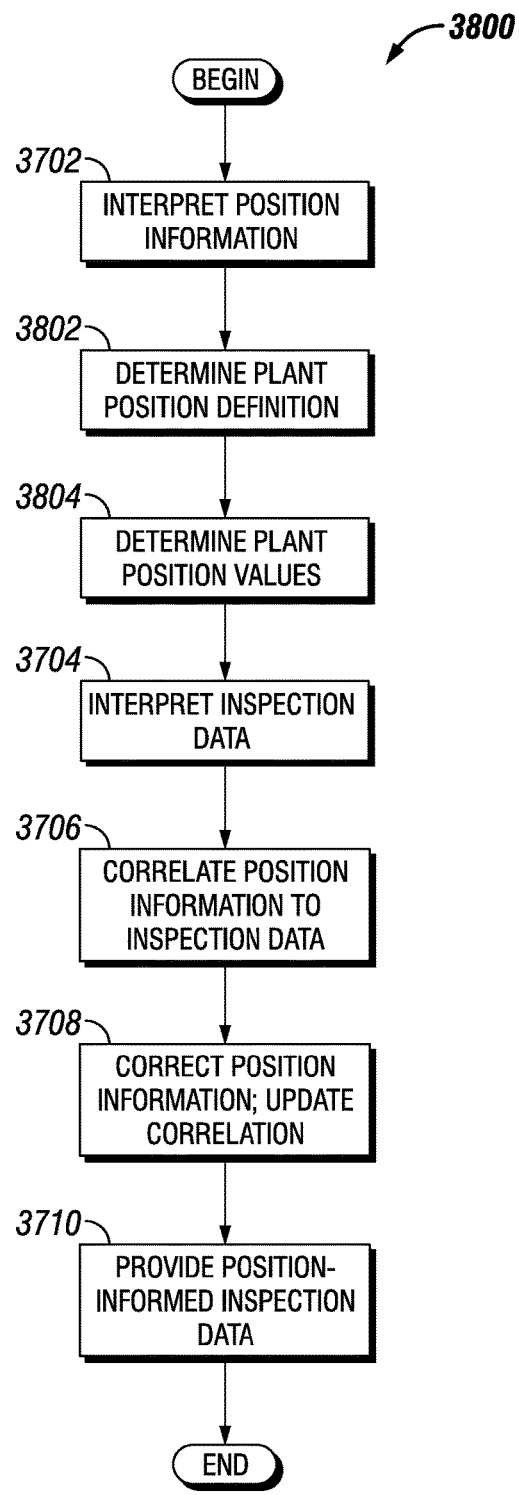
FIG. 38 is a schematic flow diagram of another procedure to provide position informed inspection data.

Referencing FIG. 38, an example procedure 3800 to inspect a plant, industrial system, and/or inspection surface utilizing position information is depicted. In addition to operations of procedure 3700, example procedure 3800 includes an operation 3802 to determine a plant definition value, and an operation 3804 to determine plant position values in response to the position information and the plant position definition. Operation 3706 further includes an operation to correlate the inspection data with the position information and/or the plant position values. In certain embodiments, one or more operations of procedure 3800 are performed by a controller 802.

Figure 39:
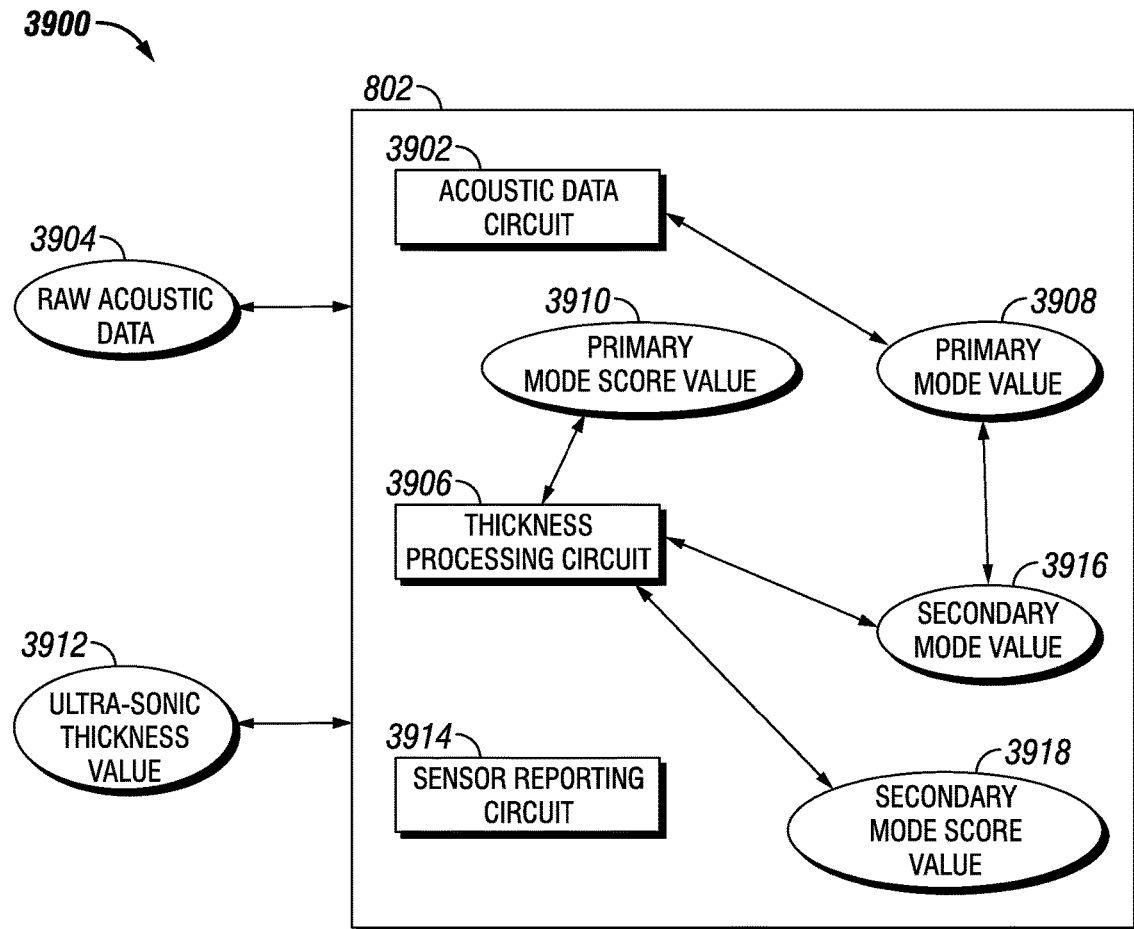
FIG. 39 is a schematic block diagram of an apparatus for providing an ultra-sonic thickness value.

Referencing FIG. 39, an example apparatus 3900 for processing ultra-sonic sensor readings is depicted schematically. The example apparatus 3900 includes a controller 802 having an acoustic data circuit 3902 that determines return signals from the tested surface—for example a transducer in the sensor 2202 sends a sound wave through the couplant chamber to the inspection surface, and the raw acoustic data 3904 includes primary (e.g., from the surface inspection surface), secondary (e.g., from a back wall, such as a pipe wall or tank wall) and/or tertiary (e.g., from imperfections, cracks, or defects within the wall) returns from the inspection surface.

In certain embodiments, the controller 802 includes a thickness processing circuit 3906 that determines a primary mode value 3908 in response to the raw acoustic data 3904. The primary mode value 3908, in certain embodiments, includes a determination based upon a first return and a second return of the raw acoustic data 3904, where a time difference between the first return and the second return indicates a thickness of the inspection surface material (e.g., a pipe). The foregoing operations of the thickness processing circuit 3906 are well known in the art, and are standard operations for ultra-sonic thickness testing. However, the environment for the inspection robot is not typical, and certain further improvements to operations are described herein. An inspection robot, in certain embodiments, performs a multiplicity of ultra-sonic thickness determinations, often with simultaneous (or nearly) operations from multiple sensors. Additionally, in certain embodiments, it is desirable that the inspection robot operate: autonomously without the benefit of an experienced operator; without high-end processing in real-time to provide substantial displays to a user to determine whether parameters are not being determined properly; and/or with limited communication resources utilized for post-processing that is fast enough that off nominal operation can be adjusted after significant post-processing.

In certain embodiments, the thickness processing circuit 3906 determines a primary mode score value 3910. In certain embodiments, the thickness processing circuit 3906 determines the primary mode score value 3910 in response to a time of arrival for the primary (e.g., inspection surface face) return from the raw acoustic data 3904. Because the delay time for the sensor is a known and controlled value (e.g., reference FIGS. 28 and 31, and the related description), the return time of the primary return is known with high confidence. Additionally or alternatively, the thickness processing circuit 3906 determines the primary mode score value 3910 in response to the character of the primary return—for example a sharp peak of a known width and/or amplitude. In certain embodiments, the primary mode score value 3910 calculation is calibrated in response to the material of the inspection surface—although known materials such as iron, various types of steel, and other surfaces can utilize nominal calibrations. In certain embodiments, the configuration adjustment 3406 based on lead inspection data 3402 is utilized to calibrate a primary mode score value 3910 calculation for a sensor providing the trailing inspection data 3410. In certain embodiments, determining that the first peak (related to the primary return) meets expected characteristics is sufficient to provide confidence to utilize the primary mode value 3908 as the ultra-sonic thickness value 3912. In certain embodiments, the ultra-sonic thickness value 3912 is the inspection data for the sensor, and/or a part of the inspection data for the sensor.

In certain embodiments, the thickness processing circuit 3906 additionally or alternatively considers the timing of arrival for a secondary return, peak arrival time, and/or peak width of the secondary return (e.g., from the back wall) in determining the primary mode score value 3910. For example, if the secondary return indicates a wall thickness that is far outside of an expected thickness value, either greater or lower, the primary mode score value 3910 may be reduced. In certain embodiments, if the secondary return has a peak characteristic that is distinct from the expected characteristic (e.g., too narrow, not sharp, etc.) then the primary mode score value 3910 may be reduced. Additionally or alternatively, feedback data regarding the sensor may be utilized to adjust the primary mode score value 3910—for example if the sensor is out of alignment with the inspection surface, the sensor (or sled) has lifted off of the inspection surface, a sled position for a sled having an acoustic sensor, and/or if a couplant anomaly is indicated (e.g., couplant flow is lost, a bubble is detected, etc.) then the primary mode score value 3910 may be reduced.

In certain embodiments, for example when the primary mode score value 3910 indicates that the primary mode value 3908 is to be trusted, the controller 802 includes a sensor reporting circuit 3914 that provides the ultra-sonic thickness value 3912 in response to the primary mode value 3908. In certain embodiments, if the primary mode score value 3910 is sufficiently high, the thickness processing circuit 3906 omits operations to determine a secondary mode value 3916. In certain embodiments, the thickness processing circuit 3906 performs operations to determine the secondary mode value 3916 in response to the primary mode score value 3910 is at an intermediate value, and/or if feedback data regarding the sensor indicates off-nominal operation, even when the primary mode score value 3910 is sufficiently high (e.g., to allow for improved post-processing of the inspection data). In certain embodiments, the thickness processing circuit 3906 determines the secondary mode value 3916 at all times, for example to allow for improved post-processing of the inspection data. In certain embodiments, the sensor reporting circuit 3914 provides processed values for the primary mode value 3908 and/or the secondary mode value 3916, and/or the primary mode scoring value 3910 and/or a secondary mode score value 3918, either as the inspection data and/or as stored data to enable post-processing and/or future calibration improvements. In certain embodiments, the sensor reporting circuit 3914 provides the raw acoustic data 3904, either as the inspection data and/or as stored data to enable post-processing and/or future calibration improvements.

The example thickness processing circuit 3906 further determines, in certain embodiments, a secondary mode value 3916. An example secondary mode value 3916 includes values determined from a number of reflected peaks—for example determining which of a number of reflected peaks are primary returns (e.g., from a face of the inspection surface) and which of a number of reflected peaks are secondary returns (e.g., from a back wall of the inspection surface). In certain embodiments, a Fast-Fourier Transform (FFT), wavelet analysis, or other frequency analysis technique is utilized by the thickness processing circuit 3906 to determine the energy and character of the number of reflected peaks. In certain embodiments, the thickness processing circuit 3906 determines a secondary mode score value 3918—for example from the character and consistency of the peaks, and determines an ultra-sonic thickness value 3912 from the peak-to-peak distance of the number of reflected peaks. The operations of the example apparatus 3900, which in certain embodiments favor utilization of the primary mode value 3908, provide for rapid and high confidence determinations of the ultra-sonic thickness value 3912 in an environment where a multiplicity of sensors are providing raw acoustic data 3904, computing resources are limited, and a large number of sensor readings are to be performed without supervision of an experienced operator.

In certain embodiments, any one or more of the ultra-sonic thickness value 3912, the primary mode value 3908, the secondary mode value 3916, the primary mode score value 3910, and/or the secondary mode score value 3918 are provided or stored as position informed inspection data 3616. The correlation of the values 3912, 3908, 3916, 3910, and/or 3918 with position data as position informed inspection data 3616 provides for rapid visualizations of the characteristics of the inspection surface, and provides for rapid convergence of calibration values for inspection operations on the inspection surface and similar surfaces. In certain embodiments, the raw acoustic data 3904 is provided or stored as position informed inspection data 3616.

Figure 40:
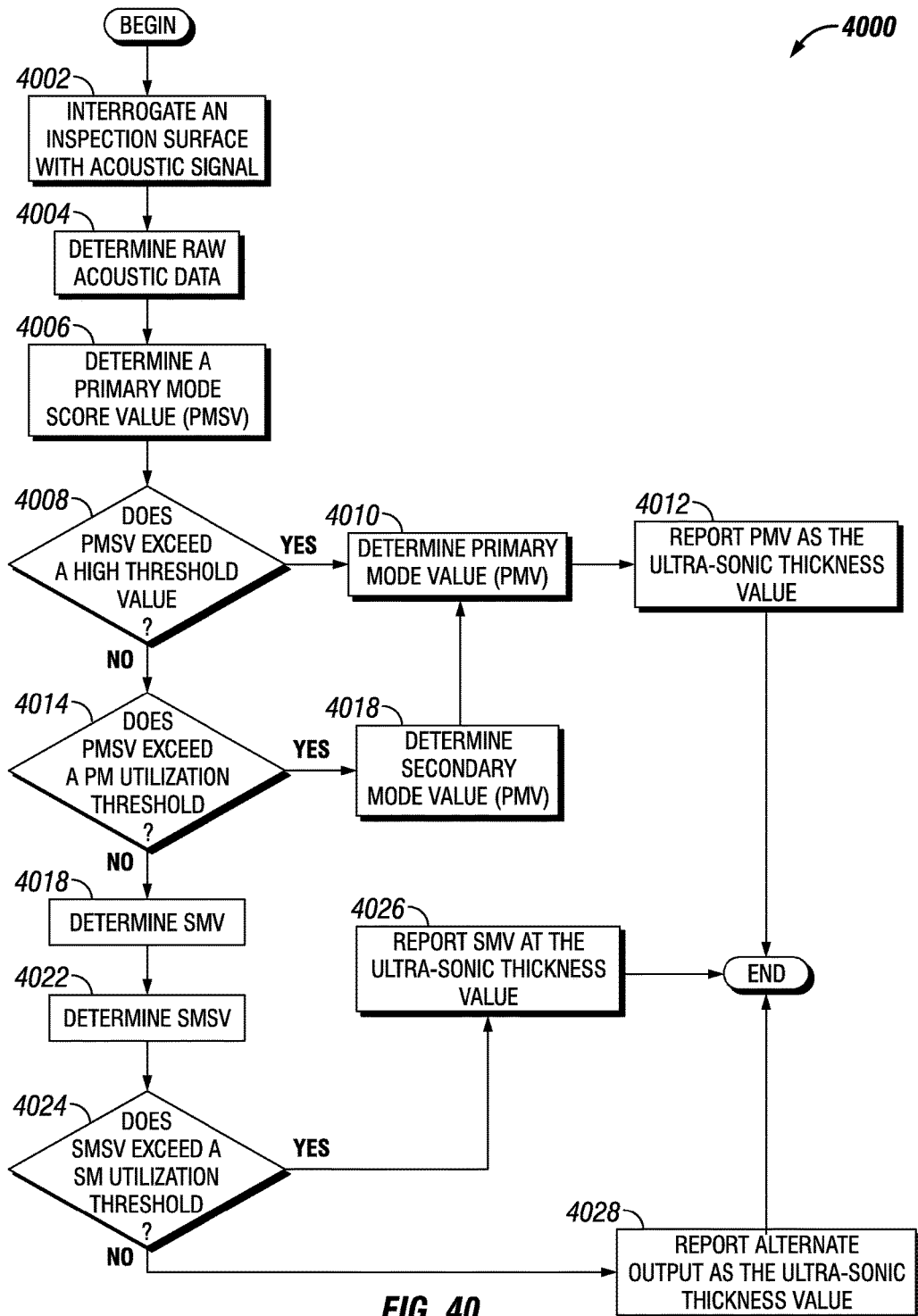
FIG. 40 is a schematic flow diagram of a procedure to provide an ultra-sonic thickness value.

Referencing FIG. 40, an example procedure 4000 to process ultra-sonic sensor readings is depicted schematically. In certain embodiments, procedure 4000 processes ultra-sonic sensor readings for an inspection robot having a number of ultra-sonic sensor mounted thereon. The example procedure 4000 includes an operation 4002 to interrogate an inspection surface with an acoustic signal (e.g., acoustic impulse from a transducer). The example procedure 4000 further includes an operation 4004 to determine raw acoustic data, such as return signals from the inspection surface. The example procedure 4000 further includes an operation 4006 to determine a primary mode score value in response to a primary peak value, and/or further in response to a secondary peak value, from the raw acoustic data. The example procedure 4000 further includes an operation 4008 to determine whether the primary mode score value exceeds a high threshold value, such as whether the primary mode value is deemed to be reliable without preserving a secondary mode value. In response to the operation 4008 determining the primary mode score value exceeds the high threshold value, the procedure 4000 further includes an operation 4010 to determine the primary mode value, and an operation 4012 to report the primary mode value as an ultra-sonic thickness value. In response to the operation 4008 determining the primary mode score value does not exceed the high threshold value, the procedure includes an operation 4014 to determine whether the primary mode score value exceeds a primary mode utilization value. In certain embodiments, in response to the operation 4014 determining the primary mode score value exceeds the primary mode utilization value, the procedure 4000 includes the operation 4010 to determine the primary mode value, an operation 4018 to determine the secondary mode value, and the operation 4012 to provide the primary mode value as the ultra-sonic thickness value. In response to the operation 4014 determining the primary mode score value does not exceed the primary mode utilization value, the procedure 4000 includes the operation 4018 to determine the secondary mode value and an operation 4022 to determine the secondary mode score value. The procedure 4000 further includes an operation 4024 to determine whether the secondary mode score value exceeds a secondary mode utilization value, and in response to operation 4024 determining the secondary mode score value exceeds the secondary mode utilization value, the procedure 4000 includes an operation 4026 to provide the secondary mode value as the ultra-sonic thickness value. In response to the operation 4024 determining the secondary mode score value does not exceed the secondary mode utilization value, the procedure 4000 includes an operation 4028 to provide an alternate output as the ultra-sonic thickness value. In certain embodiments, operation 4028 includes providing an error value (e.g., data not read), one of the primary mode value and the secondary mode value having a higher score, and/or combinations of these (e.g., providing a "best" value, along with an indication that the ultra-sonic thickness value for that reading may not be reliable).

As with all schematic flow diagrams and operational descriptions throughout the present disclosure, operations of procedure 4000 may be combined or divided, in whole or part, and/or certain operations may be omitted or added. Without limiting the present description, it is noted that operation 4022 to determine the secondary mode score value and operation 4024 to determine whether the secondary mode score value exceeds a utilization threshold may operate together such that operation 4018 to determine the secondary mode score is omitted. For example, where the secondary mode score value indicates that the secondary mode value is not sufficiently reliable to use as the ultra-sonic thickness value, in certain embodiments, processing to determine the secondary mode value are omitted. In certain embodiments, one or more of operations 4014 and/or 4008 to compare the primary mode score value to certain thresholds may additionally or alternatively include comparison of the primary mode score value to the secondary mode score value, and/or utilization of the secondary mode value instead of the primary mode value where the secondary mode score value is higher, or sufficiently higher, than the primary mode score value. In certain embodiments, both the primary mode value and the secondary mode value are determined and stored or communicated, for example to enhance future calibrations and/or processing operations, and/or to enable post-processing operations. In certain embodiments, one or more operations of procedure 4200 are performed by a controller 802.

Figure 43:
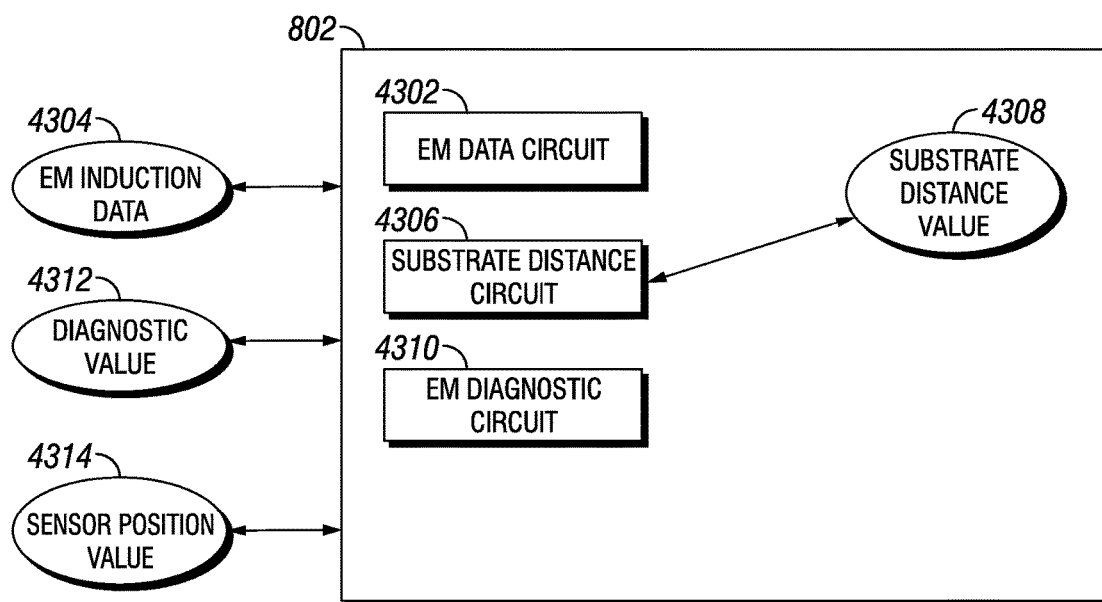
FIG. 43 is a schematic block diagram of an apparatus for utilizing EM induction data.

Referencing FIG. 43, an example apparatus 4300 for operating a magnetic induction sensor for an inspection robot is depicted. In certain embodiments, the magnetic induction sensor is mounted on a sled 1, and/or on a payload 2. In certain embodiments, the magnetic induction sensor is a lead sensor as described throughout the present disclosure, although operations of the apparatus 4300 for operating the magnetic induction sensor for the inspection robot include the magnetic induction sensor positioned on any payload and/or any logistical inspection operation runs. In certain embodiments, the magnetic induction sensor is a lead sensor and positioned on a same sled as an ultra-sonic or other sensor. In certain embodiments, the magnetic induction sensor is included on a payload 2 with other sensors, potentially including an ultra-sonic sensor, and may be on a same sled 1 or an offset sled (e.g., one or more magnetic sensors on certain sleds 1 of a payload 2, and ultra-sonic or other sensors on other sleds 1 of the payload 2).

An example apparatus 4300 includes an EM data circuit 4302 structured to interpret EM induction data 4304 provided by a magnetic induction sensor. The EM induction data 4304 provides an indication of the thickness of material, including coatings, debris, non-ferrous metal spray material (e.g., repair material), and/or damage, between the sensor and a substrate ferrous material, such as a pipe, tube, wall, tank wall, or other material provided as a substrate for an inspection surface. The foregoing operations of the EM data circuit 4302 and magnetic induction sensor are well known in the art, and are standard operations for determining automotive paint thickness or other applications. However, the environment for the inspection robot is not typical, and certain further improvements to operations are described herein.

In certain embodiments, an inspection robot includes sled configurations, including any configurations described throughout the present disclosure, to ensure expected contact, including proximity and/or orientation, between the inspection surface and the magnetic induction sensor. Accordingly, a magnetic induction sensor included on a sled 1 of the inspection robot in accordance with the present disclosure provides a reliable reading of distance to the substrate ferrous material. In certain embodiments, the apparatus 4300 includes a substrate distance circuit 4306 that determines a substrate distance value 4308 between the magnetic induction sensor and a ferrous substrate of the inspection surface. Additionally or alternatively, the substrate distance value 4308 may be a coating thickness, a delay line correction factor (e.g., utilized by a thickness processing circuit 3906), a total debris-coating distance, or other value determined in response to the substrate distance value 4308.

In certain embodiments, the controller 802 further includes an EM diagnostic circuit 4310 that supports one or more diagnostics in response to the substrate distance value 4308. An example diagnostic includes a diagnostic value 4312 (e.g., a rationality diagnostic value, or another value used for a diagnostic check), wherein the EM diagnostic circuit 4310 provides information utilized by the thickness processing circuit 3906, for example to a thickness processing circuit 3906. For example, the layer of coating, debris, or other material between the substrate of the inspection surface and an ultra-sonic sensor can affect the peak arrival times. In a further example, the layer of coating, debris, or other material between the substrate of the inspection surface and an ultra-sonic sensor can act to increase the effective delay line between the transducer of the ultra-sonic sensor and the inspection surface. In certain embodiments, the thickness processing circuit 3906 utilizes the rationality diagnostic value 4312 to adjust expected arrival times for the primary return and/or secondary return values, and/or to adjust a primary mode scoring value and/or a secondary mode score value.

In certain embodiments, the EM diagnostic circuit 4310 operates to determine a sensor position value 4314. In certain embodiments, the sensor position value 4314 provides a determination of the sensor distance to the substrate. In certain embodiments, the sensor position value 4314 provides a rationality check whether the sensor is positioned in proximity to the inspection surface. For example, an excursion of the EM induction data 4304 and/or substrate distance value 4308 may be understood to be a loss of contact of the sensor with the inspection surface, and/or may form a part of a determination, combined with other information such as an arm 20, sled 1, or payload 2 position value, a value of any of the pivots 16, 17, 18, and/or information from a camera or other visual indicator, to determine that a sled 1 including the magnetic induction sensor, and/or the magnetic induction sensor, is not properly positioned with regard to the inspection surface. Additionally or alternatively, a thickness processing circuit 3906 may utilize the sensor position value 4314 to adjust the primary mode scoring value and/or the secondary mode score value—for example to exclude or label data that is potentially invalid. In certain embodiments, the sensor position value 4314 is utilized on a payload 2 having both an ultra-sonic sensor and a magnetic induction sensor, and/or on a sled 1 having both an ultra-sonic sensor and a magnetic induction sensor (e.g., where the sensor position value 4314 is likely to provide direct information about the ultra-sonic sensor value). In certain embodiments, the sensor position value 4314 is utilized when the magnetic induction sensor is not on a same payload 2 or sled 1 with an ultra-sonic sensor—for example by correlating with position data to identify a potential obstacle or other feature on the inspection surface that may move the sled 1 out of a desired alignment with the inspection surface. In certain embodiments, the sensor position value 4314 is utilized when the magnetic induction sensor is not on a same payload 2 or sled 1 with an ultra-sonic sensor, and is combined with other data in a heuristic check to determine if the ultra-sonic sensor (and/or related sled or payload) experiences the same disturbance at the same location that the magnetic induction sensor (and/or related sled or payload) experienced.

In certain embodiments, the substrate distance value 4308 is provided to a thickness processing circuit 3906, which utilizes the substrate distance value 4308 to differentiate between a utilization of the primary mode value 3908 and/or the secondary mode value 3916. For example, the thickness of a coating on the inspection surface can affect return times and expected peak times. Additionally or alternatively, where the speed of sound through the coating is known or estimated, the peak analysis of the primary mode value 3908 and/or the secondary mode value 3916 can be adjusted accordingly. For example, the secondary mode value 3916 will demonstrate additional peaks, which can be resolved with a knowledge of the coating thickness and material, and/or the speed of sound of the coating material can be resolved through deconvolution and frequency analysis of the returning peaks if the thickness of the coating is known. In another example, the primary mode value 3908 can be adjusted to determine a true substrate first peak response (which will, in certain embodiments, occur after a return from the coating surface), which can be resolved with a knowledge of the coating thickness and/or the speed of sound of the coating material. In certain embodiments, a likely composition of the coating material is known—for example based upon prior repair operations performed on the inspection surface. In certain embodiments, as described, sound characteristics of the coating material, and/or effective sound characteristics of a pseudo-material (e.g., a mix of more than one material modeled as an aggregated pseudo-material) acting as the aggregate of the coating, debris, or other matter on the substrate of the inspection surface, can be determined through an analysis of the ultra-sonic data and/or coupled with knowledge of the thickness of the matter on the substrate of the inspection surface.

Figure 44:
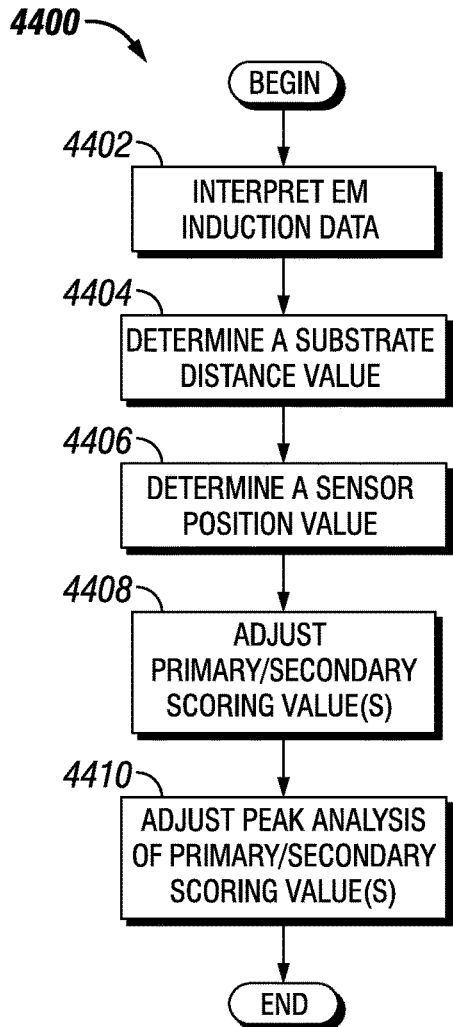
FIG. 44 is a schematic flow diagram of a procedure to utilize EM induction data.

Referencing FIG. 44, an example procedure 4400 for operating and analyzing a magnetic induction sensor on an inspection robot is schematically depicted. The example procedure 4400 includes an operation 4402 to interpret EM induction data provided by a magnetic induction sensor, and an operation 4404 to determine a substrate distance value between the magnetic induction sensor and a ferrous substrate of the inspection surface. The example procedure 4400 further includes an operation 4406 to determine a sensor position value, such as: a sensor distance from a substrate of the inspection surface; and/or a sensor pass/fail orientation, alignment or position check. In certain embodiments, the example procedure 4400 further includes an operation 4408 to adjust a primary mode scoring value and/or a secondary mode score value in response to the substrate distance value and/or the sensor position value. In certain embodiments, operation 4408 includes an operation to set the primary mode scoring value and/or secondary mode score value to a value that excludes the primary mode value and/or the secondary mode value from being used, and/or labels the primary mode value and/or the secondary mode value as potentially erroneous. In certain embodiments, operation 4410 determines a reliability of the primary mode value and/or the secondary mode value—for example where sonic properties of the matter between the ultra-sonic sensor and the inspection surface substrate are determined with a high degree of reliability—and the reliability determined from operation 4410 for the primary mode value and/or the secondary mode value is utilized to adjust the primary mode scoring value and/or the secondary mode score value. An example procedure 4400 further includes an operation 4410 to adjust a peak analysis of a primary mode value and/or a secondary mode value in response to the substrate distance value and/or the sensor position value. In certain embodiments, one or more operations of procedure 4400 are performed by a controller 802.

Figure 45:
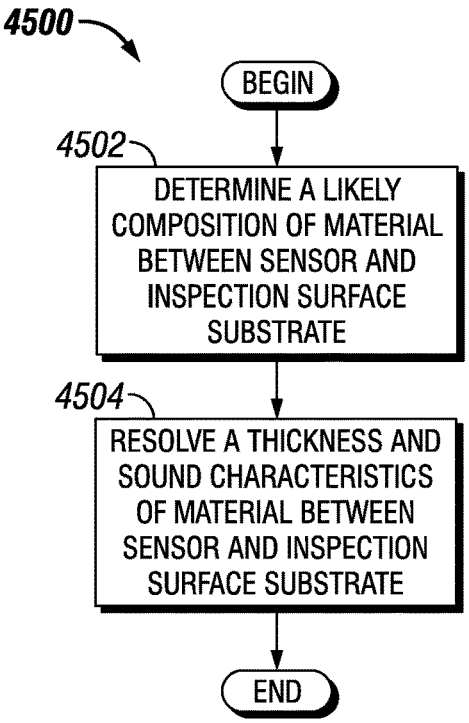
FIG. 45 is a schematic flow diagram of a procedure to determine a coating thickness and composition.

Referencing FIG. 45, an example procedure 4410 to adjust a peak analysis of a primary mode value and/or a secondary mode value is schematically depicted. The example procedure 4410 includes an operation 4504 to resolve a thickness and a sound characteristic of material positioned between a substrate of an inspection surface and an ultra-sonic sensor. In certain embodiments, operation 4504 includes a deconvolution of peak values including a frequency analysis of peaks observed in view of the substrate distance value and/or the sensor position value. In certain embodiments, the example procedure 4410 further includes an operation 4502 to determine a likely composition of the coating material—for example in response to a defined parameter by an inspection operator, and/or a previously executed repair operation on the inspection surface. In certain embodiments, operations of any of procedure 4400 and/or procedure 4410 are performed in view of position information of the magnetic induction sensor, and/or correlating position information of the ultra-sonic sensor. In certain embodiments, one or more operations of procedure 4410 are performed by a controller 802.

Figure 46:
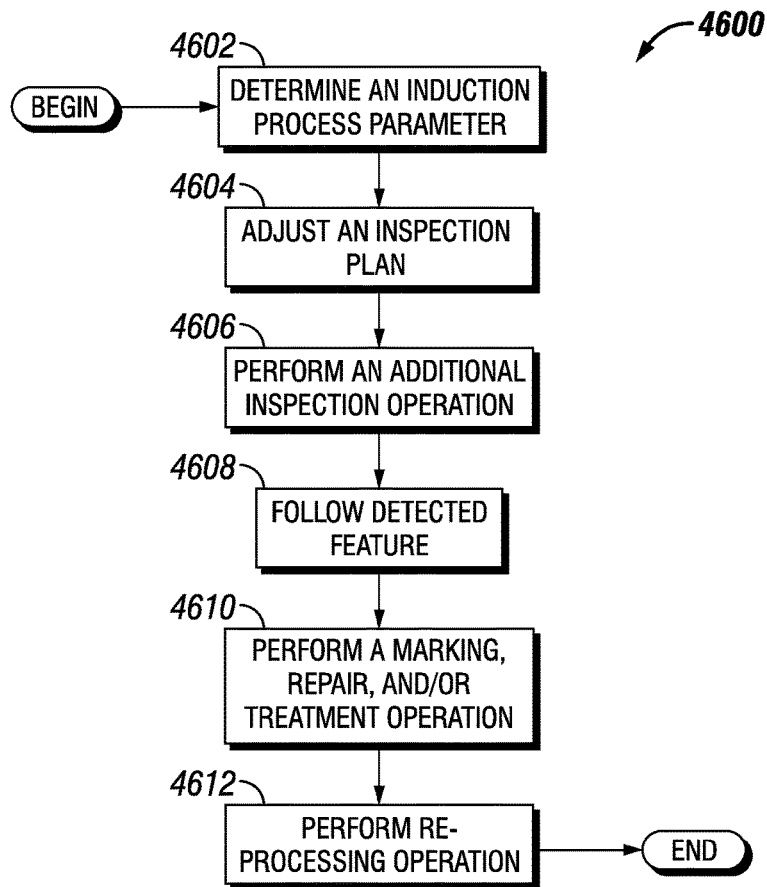
FIG. 46 is a schematic flow diagram of a procedure to re-process sensor data based on an induction process parameter.

Referencing FIG. 46, an example procedure 4600 to adjust an inspection operation in real-time in response to a magnetic induction sensor is schematically depicted. In certain embodiments, example procedure 4600 includes an operation 4602 to determine an induction processing parameter, such as a substrate distance value, a sensor position value, and/or a rationality diagnostic value. In certain embodiments, the example procedure 4600 includes an operation 4604 to adjust an inspection plan in response to the induction processing parameter. Example and non-limiting operations 4604 to an inspection plan include: adjusting a sensor calibration value (e.g., for an ultra-sonic sensor, a temperature sensor, etc.) for a sensor that may be affected by the coating, debris, or other matter between the magnetic induction sensor and a substrate of the inspection surface; adjusting an inspection resolution for one or more sensors for a planned inspection operation; adjusting a planned inspection map display for an inspection operation, and/or including adjusting sensors, sled positions, and/or an inspection robot trajectory to support the planned inspection map display; adjusting an inspection robot trajectory (e.g., locations, paths, number of runs, and/or movement speed on the inspection surface); adjusting a number, type, and/or positioning (e.g., sled numbers, placement, and/or payload positions) for sensors for an inspection operation; adjusting a wheel magnet strength and/or wheel configuration of an inspection robot in response to the induction processing parameter (e.g., adjusting for an expected distance to a ferrous material, configuring the wheels to manage debris, etc.); adjusting a sled ramp configuration (e.g., sled ramp leading and/or following slope, shape, and/or depth); and/or adjusting a down force for a sled and/or sensor. Operations 4604 may be performed in real-time, such as a change of an inspection plan during inspection operations, and/or at design or set-up time, such as a change of a configuration for the inspection robot or any other aspects described herein before an inspection run, between inspection runs, or the like.

In certain embodiments, the example procedure 4600 includes an operation 4606 to perform an additional inspection operation in response to the induction processing parameter. For example, operation 4606 may include operations such as: inspecting additional portions of the inspection surface and/or increasing the size of the inspection surface (e.g., to inspect other portions of an industrial system, facility, and/or inspection area encompassing the inspection surface); to activate trailing payloads and/or a rear payload to perform the additional inspection operation; re-running an inspection operation over an inspection area that at least partially overlaps a previously inspected area; and/or performing a virtual additional inspection operation—for example re-processing one or more aspects of inspection data in view of the induction processing parameter.

In certain embodiments, the example procedure 4600 includes an operation 4608 to follow a detected feature, for example activating a sensor configured to detect the feature as the inspection robot traverses the inspection surface, and/or configuring the inspection robot to adjust a trajectory to follow the feature (e.g., by changing the robot trajectory in real-time, and/or performing additional inspection operations to cover the area of the feature). Example and non-limiting features include welds, grooves, cracks, coating difference areas (e.g., thicker coating, thinner coating, and/or a presence or lack of a coating). In certain embodiments, the example procedure 4600 includes an operation 4610 to perform at least one of a marking, repair, and/or treatment operation, for example marking features (e.g., welds, grooves, cracks, and/or coating difference areas), and/or performing a repair and/or treatment operation (e.g., welding, applying an epoxy, applying a cleaning operation, and/or applying a coating) appropriate for a feature. In certain embodiments, operation 4610 to perform a marking operation includes marking the inspection surface in virtual space—for example as a parameter visible on an inspection map but not physically applied to the inspection surface.

In certain embodiments, the example procedure 4600 includes an operation 4612 to perform a re-processing operation in response to the induction processing parameter. For example, and without limitation, acoustic raw data, primary mode values and/or primary mode score values, and/or secondary mode values and/or secondary mode score values may be recalculated over at least a portion of an inspection area in response to the induction processing parameter. In certain embodiments, ultra-sonic sensor calibrations may be adjusted in a post-processing operation to evaluate, for example, wall thickness and/or imperfections (e.g., cracks, deformations, grooves, etc) utilizing the induction processing parameter(s).

Operations for procedure 4600 are described in view of an induction processing parameter for clarity of description. It is understood that a plurality of induction processing parameters, including multiple parameter types (e.g., coating presence and/or coating thickness) as well as a multiplicity of parameter determinations (e.g., position based induction processed values across at least a portion of the inspection surface) are likewise contemplated herein. In certain embodiments, one or more operations of procedure 4600 are performed by a controller 802.

Figure 47:
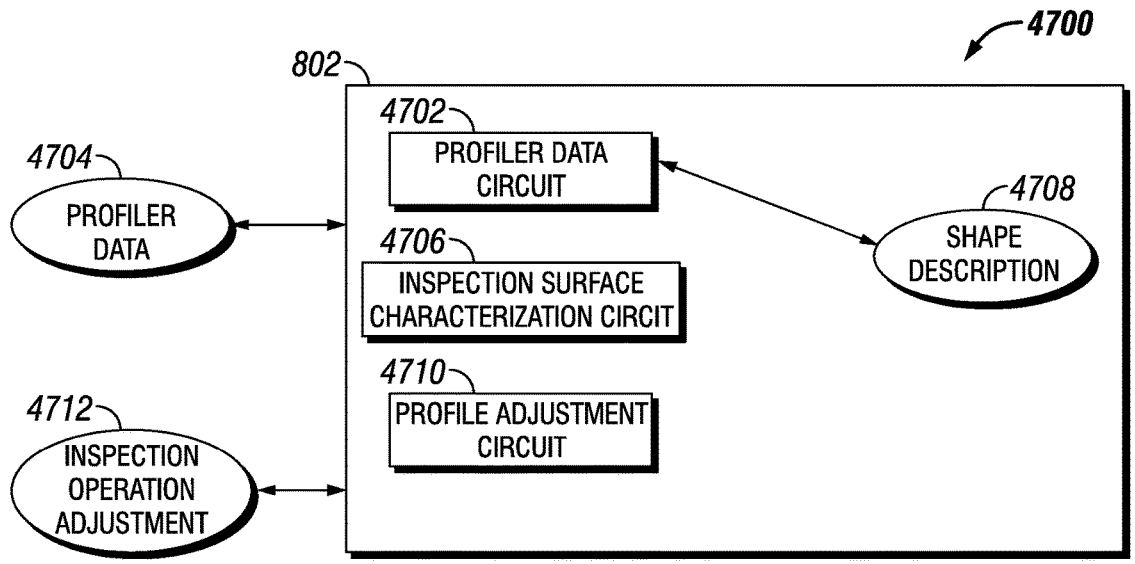
FIG. 47 is a schematic block diagram of a procedure to utilize a shape description.

Referencing FIG. 47, an example apparatus 4700 for utilizing a profiling sensor on an inspection robot is schematically depicted. Example and non-limiting profiling sensors include a laser profiler (e.g., a high spatial resolution laser beam profiler) and/or a high resolution caliper log. A profiling sensor provides for a spatial description of the inspection surface—for example variations in a pipe 502 or other surface can be detected, and/or a high resolution contour of at least a portion of the inspection surface can be determined. In certain embodiments, a controller 802 includes a profiler data circuit 4702 that interprets profiler data 4704 provided by the profiling sensor. The example controller 802 further includes an inspection surface characterization circuit 4706 that provides a characterization of the shape of the inspection surface in response to the profiler data—for example as a shape description 4708 of the inspection surface, including anomalies, variations in the inspection surface geometry, and/or angles of the inspection surface (e.g., to determine a perpendicular angle to the inspection surface). The example controller 802 further includes a profile adjustment circuit 4710 that provides an inspection operation adjustment 4712 in response to the shape description 4708. Example and non-limiting inspection operation adjustments 4712 include: providing an adjustment to a sled, payload, and/or sensor orientation within a sled (e.g., to provide for a more true orientation due to a surface anomaly, including at least changing a number and configuration of sleds on a payload, configuring a payload to avoid an obstacle, adjusting a down force of a sled, arm, sensor, and/or payload, and/or adjusting a shape of a sled bottom surface); a change to a sensor resolution value (e.g., to gather additional data in the vicinity of an anomaly or shape difference of the inspection surface); a post-processing operation (e.g., re-calculating ultra-sonic and/or magnetic induction data—for example in response to a shape of the inspection surface, and/or in response to a real orientation of a sensor to the inspection surface—such as correcting for oblique angles and subsequent sonic and/or magnetic effects); a marking operation (e.g., marking an anomaly, shape difference, and/or detected obstacle in real space—such as on the inspection surface—and/or in virtual space such as on an inspection map); and/or providing the inspection operation adjustment 4712 as an instruction to a camera to capture an image of an anomaly and/or a shape difference.

Figure 48:
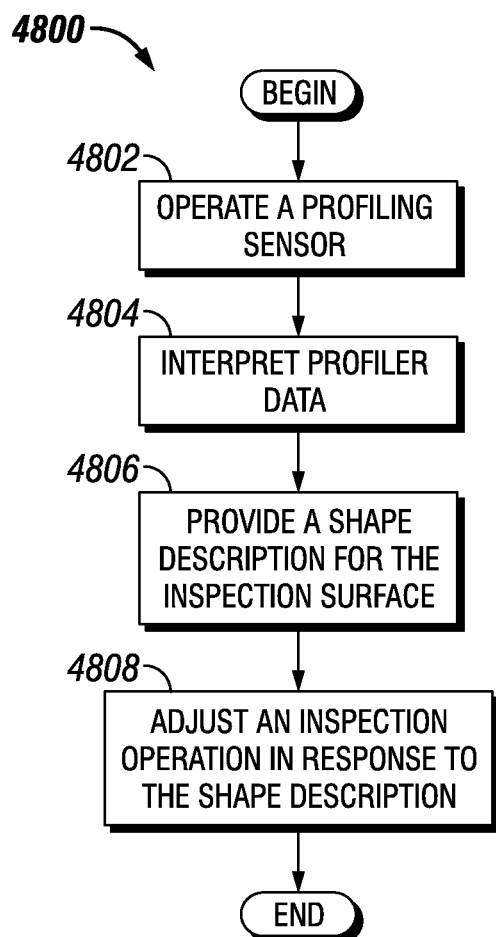
FIG. 48 is a schematic flow diagram of a procedure to adjust an inspection operation in response to profiler data.

Referencing FIG. 48, an example procedure 4800 for utilizing a profiling sensor on an inspection robot is schematically depicted. The example procedure 4800 includes an operation 4802 to operate a profiling sensor on at least a portion of an inspection surface, and an operation 4804 to interpret profiler data in response to the operation 4802. The example procedure 4800 further includes an operation 4806 to characterize a shape of the inspection surface, and/or thereby provide a shape description for the inspection surface, and an operation 4808 to adjust an inspection operation in response to the shape of the inspection surface.

An example system includes: an inspection robot including a plurality of payloads; a plurality of arms, wherein each of the plurality of arms is pivotally mounted to one of the plurality of payloads; a plurality of sleds, wherein each sled is pivotally mounted to one of the plurality of arms; and a plurality of sensors, wherein each sensor is mounted to a corresponding one of the sleds such that the sensor is operationally couplable to an inspection surface in contact with a bottom surface of the corresponding one of the sleds.

Certain further aspects of an example system are described following, any one or more of which may be included in certain embodiments of the example system.

An example system may further include wherein the bottom surface of the corresponding one of the sleds is contoured in response to a shape of the inspection surface.

An example system may further include wherein the inspection surface includes a pipe outer wall, and wherein the bottom surface of the corresponding one of the sleds includes a concave shape.

An example system may further include wherein the bottom surface of the corresponding one of the sleds includes at least one shape selected from the shapes consisting of: a concave shape, a convex shape, and a curved shape.

An example system may further include wherein each of the plurality of arms is further pivotally mounted to the one of the plurality of payloads with two degrees of rotational freedom.

An example system may further include wherein the sleds as mounted on the arms include three degrees of rotational freedom.

An example system may further include a biasing member coupled to each one of the plurality of arms, and wherein the biasing member provides a biasing force to corresponding one of the plurality of sleds, wherein the biasing force is directed toward the inspection surface.

An example system may further include wherein each of the plurality of payloads has a plurality of the plurality of arms mounted thereon.

An example system includes an inspection robot, and a plurality of sleds mounted to the inspection robot; a plurality of sensors, wherein each sensor is mounted to a corresponding one of the sleds such that the sensor is operationally couplable to an inspection surface in contact with a bottom surface of the corresponding one of the sleds; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include a couplant entry for the couplant chamber, wherein the couplant entry is positioned between the cone tip portion and the sensor mounting end.

An example system may further include wherein the couplant entry is positioned at a vertically upper side of the cone when the inspection robot is positioned on the inspection surface.

An example system may further include wherein the couplant exit opening includes one of flush with the bottom surface and extending through the bottom surface.

An example system includes an inspection robot including a plurality of payloads; a plurality of arms, wherein each of the plurality of arms is pivotally mounted to one of the plurality of payloads; a plurality of sleds, wherein each sled is mounted to one of the plurality of arms; a plurality of sensors, wherein each sensor is mounted to a corresponding one of the sleds such that the sensor is operationally couplable to an inspection surface in contact with a bottom surface of the corresponding one of the sleds; a couplant chamber disposed within each of the plurality of sleds, each couplant chamber interposed between a transducer of the sensor mounted to the sled and the inspection surface; and a biasing member coupled to each one of the plurality of arms, and wherein the biasing member provides a biasing force to corresponding one of the plurality of sleds, wherein the biasing force is directed toward the inspection surface.

Certain further aspects of an example system are described following, any one or more of which may be included in certain embodiments of the example system.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include a couplant entry for the couplant chamber, wherein the couplant entry is positioned between the cone tip portion and the sensor mounting end.

An example system may further include wherein the couplant entry is positioned at a vertically upper side of the cone when the inspection robot is positioned on the inspection surface.

An example system may further include wherein the couplant exit opening includes one of flush with the bottom surface and extending through the bottom surface.

An example system may further include wherein each payload includes a single couplant connection to the inspection robot.

An example method includes providing an inspection robot having a plurality of payloads and a corresponding plurality of sleds for each of the payloads; mounting a sensor on each of the sleds, each sensor mounted to a couplant chamber interposed between the sensor and an inspection surface, and each couplant chamber including a couplant entry for the couplant chamber; changing one of the plurality of payloads to a distinct payload; and wherein the changing of the plurality of payloads does not include disconnecting a couplant line connection at the couplant chamber.

An example method includes providing an inspection robot having a plurality of payloads and a corresponding plurality of sleds for each of the payloads; mounting a sensor on each of the sleds, each sensor mounted to a couplant chamber interposed between the sensor and an inspection surface, and each couplant chamber including a couplant entry for the couplant chamber; changing one of the plurality of payloads to a distinct payload; and wherein the changing of the plurality of payloads does not include dismounting any of the sensors from corresponding couplant chambers.

An example system includes: an inspection robot including a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled defines a chamber sized to accommodate a sensor.

Certain further aspects of an example system are described following, any one or more of which may be included in certain embodiments of the example system.

An example system may further include a plurality of sensors, wherein each sensor is positioned in one of the chambers of a corresponding one of the plurality of sleds.

An example system may further include wherein each chamber further includes a stop, and wherein each of the plurality of sensors is positioned against the stop.

An example system may further include wherein each sensor positioned against the stop has a predetermined positional relationship with a bottom surface of the corresponding one of the plurality of sleds.

An example system may further include wherein each chamber further includes a chamfer on at least one side of the chamber.

An example system may further include wherein each sensor extends through a corresponding holding clamp, and wherein each holding clamp is mounted to the corresponding one of the plurality of sleds.

An example system may further include wherein each of the plurality of sleds includes an installation sleeve positioned at least partially within in the chamber.

An example system may further include wherein each of the plurality of sleds includes an installation sleeve positioned at least partially within in the chamber, and wherein each sensor positioned in one of the chambers engages the installation sleeve positioned in the chamber.

An example system may further include wherein each of the plurality of sensors is positioned at least partially within an installation sleeve, and wherein each installation sleeve is positioned at least partially within the chamber of the corresponding one of the plurality of sleds.

An example system may further include wherein each chamber further includes wherein each of the plurality of sensors includes an installation tab, and wherein each of the plurality of sensors positioned in one of the chambers engages the installation tab.

An example system may further include wherein each installation tab is formed by relief slots.

An example system includes: an inspection robot including a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled includes a bottom surface; and a removable layer positioned on each of the bottom surfaces.

Certain further aspects of an example system are described following, any one or more of which may be included in certain embodiments of the example system.

An example system may further include wherein the removable layer includes a sacrificial film.

An example system may further include wherein the sacrificial film includes an adhesive backing on a side of the sacrificial film that faces the bottom surface.

An example system may further include wherein the removable layer includes a hole positioned vertically below a chamber of the corresponding one of the plurality of sleds.

An example system may further include wherein the removable layer is positioned at least partially within a recess of the bottom surface.

An example system may further include wherein the removable layer includes a thickness providing a selected spatial orientation between an inspection contact side of the removable layer and the bottom surface.

An example system includes: an inspection robot including a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled includes an upper portion and a replaceable lower portion having a bottom surface.

Certain further aspects of an example system are described following, any one or more of which may be included in certain embodiments of the example system.

An example system may further include wherein the replaceable lower portion includes a single, 3-D printable material.

An example system may further include wherein the upper portion and the replaceable lower portion are configured to pivotally engage and disengage.

An example system may further include wherein the bottom surface further includes at least one ramp.

An example method includes interrogating an inspection surface with an inspection robot having a plurality of sleds, each sled including an upper portion and a replaceable lower portion having a bottom surface; determining that the replaceable lower portion of one of the sleds is one of damaged or worn; and in response to the determining, disengaging the worn or damaged replaceable portion from the corresponding upper portion, and engaging a new or undamaged replaceable portion to the corresponding upper portion.

An example method may further include wherein the disengaging includes turning the worn or damaged replaceable portion relative to the corresponding upper portion.

An example method may further include performing a 3-D printing operation to provide the new or undamaged replaceable portion.

An example method includes determining a surface characteristic for an inspection surface; providing a replaceable lower portion having a bottom surface, the replaceable lower portion including a lower portion of a sled having an upper portion, wherein the sled includes one of a plurality of sleds for an inspection robot; and wherein the providing includes one of performing a 3-D printing operation or selecting one from a multiplicity of pre-configured replaceable lower portions.

Certain further aspects of an example system are described following, any one or more of which may be included in certain embodiments of the example system.

An example method may further include determining the surface characteristic includes determining a surface curvature of the inspection surface.

An example method may further include providing includes providing the replaceable lower portion having at least one of a selected bottom surface shape or at least one ramp.

An example method may further include wherein the at least one ramp includes at least one of a ramp angle and a ramp total height value.

An example system includes an inspection robot including a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled includes a bottom surface defining a ramp.

Certain further aspects of an example system are described following, any one or more of which may be included in certain embodiments of the example system.

An example system may further include wherein each sled further includes the bottom surface defining two ramps, wherein the two ramps include a forward ramp and a rearward ramp.

An example system may further include wherein the ramp include at least one of a ramp angle and a ramp total height value.

An example system may further include wherein the at least one of the ramp angle and the ramp total height value are configured to traverse an obstacle on an inspection surface to be traversed by the inspection robot.

An example system may further include wherein the ramp includes a curved shape.

An example system includes an inspection robot including a plurality of payloads; a plurality of arms, wherein each of the plurality of arms is mounted to one of the plurality of payloads; a plurality of sleds, wherein each sled is pivotally mounted to one of the plurality of arms; and a plurality of sensors, wherein each sensor is mounted to a corresponding one of the sleds such that the sensor is operationally couplable to an inspection surface in contact with a bottom surface of the corresponding one of the sleds.

Certain further aspects of an example system are described following, any one or more of which may be included in certain embodiments of the example system.

An example system may further include wherein each sled is pivotally mounted to one of the plurality of arms at a selected one of a plurality of pivot point positions.

An example system may further include a controller configured to select the one of the plurality of pivot point positions during an inspection run of the inspection robot.

An example system may further include wherein the controller is further configured to select the one of the plurality of pivot point positions in response to a travel direction of the inspection robot.

An example system may further include wherein each sled is pivotally mounted to one of the plurality of arms at a plurality of pivot point positions.

An example method includes providing a plurality of sleds for an inspection robot, each of the sleds mountable to a corresponding arm of the inspection robot at a plurality of pivot point positions; determining which of the plurality of pivot point positions is to be utilized for an inspection operation; and pivotally mounting each of the sleds to the corresponding arm at a selected one of the plurality of pivot point positions in response to the determining.

Certain further aspects of an example method are described following, any one or more of which may be included in certain embodiments of the example method.

An example method may further include wherein the pivotally mounting is performed before an inspection run by the inspection robot.

An example method may further include wherein the pivotally mounting is performed during an inspection run by the inspection robot.

An example method may further include wherein the pivotally mounting is performed in response to a travel direction of the inspection robot.

An example method may further include pivotally mounting each of the sleds at a selected plurality of the plurality of pivot point positions in response to the determining.

An example method includes determining an inspection resolution for an inspection surface; configuring an inspection robot by providing a plurality of horizontally distributed sensors operationally coupled to the inspection robot in response to the inspection resolution; and performing an inspection operation on the inspection surface at a resolution at least equal to the inspection resolution.

One or more certain further aspects of the example method may be incorporated in certain embodiments. Performing the inspection operation may include interrogating the inspection surface acoustically utilizing the plurality of horizontally distributed sensors. The plurality of horizontally distributed sensors may be provided on a first payload of the inspection robot, and wherein the configuring the inspection robot further enhances at least one of a horizontal sensing resolution or a vertical sensing resolution of the inspection robot by providing a second plurality of horizontally distributed sensors on a second payload of the inspection robot. The inspection robot may include providing the first payload defining a first horizontal inspection lane and the second payload defining a second horizontal inspection lane. The inspection robot may include providing the first payload and the second payload such that the first horizontal inspection lane is distinct from the second horizontal inspection lane. The inspection robot may include providing the first payload and the second payload such that the first horizontal inspection lane at least partially overlaps the second horizontal inspection lane. The inspection robot may include determining an inspection trajectory of the inspection robot over the inspection surface, such as the inspection trajectory determining a first inspection run and a second inspection run, wherein a first area of the inspection surface traversed by the first inspection run at least partially overlaps a second area of the inspection surface traversed by the second inspection run.

An example system includes an inspection robot including at least one payload; a plurality of arms, wherein each of the plurality of arms is pivotally mounted to the at least one payload; and a plurality of sleds, wherein each sled is pivotally mounted to one of the plurality of arms, and wherein the plurality of sleds are distributed horizontally across the payload.

One or more certain further aspects of the example system may be incorporated in certain embodiments. The plurality of sleds may be distributed across the payload with a spacing defining a selected horizontal sensing resolution of the inspection robot. The sleds may be distributed across the payload, wherein a plurality of sleds are provided within a horizontal distance that is less than a horizontal width of a pipe to be inspected. There may be a plurality of sensors, wherein each sensor is mounted to a corresponding one of the sleds such that the sensor is operationally couplable to an inspection surface in contact with a bottom surface of the corresponding one of the sleds. At least one payload may include a first payload and a second payload, and wherein the first payload and the second payload define distinct horizontal inspection lanes for the inspection surface. There may be a plurality of sensors including ultra-sonic sensors, and wherein each of the plurality of payloads comprises a single couplant connection to the inspection robot.

An example system includes an inspection robot having a number of sensors operationally coupled thereto; and a means for horizontally distributing the number of sensors across a selected horizontal inspection lane of an inspection surface. In a further aspect, a plurality of the number of sensors may be provided to inspect a single pipe of the inspection surface at a plurality of distinct horizontal positions of the pipe.

An example system includes an inspection robot comprising a first payload and a second payload; a first plurality of arms pivotally mounted to the first payload, and a second plurality of arms pivotally mounted to the second payload; a first plurality of sleds mounted to corresponding ones of the first plurality of arms, and a second plurality of sleds mounted to corresponding ones of the second plurality of arms; wherein the first payload defines a first horizontal inspection lane for an inspection surface, and wherein the second payload defines a second horizontal inspection lane for the inspection surface; and wherein the first horizontal inspection lane at least partially overlaps the second horizontal inspection lane.

One or more certain further aspects of the example system may be incorporated in certain embodiments. At least one of the second plurality of sleds may be horizontally aligned with at least one of the first plurality of sleds. There may be a plurality of sensors, wherein each sensor is mounted to a corresponding one of the first plurality of sleds and the second plurality of sleds, such that the sensor is operationally couplable to an inspection surface in contact with a bottom surface of the corresponding one of the first plurality of sleds and the second plurality of sleds. Sensors may be mounted on the horizontally aligned sleds for interrogating vertically distinct portions of the inspection surface. At least one of the second plurality of sleds and at least one of the first plurality of sleds may be horizontally offset. The first payload may include a forward payload and wherein the second payload comprises a rear payload. The first payload may include a forward payload and wherein the second payload comprises a trailing payload.

An example apparatus includes an inspection data circuit structured to interpret lead inspection data from a lead sensor; a sensor configuration circuit structured to determine a configuration adjustment for a trailing sensor in response to the lead inspection data; and a sensor operation circuit structured to adjust at least one parameter of the trailing sensor in response to the configuration adjustment.

One or more certain further aspects of the example apparatus may be incorporated in certain embodiments. The inspection data circuit may be further structured to interpret trailing sensor data from a trailing sensor, wherein the trailing sensor is responsive to the configuration adjustment. The configuration adjustment may include at least one adjustment selected from the adjustments consisting of: changing of sensing parameters of the trailing sensor; changing a cut-off time to observe a peak value for an ultra-sonic trailing sensor; enabling operation of a trailing sensor; adjusting a sensor sampling rate of a trailing sensor; adjusting a fault cut-off values for a trailing sensor; adjusting a sensor range of a trailing sensor; adjusting a resolution value of a trailing sensor; changing a movement speed of an inspection robot, wherein the trailing sensors are operationally coupled to the inspection robot. The lead sensor and the trailing sensor may be operationally coupled to an inspection robot. The lead sensor may include a first sensor during a first inspection run, and wherein the trailing sensor comprises the first sensor during a second inspection run. The inspection data circuit may be further structured to interpret the lead inspection data and interpret the trailing sensor data in a single inspection run.

An example system may include an inspection robot; a lead sensor operationally coupled to the inspection robot and structured to provide lead inspection data; a controller, the controller including: an inspection data circuit structured to interpret the lead inspection data; a sensor configuration circuit structured to determine a configuration adjustment for a trailing sensor in response to the lead inspection data; and a sensor operation circuit structured to adjust at least one parameter of the trailing sensor in response to the configuration adjustment; and a trailing sensor responsive to the configuration adjustment.

One or more certain further aspects of the example system may be incorporated in certain embodiments. The controller may be at least partially positioned on the inspection robot. The inspection data circuit may be further structured to interpret trailing inspection data from the trailing sensor. The configuration adjustment may include at least one adjustment selected from the adjustments consisting of: changing of sensing parameters of the trailing sensor; wherein the trailing sensor comprises an ultra-sonic sensor, and changing a cut-off time to observe a peak value for the trailing sensor; enabling operation of the trailing sensor; adjusting a sensor sampling rate of the trailing sensor; adjusting a fault cut-off values for the trailing sensor; adjusting a sensor range of the trailing sensor; adjusting a resolution value of the trailing sensor; changing a movement speed of the inspection robot, wherein the trailing sensor is operationally coupled to the inspection robot. The trailing sensor may be operationally coupled to an inspection robot. The lead sensor may include a first sensor during a first inspection run, and wherein the trailing sensor comprises the first sensor during a second inspection run. The inspection data circuit may be further structured to interpret the lead inspection data and interpret the trailing inspection data in a single inspection run.

An example method may include interpreting a lead inspection data from a lead sensor; determining a configuration adjustment for a trailing sensor in response to the lead inspection data; and adjusting at least one parameter of a trailing sensor in response to the configuration adjustment.

One or more certain further aspects of the example method may be incorporated in certain embodiments. A trailing inspection data may be interpreted from the trailing sensor. The adjusting the at least one parameter of the trailing sensor may include at least one adjustment selected from the adjustments consisting of: changing of sensing parameters of the trailing sensor; changing a cut-off time to observe a peak value for an ultra-sonic trailing sensor; enabling operation of a trailing sensor; adjusting a sensor sampling rate of a trailing sensor; adjusting a fault cut-off values for a trailing sensor; adjusting a sensor range of a trailing sensor; adjusting a resolution value of a trailing sensor; changing a movement speed of an inspection robot, wherein the trailing sensors are operationally coupled to the inspection robot. Interpreting the lead sensor data may be provided during a first inspection run, and interpreting the trailing inspection data during a second inspection run. Interpreting the lead inspection data and interpreting the trailing inspection data may be performed in a single inspection run.

An example method includes accessing an industrial system comprising an inspection surface, wherein the inspection surface comprises a personnel risk feature; operating an inspection robot to inspect at least a portion of the inspection surface; and wherein the operating the inspection is performed with at least a portion of the industrial system providing the personnel risk feature still operating.

One or more certain further aspects of the example method may be incorporated in certain embodiments. The personnel risk feature may include a portion of the inspection surface having an elevated height. The elevated height may include at least one height value consisting of the height values selected from: at least 10 feet, at least 20 feet, at least 30 feet, greater than 50 feet, greater than 100 feet, and up to 150 feet. The personnel risk feature may include an elevated temperature of at least a portion of the inspection surface. The personnel risk feature may include an enclosed space, and wherein at least a portion of the inspection surface is positioned within the enclosed space. The personnel risk feature may include an electrical power connection. Determining a position of the inspection robot within the industrial system during the operating the inspection robot, and shutting down only a portion of the industrial system during the inspection operation in response to the position of the inspection robot.

An example system includes an inspection robot comprising a payload; a plurality of arms, wherein each of the plurality of arms is pivotally mounted to the payload; and a plurality of sleds, wherein each sled is pivotally mounted to one of the plurality of arms, thereby configuring a horizontal distribution of the plurality of sleds.

One or more certain further aspects of the example system may be incorporated in certain embodiments. There may be a plurality of sensors, wherein each sensor is mounted to a corresponding one of the sleds such that the sensor is operationally couplable to an inspection surface in contact with a bottom surface of the corresponding one of the sleds. The horizontal distribution of the plurality of sleds may provide for a selected horizontal resolution of the plurality of sensors. A controller may be configured to determine the selected horizontal resolution and to configure a position of the plurality of arms on the payload in response to the selected horizontal resolution. The horizontal distribution of the plurality of sleds may provide for avoidance of an obstacle on an inspection surface to be traversed by the inspection robot. A controller may be configured to configure a position of the plurality of arms on the payload in response to the obstacle on the inspection surface, and to further configure the position of the plurality of arms on the payload in response to a selected horizontal resolution after the inspection robot clears the obstacle.

An example method includes determining at least one of an obstacle position on an inspection surface and a selected horizontal resolution for sensors to be utilized for operating an inspection robot on an inspection surface; and configuring a horizontal distribution of a plurality of sleds on a payload of the inspection robot in response to the at least one of the obstacle position and the selected horizontal resolution.

One or more certain further aspects of the example method may be incorporated in certain embodiments. The configuring of the horizontal distribution may be performed before an inspection run of the inspection robot on the inspection surface. The configuring of the horizontal distribution may be performed during inspection operations of the inspection robot on the inspection surface.

An example system includes an inspection robot including at least one payload; a plurality of arms, wherein each of the plurality of arms is pivotally mounted to the at least one payload; a plurality of sleds, wherein each sled is pivotally mounted to one of the plurality of arms, and wherein the plurality of sleds are distributed horizontally across the payload; and wherein a plurality of the sleds are provided within a horizontal distance that is less than a horizontal width of a pipe to be inspected.

One or more certain further aspects of the example system may be incorporated in certain embodiments. An acoustic sensor may be mounted to each of the plurality of sleds provided within the horizontal distance less than a horizontal width of the pipe to be inspected. The plurality of sleds may be provided within the horizontal distance less than a horizontal width of the pipe to be inspected oriented such that each of the acoustic sensors is perpendicularly oriented toward the pipe to be inspected. A sensor mounted to each of the plurality of sleds may be provided within the horizontal distance less than a horizontal width of the pipe to be inspected. The plurality of sleds may be provided within the horizontal distance less than a horizontal width of the pipe to be inspected oriented such that each of the sensors is perpendicularly oriented toward the pipe to be inspected.

An example system includes an inspection robot including at least one payload; a plurality of arms, wherein each of the plurality of arms is pivotally mounted to the at least one payload; a plurality of sleds, wherein each sled is pivotally mounted to one of the plurality of arms; and a plurality of sensors mounted on each of the plurality of sleds.

One or more certain further aspects of the example system may be incorporated in certain embodiments. The plurality of sensors on each of the plurality of sleds may be vertically separated. A vertically forward one of the plurality of sensors may be mounted on each of the plurality of sleds comprises a lead sensor, and wherein a vertically rearward one of the plurality of sensors comprises a trailing sensor.

An example system includes a first payload having a first plurality of sensors mounted thereupon, and a second payload having a second plurality of sensors mounted thereupon; an inspection robot; and one of the first payload and the second payload mounted upon the inspection robot, thereby defining a sensor suite for the inspection robot.

One or more certain further aspects of the example system may be incorporated in certain embodiments. A mounted one of the first payload and the second payload may include a single couplant connection to the inspection robot. A mounted one of the first payload and the second payload may include a single electrical connection to the inspection robot.

An example method includes determining a sensor suite for inspection operations of an inspection robot; selecting a payload for the inspection robot from a plurality of available payloads in response to the determined sensor suite; and mounting the selected payload to the inspection robot.

One or more certain further aspects of the example method may be incorporated in certain embodiments. The inspection operations may be performed with the inspection robot after the mounting. The mounting may comprise connecting a single couplant connection between the selected payload and the inspection robot. The mounting may include connecting a single electrical connection between the selected payload and the inspection robot. The mounting may include dis-mounting a previously mounted payload from the inspection robot before the mounting, where the dis-mounting may disconnect a single couplant connection between the previously mounted payload and the inspection robot, disconnect a single electrical connection between the previously mounted payload and the inspection robot, and the like. The mounting may include connecting a single electrical connection between the selected payload and the inspection robot.

An example system includes an inspection robot comprising a plurality of payloads; a plurality of arms, wherein each of the plurality of arms is pivotally mounted to one of the plurality of payloads; a plurality of sleds, wherein each sled is pivotally mounted to one of the plurality of arms; a plurality of sensors, wherein each sensor is mounted to a corresponding one of the sleds such that the sensor is operationally couplable to an inspection surface in contact with a bottom surface of the corresponding one of the sleds; and a biasing member disposed within each of the sleds, wherein the biasing member provides a down force to the corresponding one of the plurality of sensors.

One or more certain further aspects of the example system may be incorporated in certain embodiments. The biasing member may include at least one member selected from the members consisting of a leaf spring, a cylindrical spring, a torsion spring, and an electromagnet. A controller may be configured to adjust a biasing strength of the biasing member. The controller may be further configured to interpret a distance value between the corresponding one of the plurality of sensors and an inspection surface, and to further adjust the biasing strength of the biasing member in response to the distance value.

An example method includes providing a fixed acoustic path between a sensor coupled to an inspection robot and an inspection surface; filling the acoustic path with a couplant; and acoustically interrogating the inspection surface with the sensor.

One or more certain further aspects of the example system may be incorporated in certain embodiments. The filling of the acoustic path with the couplant may include injecting the couplant into the fixed acoustic path from a vertically upper direction. Determining that the sensor should be re-coupled to the inspection surface. Performing a re-coupling operation in response to the determining. Lifting the sensor from the inspection surface, and returning the sensor to the inspection surface. Increasing a flow rate of the filling the acoustic path with the couplant. Performing at least one operation selected from the operations consisting of: determining that a predetermined time has elapsed since a last re-coupling operation; determining that an event has occurred indicating that a re-coupling operation is desired; and determining that the acoustic path has been interrupted.

An example system includes an inspection robot, and a plurality of sleds mounted to the inspection robot; a plurality of sensors, wherein each sensor is mounted to a corresponding one of the sleds such that the sensor is operationally couplable to an inspection surface in contact with a bottom surface of the corresponding one of the sleds; a couplant chamber disposed within each of the plurality of sleds, each couplant chamber interposed between a transducer of the sensor mounted to the sled and the inspection surface; wherein each couplant chamber comprises a cone, the cone comprising a cone tip portion at an inspection surface end of the cone, and a sensor mounting end opposite the cone tip portion, and wherein the cone tip portion defines a couplant exit opening.

One or more certain further aspects of the example system may be incorporated in certain embodiments, such as a plurality of payloads may be mounted to the inspection robot; a plurality of arms, wherein each of the plurality of arms is pivotally mounted to one of the plurality of payloads; wherein the plurality of sleds are each mounted to one of the plurality of arms; and a biasing member coupled to at least one of: one of the payloads or one of the arms; and wherein the biasing member provides a down force on one of the sleds corresponding to the one of the payloads or the one of the arms.

An example system includes an inspection robot, and a plurality of sleds mounted to the inspection robot; a plurality of sensors, wherein each sensor is mounted to a corresponding one of the sleds such that the sensor is operationally couplable to an inspection surface in contact with a bottom surface of the corresponding one of the sleds; a couplant chamber disposed within each of the plurality of sleds, each couplant chamber interposed between a transducer of the sensor mounted to the sled and the inspection surface; and a means for providing a low fluid loss of couplant from each couplant chamber.

An example system includes an inspection robot having a number of sleds mounted to the inspection robot (e.g., mounted on arms coupled to payloads). The example system further includes a number of sensors, where each sensor is mounted on one of the sleds—although in certain embodiments, each sled may have one or more sensors, or no sensors. The example system includes the sensors mounted on the sleds such that the sensor is operationally couplable to the inspection surface when a bottom surface of the corresponding sled is in contact with the inspection surface. For example, the sled may include a hole therethrough, a chamber such that when the sensor is mounted in the chamber, the sensor is in a position to sense parameters about the inspection surface, or any other orientation as described throughout the present disclosure. The example system further includes a couplant chamber disposed within a number of the sleds—for example in two or more of the sleds, in a horizontally distributed arrangement of the sleds, and/or with a couplant chamber disposed in each of the sleds. In certain embodiments, sleds may alternate with sensor arrangements—for example a magnetic induction sensor in a first sled, an acoustic sensor with a couplant chamber in a second sled, another magnetic induction sensor in third sled, an acoustic sensor with a couplant chamber in a fourth sled, and so forth. Any pattern or arrangement of sensors is contemplated herein. In certain embodiments, a magnetic induction sensor is positioned in a forward portion of a sled (e.g., as a lead sensor) and an acoustic sensor is positioned in a middle or rearward portion of the sled (e.g., as a trailing sensor). In certain embodiments, arms for sleds having one type of sensor are longer and/or provide for a more forward position than arms for sleds having a second type of sensor.

The example system further includes each couplant chamber provided as a cone, with the cone having a cone tip portion at an inspection surface end of the cone, and a sensor mounting end opposite the inspection surface end. An example cone tip portion defines a couplant exit opening. An example system further includes a couplant entry for each couplant chamber, which may be positioned between the cone tip portion and the sensor mounting end. In certain embodiments, the couplant entry is positioned at a vertically upper side of the cone in an intended orientation of the inspection robot on the inspection surface. For example, if the inspection robot is intended to be oriented on a flat horizontal inspection surface, the couplant entry may be positioned above the cone or at an upper end of the cone. In another example, if the inspection robot is intended to be oriented on a vertical inspection surface, the couplant entry may be positioned on a side of the cone, such as a forward side (e.g., for an ascending inspection robot) or a rearward side (e.g., for a descending inspection robot). The vertical orientation of the couplant entry, where present, should not be confused with a vertical or horizontal arrangement of the inspection robot (e.g., for sensor distribution orientations). In certain embodiments, a horizontal distribution of sensors is provided as perpendicular, and/or at an oblique angle, to a travel path of the inspection robot, which may be vertical, horizontal, or at any other angle in absolute geometric space.

Certain further aspects of an example system are described following, any one or more of which may be present in certain embodiments. An example system includes a controller 802 configured to fill the couplant chamber with a couplant—for example by providing a couplant command (e.g., flow rate, couplant rate, injection rate, and/or pump speed command) to a couplant pump which may be present on the inspection robot and/or remote from the inspection robot (e.g., providing couplant through a tether). In certain embodiments, the couplant pump is responsive to the couplant command to provide the couplant, to the inspection robot, to a payload, and/or to individual sleds (and thereby to the couplant chamber via the couplant chamber entry). In certain embodiments, the couplant command is a couplant injection command, and the couplant pump is responsive to the injection command to inject the couplant into the couplant chamber. In certain embodiments, the controller is further configured to determine that at least one of the sensors should be re-coupled to the inspection surface. Example and non-limiting operations to determine that at least one of the sensors should be re-coupled to the inspection surface include: determining that a predetermined time has elapsed since a last re-coupling operation; determining that an event has occurred indicating that a re-coupling operation is desired; and/or determining that the acoustic path has been interrupted. In certain embodiments, the controller provides a re-coupling instruction in response to determining that one or more sensors should be re-coupled to the inspection surface. Example and non-limiting re-coupling instructions include a sensor lift command—for example to lift the sensor(s) of a payload and/or arm briefly to clear bubbles from the couplant chamber. In certain embodiments, an actuator such as a motor, push-rod, and/or electromagnet, is present on the inspection robot to lift a payload, an arm, and/or tilt a sled in response to the sensor lift command. In certain embodiments, ramps or other features on a sled are configured such that the sled lifts (or tilts) or otherwise exposes the couplant exit opening—for example in response to a reversal of the direction of motion for the inspection robot. In a further embodiment, the inspection robot is responsive to the sensor lift command to briefly change a direction of motion and thereby perform the re-coupling operation. In certain embodiments, the controller is configured to provide the re-coupling instruction as an increased couplant injection command—for example to raise the couplant flow rate through the couplant chamber and thereby clear bubbles or debris.

An example procedure includes an operation to provide a fixed acoustic path (e.g., a delay line) between a sensor coupled to an inspection robot and an inspection surface. The example procedure includes an operation to fill the acoustic path with couplant, and to acoustically interrogate the inspection surface with the sensor. Certain further aspects of the example procedure are described following, any one or more of which may be present in certain embodiments. An example procedure further includes an operation to fill the acoustic path with the couplant by injecting the couplant into the fixed acoustic path from a vertically upper direction. An example procedure further includes an operation to determine that the sensor should be re-coupled to the surface, and/or to perform a re-coupling operation in response to the determining. In certain further embodiments, example operations to perform a re-coupling operation include at least: lifting the sensor from the inspection surface, and returning the sensor to the inspection surface; and/or increasing a flow rate of the filling of the acoustic path with the couplant. Example operations to determine the sensor should be re-coupled to the surface include at least: determining that a predetermined time has elapsed since a last re-coupling operation; determining that an event has occurred indicating that a re-coupling operation is desired; and determining that the acoustic path has been interrupted.

An example procedure includes performing an operation to determine an inspection resolution for an inspection surface (e.g., by determining a likely resolution that will reveal any features of interest such as damage or corrosion, and/or to meet a policy or regulatory requirement); an operation to configure an inspection robot by providing a number of horizontally distributed acoustic sensors operationally coupled to the inspection robot (e.g., mounted to be moved by the inspection robot, and/or with couplant or other fluid provisions, electrical or other power provisions, and/or with communication provisions); an operation to provide a fixed acoustic path between the acoustic sensors and the inspection surface; an operation to fill the acoustic path with a couplant; and an operation to perform an inspection operation on the inspection surface with the acoustic sensors. It will be understood that additional sensors beyond the acoustic sensors may be operationally coupled to the inspection robot in addition to the acoustic sensors.

Certain further aspects of an example procedure are described following, any one or more of which may be present in certain embodiments. An example procedure includes an operation to perform the inspection operation on the inspection surface at a resolution at least equal to an inspection resolution, and/or where the inspection resolution is smaller (e.g., higher resolution) than a spacing of the horizontally distributed acoustic sensors (e.g., the procedure provides for a greater resolution than that provided by the horizontally spacing of the sensors alone). An example procedure includes the operation to fill the acoustic path with the couplant including injecting the couplant into the fixed acoustic path from a vertically upper direction, and/or an operation to determine that at least one of the acoustic sensors should be re-coupled to the inspection surface.

An example system includes an inspection robot having a plurality of wheels, wherein the plurality of wheels are positioned to engage an inspection surface when the inspection robot is positioned on the inspection surface; wherein each of the plurality of wheels comprises a magnetic hub portion interposed between enclosure portions; wherein the enclosure portions extend past the magnetic hub portion and thereby prevent contact of the magnetic hub portion with the inspection surface.

One or more certain further aspects of the example system may be incorporated in certain embodiments. The enclosure portions may define a channel therebetween. A shape of the channel may be provided in response to a shape of a feature on the inspection surface. The shape of the channel may correspond to a curvature of the feature of the inspection surface. An outer covering for each of the enclosure portions may be provided, such as where the outer covering for each of the enclosure portions define a channel therebetween. The ferrous enclosure portions may include one of an outer chamfer and an outer curvature, and wherein the one of the outer chamfer and the outer curvature correspond to a shape of a feature on the inspection surface. The enclosure portions may include ferrous enclosure portions.

An example system includes an inspection robot having a plurality of wheels, wherein the plurality of wheels are positioned to engage an inspection surface when the inspection robot is positioned on the inspection surface; wherein each of the plurality of wheels comprises a magnetic hub portion interposed between enclosure portions; and wherein the inspection robot further comprises a gear box motively coupled to at least one of the wheels, and wherein the gear box comprises at least one thrust washer axially interposed between two gears of the gear box.

An example system includes an inspection robot having a plurality of wheels, wherein the plurality of wheels are positioned to engage an inspection surface when the inspection robot is positioned on the inspection surface; wherein each of the plurality of wheels comprises a magnetic hub portion interposed between enclosure portions; and wherein the inspection robot further comprises a gear box motively coupled to at least one of the wheels, and wherein the gear box comprises gears that are not a ferromagnetic material.

An example system includes an inspection robot having a plurality of wheels, wherein the plurality of wheels are positioned to engage an inspection surface when the inspection robot is positioned on the inspection surface; wherein each of the plurality of wheels comprises a magnetic hub portion interposed between enclosure portions; and wherein the inspection robot further comprises a gear box motively coupled to at least one of the wheels, and a means for reducing magnetically induced axial loads on gears of the gear box.

An example system includes an inspection robot, and a plurality of sleds mounted to the inspection robot; a plurality of acoustic sensors, wherein each acoustic sensor is mounted to a corresponding one of the sleds such that the sensor is operationally couplable to an inspection surface in contact with a bottom surface of the corresponding one of the sleds; and a couplant chamber disposed within each of the plurality of sleds, each couplant chamber interposed between a transducer of the acoustic sensor mounted to the sled and the inspection surface.

Certain further aspects of an example system are described following, any one or more of which may be included in certain embodiments of the example system.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include a couplant entry for the couplant chamber, wherein the couplant entry is positioned between the cone tip portion and the sensor mounting end.

An example system may further include wherein the couplant entry is positioned at a vertically upper side of the cone when the inspection robot is positioned on the inspection surface.

An example system may further include wherein each sled includes a couplant connection conduit, wherein the couplant connection conduit is coupled to a payload couplant connection at an upstream end, and coupled to the couplant entry of the cone at a downstream end.

An example method includes providing a sled for an inspection robot, the sled including an acoustic sensor mounted thereon and a couplant chamber disposed within the sled, and the couplant chamber having a couplant entry; coupling the sled to a payload of the inspection robot at an upstream end of a couplant connection conduit, the couplant connection conduit coupled to the couplant entry at a downstream end.

Certain further aspects of an example method are described following, any one or more of which may be included in certain embodiments of the example method.

An example method may further include de-coupling the sled from the payload of the inspection robot, and coupling a distinct sled to the payload of the inspection robot, without disconnecting the couplant connection conduit from the couplant entry.

An example apparatus includes a controller, the controller including: a position definition circuit structured to interpret position information for an inspection robot on an inspection surface; a data positioning circuit structured to interpret inspection data from the inspection robot, and to correlate the inspection data to the position information to determine position informed inspection data; and wherein the data positioning circuit is further structured to provide the position informed inspection data as one of additional inspection data or updated inspection data.

Certain further aspects of an example apparatus are described following, any one or more of which may be included in certain embodiments of the example apparatus.

An example apparatus may further include wherein the position information includes one of relative position information or absolute position information.

An example apparatus may further include wherein the position definition circuit is further structured to determine the position information according to at least one of: global positioning service (GPS) data; an ultra-wide band radio frequency (RF) signal; a LIDAR measurement; a dead reckoning operation; a relationship of the inspection robot position to a reference point; a barometric pressure value; and a known sensed value correlated to a position of the inspection robot.

An example apparatus may further include wherein the position definition circuit is further structured to interpret a plant shape value, to determine a definition of a plant space including the inspection surface in response to the plant shape value, and to correlate the inspection data with a plant position information (e.g., into plant position values) in response to the definition of the plant space and the position information.

An example method includes: interpreting position information for an inspection robot on an inspection surface; interpreting inspection data from the inspection robot; correlating the inspection data to the position information to determine position informed inspection data; and providing the position informed inspection data as one of additional inspection data or updated inspection data.

Certain further aspects of an example method are described following, any one or more of which may be included in certain embodiments of the example method.

An example method may further include updating the position information for the inspection robot, and correcting the position informed inspection data.

An example method may further include wherein the position information includes position information determined at least partially in response to a dead reckoning operation, and wherein the updated position information is determined at least partially in response to feedback position operation.

An example method may further include determining a plant definition value, and to determine plant position values in response to the plant definition value and the position information.

An example method may further include providing the position informed inspection data further in response to the plant position values.

An example apparatus includes: an inspection data circuit structured to interpret inspection data from an inspection robot on an inspection surface; a robot positioning circuit structured to interpret position data for the inspection robot; and an inspection visualization circuit structured to determine an inspection map in response to the inspection data and the position data, and to provide at least a portion of the inspection map for display to a user.

Certain further aspects of an example apparatus are described following, any one or more of which may be included in certain embodiments of the example apparatus.

An example apparatus may further include wherein the inspection visualization circuit is further responsive structured to interpret a user focus value, and to update the inspection map in response to the user focus value.

An example apparatus may further include wherein the inspection visualization circuit is further responsive structured to interpret a user focus value, and to provide focus data in response to the user focus value.

An example apparatus may further include wherein the inspection map includes a physical depiction of the inspection surface.

An example apparatus may further include the inspection map further includes a visual representation of at least a portion of the inspection data depicted on the inspection surface.

An example apparatus may further include wherein the inspection map includes a virtual mark for a portion of the inspection surface.

An example apparatus includes: an acoustic data circuit structured to interpret return signals from an inspection surface to determine raw acoustic data; a thickness processing circuit structured to determine a primary mode score value in response to the raw acoustic data, and in response to the primary mode score value exceeding a predetermined threshold, determining a primary mode value corresponding to a thickness of the inspection surface material.

Certain further aspects of an example apparatus are described following, any one or more of which may be included in certain embodiments of the example apparatus.

An example apparatus may further include wherein the thickness processing circuit is further structured to determine, in response to the primary mode score value not exceeding the predetermined threshold, a secondary mode score value in response to the raw acoustic data.

An example apparatus may further include wherein the thickness processing circuit is further structured to determine, in response to the secondary mode score value exceeding a threshold, a secondary mode value corresponding to a thickness of the inspection surface material.

An example apparatus may further include wherein the thickness processing circuit is further structured to determine the primary mode score value in response to at least one parameter selected from the parameters consisting of: a time of arrival for a primary return; a time of arrival for a secondary return; a character of a peak for the primary return; a character of a peak for the secondary return; a sensor alignment determination for an acoustic sensor providing the return signals; a sled position for a sled having the acoustic sensor mounted thereupon; and a couplant anomaly indication.

An example apparatus may further include wherein the secondary mode value including a value determined from a number of reflected peaks of the return signals.

An example apparatus may further include wherein the raw acoustic data includes a lead inspection data, the apparatus further including: a sensor configuration circuit structured to determine a configuration adjustment for a trailing sensor in response to the lead inspection data; and a sensor operation circuit structured to adjust at least one parameter of the trailing sensor in response to the configuration adjustment; and a trailing sensor responsive to the configuration adjustment.

An example apparatus may further include wherein the acoustic data circuit is further structured to interpret trailing inspection data from the trailing sensor.

An example apparatus may further include wherein the configuration adjustment includes at least one adjustment selected from the adjustments consisting of: changing of sensing parameters of the trailing sensor; wherein the trailing sensor includes an ultra-sonic sensor, and changing a cut-off time to observe a peak value for the trailing sensor; enabling operation of the trailing sensor; adjusting a sensor sampling rate of the trailing sensor; adjusting a fault cut-off value for the trailing sensor; adjusting a sensor range of the trailing sensor; adjusting a resolution value of the trailing sensor; changing a movement speed of an inspection robot, wherein the trailing sensor is operationally coupled to the inspection robot.

An example apparatus may further include wherein a lead sensor providing the lead inspection data includes a first sensor during a first inspection run, and wherein the trailing sensor includes the first sensor during a second inspection run.

An example apparatus may further include wherein the acoustic data circuit is further structured to interpret the lead inspection data and interpret the trailing inspection data in a single inspection run.

An example apparatus may further include the wherein the raw acoustic data includes a lead inspection data, the apparatus further including: a sensor configuration circuit structured to determine a configuration adjustment in response to the lead inspection data, and wherein the configuration includes an instruction to utilize at least one of a consumable, a slower, or a more expensive trailing operation in response to the lead inspection data.

An example apparatus may further include wherein the trailing operation includes at least one operation selected from the operations consisting of: a sensing operation; a repair operation; and a marking operation.

An example apparatus includes: an electromagnetic (EM) data circuit structured to interpret EM induction data provided by a magnetic induction sensor; a substrate distance circuit structured to determine a substrate distance value between the magnetic induction sensor and a ferrous substrate of an inspection surface; and an EM diagnostic circuit structured to provide a diagnostic value in response to the substrate distance value.

Certain further aspects of an example apparatus are described following, any one or more of which may be included in certain embodiments of the example apparatus.

An example apparatus may further include wherein the diagnostic value includes at least one value selected from the values consisting of: a rationality check indicating whether the sensor is positioned in proximity to the inspection surface; and a sensor position value indicating a distance from a second sensor to the substrate of the inspection surface.

An example apparatus may further include: an acoustic data circuit structured to interpret return signals from the inspection surface to determine raw acoustic data; a thickness processing circuit structured to: determine a primary mode score value in response to the raw acoustic data and further in response to the rationality check; and in response to the primary mode score value exceeding a predetermined threshold, determining a primary mode value corresponding to a thickness of the inspection surface material.

An example apparatus may further include: an acoustic data circuit structured to interpret return signals from the inspection surface to determine raw acoustic data; a thickness processing circuit structured to: determine a primary mode score value in response to the raw acoustic data and further in response to the sensor position value; and in response to the primary mode score value exceeding a predetermined threshold, determining a primary mode value corresponding to a thickness of the inspection surface material.

An example apparatus may further include: an acoustic data circuit structured to interpret return signals from the inspection surface to determine raw acoustic data; a thickness processing circuit structured to: determine a primary mode score value in response to the raw acoustic data and further in response to the diagnostic value; and in response to the primary mode score value exceeding a predetermined threshold, determining a primary mode value corresponding to a thickness of the inspection surface material.

An example method includes: determining an induction processing parameter; and adjusting an inspection plan for an inspection robot in response to the induction processing parameter.

Certain further aspects of an example method are described following, any one or more of which may be included in certain embodiments of the example method.

An example method may further include wherein the induction processing parameter includes at least one parameter selected from the parameters consisting of: a substrate distance value, a sensor position value, and a rationality diagnostic value.

An example method may further include wherein the adjusting the inspection plan includes at least one operation selected from the operations consisting of: adjusting a sensor calibration value; adjusting a trailing sensor calibration value; adjusting an inspection resolution value for a sensor used in the inspection plan; adjusting at least one of a number, a type, or a positioning of a plurality of sensors used in the inspection plan; adjusting an inspection trajectory of the inspection robot; adjusting a sled ramp configuration for the inspection robot; adjusting a down force for a sled of the inspection robot; and adjusting a down force for a sensor of the inspection robot.

An example method may further include performing an additional inspection operation in response to the induction processing parameter.

An example method may further include wherein the adjusting includes adjusting an inspection trajectory of the inspection robot to follow a detected feature on an inspection surface.

An example method may further include wherein the detected feature includes at least one feature selected from the features consisting of: a weld, a groove, a crack, and a coating difference area.

An example method may further include an operation to respond to the detected feature.

An example method may further include wherein the operation to respond to the detected feature includes at least one operation selected from the operations consisting of: a repair operation; a treatment operation; a weld operation; an epoxy application operation; a cleaning operation; a marking operation; and a coating operation.

An example method may further include detecting a feature on the inspection surface, and marking the feature virtually on an inspection map.

An example method may further include detecting a feature on the inspection surface, and marking the feature with a mark not in the visible spectrum.

An example method may further include wherein the marking further includes utilizing at least one of an ultra-violet dye, a penetrant, and a virtual mark.

An example method includes: performing an inspection operation on an inspection surface, the inspection operation including an inspection surface profiling operation; determining a contour of at least a portion of the inspection surface in response to the surface profiling operation; and adjusting a calibration of an ultra-sonic sensor in response to the contour.

Certain further aspects of an example method are described following, any one or more of which may be included in certain embodiments of the example method.

An example method may further include wherein the adjusting is performed as a post-processing operation.

An example method includes: performing an inspection operation on an inspection surface, the inspection operation including interrogating the inspection surface with an electromagnetic sensor; determining an induction processing parameter in response to the interrogating; and adjusting a calibration of an ultra-sonic sensor in response to the induction processing parameter.

Certain further aspects of an example method are described following, any one or more of which may be included in certain embodiments of the example method.

An example method may further include wherein the adjusting is performed as a post-processing operation.

An example method includes: interpreting inspection data from an inspection robot on an inspection surface; interpreting position data for the inspection robot; and determining an inspection map in response to the inspection data and the position data, and providing at least a portion of the inspection map for display to a user.

Certain further aspects of an example method are described following, any one or more of which may be included in certain embodiments of the example method.

An example method may further include wherein the inspection map includes at least one parameter selected from the parameters consisting of: how much material should be added to the inspection surface; and a type of repair that should be applied to the inspection surface.

An example method may further include wherein the inspection map further includes an indication of a time until a repair of the inspection surface will be required.

An example method may further include accessing a facility wear model, and determining the time until a repair of the inspection surface will be required in response to the facility wear model.

An example method may further include wherein the inspection map further includes an indication a time that a repair of the inspection surface is expected to last.

An example method may further include accessing a facility wear model, and determining the time that the repair of the inspection surface is expected to last in response to the facility wear model.

An example method may further include determining the time that the repair of the inspection surface is expected to last in response to a type of repair to be performed.

An example method may further include presenting a user with a number of repair options, and further determining the time that the repair of the inspection surface is expected to last in response to a selected one of the number of repair options.

An example method includes accessing an industrial system comprising an inspection surface, wherein the inspection surface comprises a personnel risk feature; operating an inspection robot to inspect at least a portion of the inspection surface, wherein the operating the inspection is performed with at least a portion of the industrial system providing the personnel risk feature still operating; interpreting position information for the inspection robot on the inspection surface; interpreting inspection data from the inspection robot; correlating the inspection data to the position information to determine position informed inspection data; and providing the position informed inspection data as one of additional inspection data or updated inspection data.

An example system including an inspection robot with a sensor configuration circuit structured to determine a configuration adjustment for a trailing sensor in response to the lead inspection data; a sensor operation circuit structured to adjust at least one parameter of the trailing sensor in response to the configuration adjustment; and a trailing sensor responsive to the configuration adjustment, the inspection robot interpreting position information on an inspection surface, interpreting inspection data from the inspection robot, correlating the inspection data to the position information to determine position informed inspection data, and providing the position informed inspection data as one of additional inspection data or updated inspection data.

An example system including an inspection robot comprising at least one payload; a plurality of arms, wherein each of the plurality of arms is pivotally mounted to the at least one payload; a plurality of sleds, wherein each sled is pivotally mounted to one of the plurality of arms, wherein the plurality of sleds are distributed horizontally across the payload; and a plurality of sensors, wherein each sensor is mounted to a corresponding plurality of sleds such that the sensor is operationally couplable to an inspection surface in contact with a bottom surface of the plurality of sleds.

An example system including an inspection robot, and a plurality of sleds mounted to the inspection robot; a plurality of acoustic sensors, wherein each acoustic sensor is mounted to a corresponding one of the sleds such that the sensor is operationally couplable to an inspection surface in contact with a bottom surface of the corresponding one of the sleds; and a couplant chamber disposed within each of the plurality of sleds, each couplant chamber interposed between a transducer of the acoustic sensor mounted to the sled and the inspection surface; the inspection robot providing a fixed acoustic path between a sensor coupled to an inspection robot and an inspection surface, filling the acoustic path with a couplant, and acoustically interrogating the inspection surface with the sensor.

An example system including an inspection robot, and a plurality of sleds mounted to the inspection robot; a plurality of acoustic sensors, wherein each acoustic sensor is mounted to a corresponding one of the sleds such that the sensor is operationally couplable to an inspection surface in contact with a bottom surface of the corresponding one of the sleds; a couplant chamber disposed within each of the plurality of sleds, each couplant chamber interposed between a transducer of the acoustic sensor mounted to the sled and the inspection surface; wherein each couplant chamber comprises a cone, the cone comprising a cone tip portion at an inspection surface end of the cone, and a sensor mounting end opposite the cone tip portion, and wherein the cone tip portion defines a couplant exit opening.

An example system including an inspection robot, and a plurality of sleds mounted to the inspection robot; a plurality of sensors, wherein each sensor is mounted to a corresponding one of the sleds such that the sensor is operationally couplable to an inspection surface in contact with a bottom surface of the corresponding one of the sleds; a couplant chamber disposed within each of the plurality of sleds, each couplant chamber interposed between a transducer of the sensor mounted to the sled and the inspection surface, wherein each couplant chamber comprises a cone, the cone comprising a cone tip portion at an inspection surface end of the cone, and a sensor mounting end opposite the cone tip portion, and wherein the cone tip portion defines a couplant exit opening; the inspection robot providing a fixed acoustic path between a sensor coupled to an inspection robot and an inspection surface; filling the acoustic path with a couplant; and acoustically interrogating the inspection surface with the sensor.

A system, comprising: an inspection robot comprising a plurality of payloads; a plurality of arms, wherein each of the plurality of arms is pivotally mounted to one of the plurality of payloads; and a plurality of sleds, wherein each sled is pivotally mounted to one of the plurality of arms, wherein each sled comprises an upper portion and a replaceable lower portion having a bottom surface, and a plurality of sensors, wherein each sensor is mounted to a corresponding one of the sleds such that the sensor is operationally couplable to an inspection surface in contact with a bottom surface of the corresponding one of the sleds.

An example system including an inspection robot comprising at least one payload; a plurality of arms, wherein each of the plurality of arms is pivotally mounted to the at least one payload; a plurality of sleds, wherein each sled is pivotally mounted to one of the plurality of arms, and wherein the plurality of sleds are distributed horizontally across the payload; an acoustic data circuit structured to interpret return signals from an inspection surface to determine raw acoustic data; a thickness processing circuit structured to determine a primary mode score value in response to the raw acoustic data, and in response to the primary mode score value exceeding a predetermined threshold, determining a primary mode value corresponding to a thickness of the inspection surface material.

An example system including an inspection robot comprising at least one payload; a plurality of arms, wherein each of the plurality of arms is pivotally mounted to the at least one payload; a plurality of sleds, wherein each sled is pivotally mounted to one of the plurality of arms, and wherein the plurality of sleds are distributed horizontally across the payload; an electromagnetic (EM) data circuit structured to interpret EM induction data provided by a magnetic induction sensor; a substrate distance circuit structured to determine a substrate distance value between the magnetic induction sensor and a ferrous substrate of an inspection surface; and an EM diagnostic circuit structured to provide a diagnostic value in response to the substrate distance value.

An example system including an inspection robot comprising a plurality of payloads; a plurality of arms, wherein each of the plurality of arms is pivotally mounted to one of the plurality of payloads; a plurality of sleds, wherein each sled is pivotally mounted to one of the plurality of arms; a plurality of sensors, wherein each sensor is mounted to a corresponding one of the sleds such that the sensor is operationally couplable to an inspection surface in contact with a bottom surface of the corresponding one of the sleds; a biasing member disposed within each of the sleds, wherein the biasing member provides a down force to the corresponding one of the plurality of sensors; the inspection robot providing a fixed acoustic path between a sensor coupled to an inspection robot and an inspection surface, filling the acoustic path with a couplant, and acoustically interrogating the inspection surface with the sensor.

An example system includes an inspection robot having a plurality of wheels, wherein the plurality of wheels are positioned to engage an inspection surface when the inspection robot is positioned on the inspection surface; wherein each of the plurality of wheels comprises a magnetic hub portion interposed between enclosure portions; wherein the inspection robot further comprises a gear box motively coupled to at least one of the wheels, and wherein the gear box comprises at least one thrust washer axially interposed between two gears of the gear box; and wherein the enclosure portions extend past the magnetic hub portion and thereby prevent contact of the magnetic hub portion with the inspection surface.

An example system including an inspection robot comprising a plurality of payloads; a plurality of arms, wherein each of the plurality of arms is mounted to one of the plurality of payloads; a plurality of sleds, wherein each sled is pivotally mounted to one of the plurality of arms; a plurality of sensors, wherein each sensor is mounted to a corresponding one of the sleds such that the sensor is operationally couplable to an inspection surface in contact with a bottom surface of the corresponding one of the sleds, wherein each sled is pivotally mounted to one of the plurality of arms at a selected one of a plurality of pivot point positions; and a controller configured to select the one of the plurality of pivot point positions during an inspection run of the inspection robot, the controller configured to select the one of the plurality of pivot point positions in response to a travel direction of the inspection robot, wherein each sled is pivotally mounted to one of the plurality of arms at a plurality of pivot point positions.

An example system including an inspection data circuit structured to interpret lead inspection data from a lead sensor; a sensor configuration circuit structured to determine a configuration adjustment for a trailing sensor in response to the lead inspection data; a sensor operation circuit structured to adjust at least one parameter of the trailing sensor in response to the configuration adjustment;
the system interpreting inspection data from an inspection robot on an inspection surface; interpreting position data for the inspection robot; and determining an inspection map in response to the inspection data and the position data, and providing at least a portion of the inspection map for display to a user.

An example method including determining an inspection resolution for an inspection surface; configuring an inspection robot by providing a plurality of horizontally distributed sensors operationally coupled to the inspection robot in response to the inspection resolution; performing an inspection operation on the inspection surface at a resolution at least equal to the inspection resolution, wherein the plurality of horizontally distributed sensors are provided on a first payload of the inspection robot, and wherein the configuring the inspection robot further comprises enhancing at least one of a horizontal sensing resolution or a vertical sensing resolution of the inspection robot by providing a second plurality of horizontally distributed sensors on a second payload of the inspection robot; interpreting inspection data from the inspection robot on an inspection surface; interpreting position data for the inspection robot; and determining an inspection map in response to the inspection data and the position data, and providing at least a portion of the inspection map for display to a user.

An example system including an inspection robot comprising at least one payload; a plurality of arms, wherein each of the plurality of arms is pivotally mounted to the at least one payload; a plurality of sleds, wherein each sled is pivotally mounted to one of the plurality of arms; and a plurality of sensors mounted on each of the plurality of sleds; the inspection robot determining an induction processing parameter, and adjusting an inspection plan for an inspection robot in response to the induction processing parameter.

An example system including an inspection robot comprising at least one payload; a plurality of arms, wherein each of the plurality of arms is pivotally mounted to the at least one payload; a plurality of sleds, wherein each sled is pivotally mounted to one of the plurality of arms; a plurality of sensors mounted on each of the plurality of sleds; an inspection data circuit structured to interpret lead inspection data from a lead sensor; a sensor configuration circuit structured to determine a configuration adjustment for a trailing sensor in response to the lead inspection data; and a sensor operation circuit structured to adjust at least one parameter of the trailing sensor in response to the configuration adjustment.

An example system including an inspection robot comprising a plurality of payloads; a plurality of arms, wherein each of the plurality of arms is pivotally mounted to one of the plurality of payloads; a plurality of sleds, wherein each sled is pivotally mounted to one of the plurality of arms, and wherein each sled comprises a bottom surface; and a removable layer positioned on each of the bottom surfaces;
the inspection robot determining an induction processing parameter, and adjusting an inspection plan for an inspection robot in response to the induction processing parameter.

An example system including an inspection robot having a plurality of wheels, wherein the plurality of wheels are positioned to engage an inspection surface when the inspection robot is positioned on the inspection surface, wherein each of the plurality of wheels comprises a magnetic hub portion interposed between enclosure portions, wherein the enclosure portions extend past the magnetic hub portion and thereby prevent contact of the magnetic hub portion with the inspection surface, the inspection robot providing a fixed acoustic path between a sensor coupled to an inspection robot and an inspection surface, filling the acoustic path with a couplant, and acoustically interrogating the inspection surface with the sensor.

An example method includes: performing an inspection operation on an inspection surface, the inspection operation including an inspection surface profiling operation; detecting a feature on the inspection surface and marking the feature virtually on an inspection map; determining a contour of at least a portion of the inspection surface in response to the surface profiling operation; and adjusting a calibration of an ultra-sonic sensor in response to the contour.

Certain further aspects of an example method are described following, any one or more of which may be included in certain embodiments of the example method.

An example method may further include wherein the inspection operation includes interrogating the inspection surface with an electromagnetic sensor; determining an induction processing parameter in response to the interrogating; and further adjusting the calibration of the ultrasonic sensor in response to the induction processing parameter.

An example method may further include wherein the detected feature includes at least one feature selected from the features consisting of: a weld, a groove, a crack, and a coating difference area.

An example apparatus includes: an inspection data circuit structured to interpret inspection data from an inspection robot on an inspection surface; a robot positioning circuit structured to interpret position data for the inspection robot; an electromagnetic (EM) data circuit structured to interpret EM induction data provided by a magnetic induction sensor; a substrate distance circuit structured to determine a substrate distance value between the magnetic induction sensor and a ferrous substrate of an inspection surface; an EM diagnostic circuit structured to provide a diagnostic value in response to the substrate distance value; and an inspection visualization circuit structured to determine an inspection map in response to the inspection data and the position data, and to provide at least a portion of the inspection map for display to a user.

Certain further aspects of an example apparatus are described following, any one or more of which may be included in certain embodiments of the example apparatus.

An example apparatus may further include wherein the diagnostic value includes at least one value selected from the values consisting of: a rationality check indicating whether the sensor is positioned in proximity to the inspection surface; and a sensor position value indicating a distance from a second sensor to the substrate of the inspection surface.

An example apparatus may further include wherein the inspection visualization circuit is further responsively structured to interpret a user focus value, and to update the inspection map in response to the user focus value.

An example method includes: determining an inspection resolution for an inspection surface; configuring an inspection robot by providing a plurality of horizontally distributed sensors operationally coupled to the inspection robot in response to the inspection resolution; performing an inspection operation on the inspection surface at a resolution at least equal to the inspection resolution; interpreting inspection data from the inspection robot on the inspection surface; interpreting position data for the inspection robot; determining an inspection map in response to the inspection data and the position data; detecting a feature on the inspection surface and marking the feature virtually on the inspection map; and providing at least a portion of the inspection map for display to a user.

Certain further aspects of an example method are described following, any one or more of which may be included in certain embodiments of the example method.

An example method may further include wherein the performing the inspection operation includes interrogating the inspection surface acoustically utilizing the plurality of horizontally distributed sensors.

An example apparatus includes: a controller, the controller including: an electromagnetic (EM) data circuit structured to interpret EM induction data provided by a magnetic induction sensor; a substrate distance circuit structured to determine a substrate distance value between the magnetic induction sensor and a ferrous substrate of an inspection surface; an EM diagnostic circuit structured to provide a diagnostic value in response to the substrate distance value; a position definition circuit structured to interpret position information for an inspection robot on an inspection surface; and a data positioning circuit to correlate the substrate distance values to the position information to determine position informed substrate distance values and wherein the data positioning circuit is further structured to provide the position informed substrate distance values as one of additional inspection data or updated inspection data.

Certain further aspects of an example apparatus are described following, any one or more of which may be included in certain embodiments of the example apparatus.

An example apparatus may further include wherein the diagnostic value includes at least one value selected from the values consisting of: a rationality check indicating whether the sensor is positioned in proximity to the inspection surface; and a sensor position value indicating a distance from a second sensor to the substrate of the inspection surface.

An example apparatus may further include wherein the position definition circuit is further structured to determine the position information according to at least one of: global positioning service (GPS) data; an ultra-wide band radio frequency (RF) signal; a LIDAR measurement; a dead reckoning operation; a relationship of the inspection robot position to a reference point; a barometric pressure value; and a known sensed value correlated to a position of the inspection robot.

An example apparatus includes: an acoustic data circuit structured to interpret return signals from an inspection surface to determine raw acoustic data; a thickness processing circuit structured to determine a primary mode score value in response to the raw acoustic data, and in response to the primary mode score value exceeding a predetermined threshold, determining a primary mode value corresponding to a thickness of the inspection surface material; a robot positioning circuit structured to interpret position data for the inspection robot; and an inspection visualization circuit structured to determine an inspection map in response to the thickness of the inspection surface material and the position data, and to provide at least a portion of the inspection map for display to a user.

Certain further aspects of an example apparatus are described following, any one or more of which may be included in certain embodiments of the example apparatus.

An example apparatus may further include wherein the inspection visualization circuit is further structured to determine an inspection map in response to the primary mode score value.

An example apparatus may further include wherein the thickness processing circuit is further structured to determine, in response to the primary mode score value not exceeding the predetermined threshold, a secondary mode score value in response to the raw acoustic data.

An example method includes: accessing an industrial system including an inspection surface, wherein the inspection surface includes a personnel risk feature; operating an inspection robot to inspect at least a portion of the inspection surface, wherein the inspection robot has a plurality of wheels and wherein each of the plurality of wheels includes a magnetic hub portion interposed between enclosure portions, the enclosure portions extending past the magnetic hub portion and thereby preventing contact of the magnetic hub portion with the inspection surf; and wherein operating the inspection is performed with at least a portion of the industrial system providing the personnel risk feature still operating.

Certain further aspects of an example method are described following, any one or more of which may be included in certain embodiments of the example method.

An example method may further include wherein the personnel risk feature includes at least one of a portion of the inspection surface having an elevated height, an elevated temperature of at least a portion of the inspection surface, a portion of the inspection surface is positioned within the enclosed space, and an electrical power connection.

An example method may further include determining a position of the inspection robot within the industrial system during the operating the inspection robot, and shutting down only a portion of the industrial system during the inspection operation in response to the position of the inspection robot.

An example system includes: an inspection robot including: a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled includes a bottom surface; and a removable layer positioned on each of the bottom surfaces; and a controller, the controller including: an electromagnetic (EM) data circuit structured to interpret EM induction data provided by a magnetic induction sensor; a substrate distance circuit structured to determine a substrate distance value between the magnetic induction sensor and a ferrous substrate of an inspection surface; and an EM diagnostic circuit structured to provide a diagnostic value in response to the substrate distance value.

Certain further aspects of an example system are described following, any one or more of which may be included in certain embodiments of the example system.

An example system may further include wherein at least one of the sleds includes a magnetic induction sensor.

An example system may further include wherein the removable layer includes a thickness providing a selected spatial orientation between an inspection contact side of the removable layer and the bottom surface.

An example system may further include wherein the diagnostic value includes at least one value selected from the values consisting of: a rationality check indicating whether the sensor is positioned in proximity to the inspection surface; and a sensor position value indicating a distance from a second sensor to the substrate of the inspection surface.

An example system includes: an inspection robot including: at least one payload; a plurality of arms, wherein each of the plurality of arms is pivotally mounted to the at least one payload; a plurality of sleds, wherein each sled is pivotally mounted to one of the plurality of arms, and wherein the plurality of sleds are distributed horizontally across the payload; and wherein the horizontal distribution of the plurality of sleds provides for a selected horizontal resolution of the plurality of sensors.

An example system includes: an inspection robot including: a payload; a plurality of arms, wherein each of the plurality of arms is pivotally mounted to the payload; a plurality of sleds, wherein each sled is pivotally mounted to one of the plurality of arms, thereby configuring a horizontal distribution of the plurality of sleds; a plurality of sensors, wherein each sensor is mounted to a corresponding one of the sleds such that the sensor is operationally couplable to an inspection surface in contact with a bottom surface of the corresponding one of the sleds; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include wherein the horizontal distribution of the plurality of sleds provides for a selected horizontal resolution of the plurality of sensors.

An example system may further include a controller configured to determine the selected horizontal resolution and to configure a position of the plurality of arms on the payload in response to the selected horizontal resolution.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system includes: an inspection robot; a plurality of sleds mounted to the inspection robot, wherein each sled is pivotally mounted at a selected one of a plurality of pivot point positions; a plurality of sensors, wherein each sensor is mounted to a corresponding one of the sleds such that the sensor is operationally couplable to an inspection surface in contact with a bottom surface of the corresponding one of the sleds; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include a controller configured to select the one of the plurality of pivot point positions during an inspection run of the inspection robot.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system includes an inspection robot including a plurality of payloads; a plurality of arms, wherein each of the plurality of arms is pivotally mounted to one of the plurality of payloads; a plurality of sleds, wherein each sled is mounted to one of the plurality of arms at a selected one of a plurality of pivot point positions; a plurality of sensors, wherein each sensor is mounted to a corresponding one of the sleds such that the sensor is operationally couplable to an inspection surface in contact with a bottom surface of the corresponding one of the sleds; a couplant chamber disposed within each of the plurality of sleds, each couplant chamber interposed between a transducer of the sensor mounted to the sled and the inspection surface; and a biasing member coupled to each one of the plurality of arms, and wherein the biasing member provides a biasing force to corresponding one of the plurality of sleds, wherein the biasing force is directed toward the inspection surface.

An example system includes: an inspection robot, and a plurality of sleds mounted to the inspection robot; a plurality of sensors, wherein each sensor is mounted to a corresponding one of the sleds such that the sensor is operationally couplable to an inspection surface in contact with a bottom surface of the corresponding one of the sleds, wherein the bottom surface of the corresponding one of the sleds is contoured in response to a shape of the inspection surface; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include wherein the inspection surface includes a pipe outer wall, and wherein the bottom surface of the corresponding one of the sleds includes a concave shape.

An example system may further include wherein the bottom surface of the corresponding one of the sleds includes at least one shape selected from the shapes consisting of: a concave shape, a convex shape, and a curved shape.

An example system includes: an inspection robot including a plurality of payloads; a plurality of arms, wherein each of the plurality of arms is pivotally mounted to one of the plurality of payloads; a plurality of sleds, wherein each sled is mounted to one of the plurality of arms; a plurality of sensors, wherein each sensor is mounted to a corresponding one of the sleds such that the sensor is operationally couplable to an inspection surface in contact with a bottom surface of the corresponding one of the sleds, wherein the bottom surface of the corresponding one of the sleds is contoured in response to a shape of the inspection surface; a couplant chamber disposed within each of the plurality of sleds, each couplant chamber interposed between a transducer of the sensor mounted to the sled and the inspection surface; and a biasing member coupled to each one of the plurality of arms, and wherein the biasing member provides a biasing force to corresponding one of the plurality of sleds, wherein the biasing force is directed toward the inspection surface.

An example method includes: providing an inspection robot having a plurality of payloads and a corresponding plurality of sleds for each of the payloads, wherein the bottom surface of the corresponding one of the sleds is contoured in response to a shape of an inspection surface; mounting a sensor on each of the sleds, each sensor mounted to a couplant chamber interposed between the sensor and the inspection surface, and each couplant chamber including a couplant entry for the couplant chamber; changing one of the plurality of payloads to a distinct payload; and wherein the changing of the plurality of payloads does not include dismounting any of the sensors from corresponding couplant chambers.

An example system includes an inspection robot including a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled includes a bottom surface defining a ramp and wherein each sled defines a chamber sized to accommodate a sensor.

Certain further aspects of an example system are described following, any one or more of which may be included in certain embodiments of the example system.

An example system may further include wherein each chamber further includes a stop, and wherein each of the plurality of sensors is positioned against the stop.

An example system may further include wherein each sensor positioned against the stop has a predetermined positional relationship with a bottom surface of the corresponding one of the plurality of sleds.

An example system may further include wherein each sled further includes the bottom surface defining two ramps, wherein the two ramps include a forward ramp and a rearward ramp.

An example system may further include wherein the ramp include at least one of a ramp angle and a ramp total height value.

An example system may further include wherein the at least one of the ramp angle and the ramp total height value are configured to traverse an obstacle on an inspection surface to be traversed by the inspection robot.

An example system includes: an inspection robot including a plurality of payloads; a plurality of arms, wherein each of the plurality of arms is pivotally mounted to one of the plurality of payloads; and a plurality of sleds, wherein each sled is pivotally mounted to one of the plurality of arms, and wherein each sled defines a chamber sized to accommodate a sensor, and wherein the bottom surface of the corresponding one of the sleds is contoured in response to a shape of an inspection surface.

Certain further aspects of an example system are described following, any one or more of which may be included in certain embodiments of the example system.

An example system may further include wherein each chamber further includes a stop, and wherein each of the plurality of sensors is positioned against the stop.

An example system may further include wherein each sensor positioned against the stop has a predetermined positional relationship with a bottom surface of the corresponding one of the plurality of sleds.

An example system may further include wherein the inspection surface includes a pipe outer wall, and wherein the bottom surface of the corresponding one of the sleds includes a concave shape.

An example system may further include wherein the bottom surface of the corresponding one of the sleds includes at least one shape selected from the shapes consisting of: a concave shape, a convex shape, and a curved shape.

An example system includes: an inspection robot including: a payload; a plurality of arms, wherein each of the plurality of arms is pivotally mounted to the payload; a plurality of sleds, wherein each sled is pivotally mounted to one of the plurality of arms, thereby configuring a horizontal distribution of the plurality of sleds; a plurality of sensors, wherein each sensor is mounted to a corresponding one of the sleds such that the sensor is operationally couplable to an inspection surface in contact with a bottom surface of the corresponding one of the sleds, wherein the bottom surface of the corresponding one of the sleds is contoured in response to a shape of an inspection surface; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include wherein the horizontal distribution of the plurality of sleds provides for a selected horizontal resolution of the plurality of sensors.

An example system may further include a controller configured to determine the selected horizontal resolution and to configure a position of the plurality of arms on the payload in response to the selected horizontal resolution.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include wherein the inspection surface includes a pipe outer wall, and wherein the bottom surface of the corresponding one of the sleds includes a concave shape.

An example system may further include wherein the bottom surface of the corresponding one of the sleds includes at least one shape selected from the shapes consisting of: a concave shape, a convex shape, and a curved shape.

An example system includes: an inspection robot including: a payload; a plurality of arms, wherein each of the plurality of arms is pivotally mounted to the payload; a plurality of sleds, wherein each sled is pivotally mounted to one of the plurality of arms at a selected one of a plurality of pivot point positions; thereby configuring a horizontal distribution of the plurality of sleds; a plurality of sensors, wherein each sensor is mounted to a corresponding one of the sleds such that the sensor is operationally couplable to an inspection surface in contact with a bottom surface of the corresponding one of the sleds; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include wherein the horizontal distribution of the plurality of sleds provides for a selected horizontal resolution of the plurality of sensors.

An example system may further include a controller configured to determine the selected horizontal resolution and to configure a position of the plurality of arms on the payload in response to the selected horizontal resolution.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system includes: an inspection robot; a plurality of sleds mounted to the inspection robot, wherein each sled is pivotally mounted at a selected one of a plurality of pivot point positions; a plurality of sensors, wherein each sensor is mounted to a corresponding one of the sleds such that the sensor is operationally couplable to an inspection surface in contact with a bottom surface of the corresponding one of the sleds, wherein the bottom surface of the corresponding one of the sleds is contoured in response to a shape of an inspection surface; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include a controller configured to select the one of the plurality of pivot point positions during an inspection run of the inspection robot.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include wherein the inspection surface includes a pipe outer wall, and wherein the bottom surface of the corresponding one of the sleds includes a concave shape.

An example system may further include wherein the bottom surface of the corresponding one of the sleds includes at least one shape selected from the shapes consisting of: a concave shape, a convex shape, and a curved shape.

An example system includes: an inspection robot including: a payload; a plurality of arms, wherein each of the plurality of arms is pivotally mounted to the payload; a plurality of sleds, wherein each sled is pivotally mounted to one of the plurality of arms at a selected one of a plurality of pivot point positions; thereby configuring a horizontal distribution of the plurality of sleds; a plurality of sensors, wherein each sensor is mounted to a corresponding one of the sleds such that the sensor is operationally couplable to an inspection surface in contact with a bottom surface of the corresponding one of the sleds, wherein the bottom surface of the corresponding one of the sleds is contoured in response to a shape of an inspection surface; and a couplant chamber disposed within each of the plurality of sleds, each couplant chamber interposed between a transducer of the sensor mounted to the sled and the inspection surface.

Certain further aspects of an example system are described following, any one or more of which may be included in certain embodiments of the example system.

An example system may further include wherein the horizontal distribution of the plurality of sleds provides for a selected horizontal resolution of the plurality of sensors.

An example system may further include a controller configured to determine the selected horizontal resolution and to configure a position of the plurality of arms on the payload in response to the selected horizontal resolution.

An example system may further include wherein each couplant chamber includes a cone, the cone including a cone tip portion at an inspection surface end of the cone, and a sensor mounting end opposite the cone tip portion, and wherein the cone tip portion defines a couplant exit opening.

An example system may further include wherein the inspection surface includes a pipe outer wall, and wherein the bottom surface of the corresponding one of the sleds includes a concave shape.

An example system may further include wherein the bottom surface of the corresponding one of the sleds includes at least one shape selected from the shapes consisting of: a concave shape, a convex shape, and a curved shape.

The methods and systems described herein may be deployed in part or in whole through a machine having a computer, computing device, processor, circuit, and/or server that executes computer readable instructions, program codes, instructions, and/or includes hardware configured to functionally execute one or more operations of the methods and systems disclosed herein. The terms computer, computing device, processor, circuit, and/or server, as utilized herein, should be understood broadly.

Any one or more of the terms computer, computing device, processor, circuit, and/or server include a computer of any type, capable to access instructions stored in communication thereto such as upon a non-transient computer readable medium, whereupon the computer performs operations of systems or methods described herein upon executing the instructions. In certain embodiments, such instructions themselves comprise a computer, computing device, processor, circuit, and/or server. Additionally or alternatively, a computer, computing device, processor, circuit, and/or server may be a separate hardware device, one or more computing resources distributed across hardware devices, and/or may include such aspects as logical circuits, embedded circuits, sensors, actuators, input and/or output devices, network and/or communication resources, memory resources of any type, processing resources of any type, and/or hardware devices configured to be responsive to determined conditions to functionally execute one or more operations of systems and methods herein.

Network and/or communication resources include, without limitation, local area network, wide area network, wireless, internet, or any other known communication resources and protocols. Example and non-limiting hardware, computers, computing devices, processors, circuits, and/or servers include, without limitation, a general purpose computer, a server, an embedded computer, a mobile device, a virtual machine, and/or an emulated version of one or more of these. Example and non-limiting hardware, computers, computing devices, processors, circuits, and/or servers may be physical, logical, or virtual. A computer, computing device, processor, circuit, and/or server may be: a distributed resource included as an aspect of several devices; and/or included as an interoperable set of resources to perform described functions of the computer, computing device, processor, circuit, and/or server, such that the distributed resources function together to perform the operations of the computer, computing device, processor, circuit, and/or server. In certain embodiments, each computer, computing device, processor, circuit, and/or server may be on separate hardware, and/or one or more hardware devices may include aspects of more than one computer, computing device, processor, circuit, and/or server, for example as separately executable instructions stored on the hardware device, and/or as logically partitioned aspects of a set of executable instructions, with some aspects of the hardware device comprising a part of a first computer, computing device, processor, circuit, and/or server, and some aspects of the hardware device comprising a part of a second computer, computing device, processor, circuit, and/or server.

A computer, computing device, processor, circuit, and/or server may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer readable instructions on a server, client, firewall, gateway, hub, router, or other such computer and/or networking hardware. The computer readable instructions may be associated with a server that may include a file server, print server, domain server, internet server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, and the like. Additionally, this coupling and/or connection may facilitate remote execution of instructions across the network. The networking of some or all of these devices may facilitate parallel processing of program code, instructions, and/or programs at one or more locations without deviating from the scope of the disclosure. In addition, all the devices attached to the server through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods, program code, instructions, and/or programs may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, program code, instructions, and/or programs as described herein and elsewhere may be executed by the client. In addition, other devices utilized for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of methods, program code, instructions, and/or programs across the network. The networking of some or all of these devices may facilitate parallel processing of methods, program code, instructions, and/or programs at one or more locations without deviating from the scope of the disclosure. In addition, all the devices attached to the client through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules, and/or components as known in the art. The computing and/or non-computing device(s) associated with the network infrastructure may include, apart from other components, a storage medium such as flash memory, buffer, stack, RAM, ROM and the like. The methods, program code, instructions, and/or programs described herein and elsewhere may be executed by one or more of the network infrastructural elements.

The methods, program code, instructions, and/or programs described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, program code, instructions, and/or programs described herein and elsewhere may be implemented on or through mobile devices. The mobile devices may include navigation devices, cell phones, mobile phones, mobile personal digital assistants, laptops, palmtops, netbooks, pagers, electronic books readers, music players, and the like. These mobile devices may include, apart from other components, a storage medium such as a flash memory, buffer, RAM, ROM and one or more computing devices. The computing devices associated with mobile devices may be enabled to execute methods, program code, instructions, and/or programs stored thereon. Alternatively, the mobile devices may be configured to execute instructions in collaboration with other devices. The mobile devices may communicate with base stations interfaced with servers and configured to execute methods, program code, instructions, and/or programs. The mobile devices may communicate on a peer to peer network, mesh network, or other communications network. The methods, program code, instructions, and/or programs may be stored on the storage medium associated with the server and executed by a computing device embedded within the server. The base station may include a computing device and a storage medium. The storage device may store methods, program code, instructions, and/or programs executed by the computing devices associated with the base station.

The methods, program code, instructions, and/or programs may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, stand-alone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

Certain operations described herein include interpreting, receiving, and/or determining one or more values, parameters, inputs, data, or other information. Operations including interpreting, receiving, and/or determining any value parameter, input, data, and/or other information include, without limitation: receiving data via a user input; receiving data over a network of any type; reading a data value from a memory location in communication with the receiving device; utilizing a default value as a received data value; estimating, calculating, or deriving a data value based on other information available to the receiving device; and/or updating any of these in response to a later received data value. In certain embodiments, a data value may be received by a first operation, and later updated by a second operation, as part of the receiving a data value. For example, when communications are down, intermittent, or interrupted, a first operation to interpret, receive, and/or determine a data value may be performed, and when communications are restored an updated operation to interpret, receive, and/or determine the data value may be performed.

Certain logical groupings of operations herein, for example methods or procedures of the current disclosure, are provided to illustrate aspects of the present disclosure. Operations described herein are schematically described and/or depicted, and operations may be combined, divided, re-ordered, added, or removed in a manner consistent with the disclosure herein. It is understood that the context of an operational description may require an ordering for one or more operations, and/or an order for one or more operations may be explicitly disclosed, but the order of operations should be understood broadly, where any equivalent grouping of operations to provide an equivalent outcome of operations is specifically contemplated herein. For example, if a value is used in one operational step, the determining of the value may be required before that operational step in certain contexts (e.g. where the time delay of data for an operation to achieve a certain effect is important), but may not be required before that operation step in other contexts (e.g. where usage of the value from a previous execution cycle of the operations would be sufficient for those purposes). Accordingly, in certain embodiments an order of operations and grouping of operations as described is explicitly contemplated herein, and in certain embodiments re-ordering, subdivision, and/or different grouping of operations is explicitly contemplated herein.

The methods and systems described herein may transform physical and/or or intangible items from one state to another. The methods and systems described herein may also transform data representing physical and/or intangible items from one state to another.

The elements described and depicted herein, including in flow charts, block diagrams, and/or operational descriptions, depict and/or describe specific example arrangements of elements for purposes of illustration. However, the depicted and/or described elements, the functions thereof, and/or arrangements of these, may be implemented on machines, such as through computer executable transitory and/or non-transitory media having a processor capable of executing program instructions stored thereon, and/or as logical circuits or hardware arrangements. Example arrangements of programming instructions include at least: monolithic structure of instructions; standalone modules of instructions for elements or portions thereof; and/or as modules of instructions that employ external routines, code, services, and so forth; and/or any combination of these, and all such implementations are contemplated to be within the scope of embodiments of the present disclosure Examples of such machines include, without limitation, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements described and/or depicted herein, and/or any other logical components, may be implemented on a machine capable of executing program instructions. Thus, while the foregoing flow charts, block diagrams, and/or operational descriptions set forth functional aspects of the disclosed systems, any arrangement of program instructions implementing these functional aspects are contemplated herein. Similarly, it will be appreciated that the various steps identified and described above may be varied, and that the order of steps may be adapted to particular applications of the techniques disclosed herein. Additionally, any steps or operations may be divided and/or combined in any manner providing similar functionality to the described operations. All such variations and modifications are contemplated in the present disclosure. The methods and/or processes described above, and steps thereof, may be implemented in hardware, program code, instructions, and/or programs or any combination of hardware and methods, program code, instructions, and/or programs suitable for a particular application. Example hardware includes a dedicated computing device or specific computing device, a particular aspect or component of a specific computing device, and/or an arrangement of hardware components and/or logical circuits to perform one or more of the operations of a method and/or system. The processes may be implemented in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and computer readable instructions, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or computer readable instructions described above. All such permutations and combinations are contemplated in embodiments of the present disclosure.

What is claimed is:

1. A system, comprising:
   an inspection robot having a plurality of input sensors, the plurality of input sensors comprising a first plurality of horizontally distributed ultra-sonic (UT) sensors configured to determine UT data, and a second plurality of horizontally distributed magnetic induction sensors configured to determine electromagnetic (EM) induction data,
   wherein at least a portion of an inspection surface comprises a ferrous substrate having a non-ferrous coating thereupon;
   wherein the UT data and the EM induction data comprise inspection data;
   wherein each of the plurality of horizontally distributed magnetic induction sensors is vertically aligned and forward to a corresponding one of the plurality of horizontally aligned UT sensors; and
   a controller, comprising:
      a position definition circuit structured to determine an inspection robot position of the inspection robot on the inspection surface;
      a data positioning circuit structured to interpret the inspection data, and to correlate the inspection data to the inspection robot position on the inspection surface;
      an EM data circuit structured to interpret the EM induction data, and to determine a substrate distance value in response to the EM induction data;
      a thickness processing circuit structured to determine a thickness value in response to the UT data, wherein the thickness value comprises at least one of a thickness of the ferrous substrate, a total thickness of the ferrous substrate and the non-ferrous coating, or a thickness of the non-ferrous coating; and
      wherein the data positioning circuit is further structured to determine position informed inspection data in response to the correlating of the inspection data with the inspection robot position.

2. The system of claim 1, wherein the thickness processing circuit is further structured to determine the thickness value in response to the substrate distance value.

3. The system of claim 1, further comprising a facility wear circuit structured to access a facility wear model, and to determine a facility wear value for the inspection surface in response to the thickness value.

4. The system of claim 3, wherein the inspection surface comprises a surface at a first facility, and wherein the facility wear model includes data from an offset facility.

5. The system of claim 1, wherein each of the plurality of UT sensors and magnetic induction sensors are positioned on one of a plurality of sleds, and wherein a plurality of the sleds are each positioned on an arm operationally coupled to the inspection robot, and wherein the system further includes a biasing member providing a down force on each of the arms.

6. The system of claim 1, wherein the plurality of input UT sensors and magnetic induction sensors are horizontally distributed relative to the inspection surface at selected horizontal positions, wherein the selected horizontal positions comprise an inspection distance between two horizontally adjacent sensors of the plurality of input UT sensors and magnetic induction sensors that is not greater than a selected horizontal resolution.

7. The system of claim 1, wherein the inspection robot position on the inspection surface comprises an absolute position of the inspection robot.

8. A method, comprising:
  operating an inspection robot having a plurality of horizontally distributed magnetic induction sensors and a plurality of horizontally distributed ultra-sonic (UT) sensors, wherein each of the plurality of horizontally distributed magnetic induction sensors is vertically aligned with a corresponding one of the plurality of horizontally aligned UT sensors;
  wherein operating the inspection robot comprises moving the robot vertically on an inspection surface, the method further comprising, during the moving:
    interrogating the inspection surface with the plurality of horizontally distributed magnetic induction sensors to determine electromagnetic (EM) induction data;
    determining a substrate distance value in response to the EM induction data;
    interrogating the inspection surface with the plurality of UT sensors to determine UT data;
    determining a thickness value in response to the UT data and the substrate distance value, wherein the thickness value comprises at least one of a thickness of a ferrous substrate, a total thickness of the ferrous substrate and a non-ferrous coating, or a thickness of the non-ferrous coating; and
    interrogating a selected location of the inspection surface with the magnetic induction sensors before the interrogating the selected location of the inspection surface with the UT sensors.

9. The method of claim 8, further comprising providing a horizontal distribution of the distributed magnetic induction sensors to provide a selected inspection resolution of the inspection surface.

10. The method of claim 9, further comprising providing a down force to a plurality of sleds of the inspection robot, wherein each of the plurality of horizontally distributed magnetic induction sensors is mounted on one of the plurality of sleds.

11. The method of claim 8, wherein the determining the thickness value comprises diagnosing a determination of the thickness value utilizing the substrate distance value.

12. The method of claim 8, wherein determining the thickness value comprises adjusting UT modes utilized to determine the thickness value in response to the substrate distance value.

13. The method of claim 8, wherein the thickness value comprises a thickness of the ferrous substrate, and the method further comprising determining a wear value in response to the thickness of the ferrous substrate.

14. The method of claim 8, wherein the thickness value comprises a thickness of the non-ferrous coating, and the method further comprising determining a wear value in response to the thickness of the non-ferrous coating.

* * * * *

UNITED STATES PATENT AND TRADEMARK OFFICE
CERTIFICATE OF CORRECTION

PATENT NO. : 10,481,608 B2
APPLICATION NO. : 15/988975
DATED : November 19, 2019
INVENTOR(S) : Loosararian et al.

It is certified that error appears in the above-identified patent and that said Letters Patent is hereby corrected as shown below:

In the Drawings

Sheet 22 of 31, Fig. 35, reference numeral 3208, delete "3208" and insert --3506-- therefor Sheet 26 of 31, Fig. 40, reference numeral 4018 (yes option from 4014), delete "PMV" and insert --SMV-- therefor Sheet 26 of 31, Fig. 40, reference numeral 4018 (no option from 4014), delete "4018" and insert --4011-- therefor In the Specification In Column 6, Line 39, delete "100" and insert --500-- therefor In Column 7, Line 24, delete "3," and insert --3B,-- therefor In Column 23, Line 38, delete "14"

In Column 25, Line 69, delete "502" and insert --500-- therefor

In Column 25, Line 50, delete "502" and insert --500-- therefor

In Column 43, Line 63, delete "3608" and insert --3614-- therefor

In Column 44, Line 66, delete "3602" and insert --3610-- therefor

In Column 49, Line 3, delete "4018" and insert --4011-- therefor

Signed and Sealed this
Third Day of October, 2023

Katherine Kelly Vidal
*Director of the United States Patent and Trademark Office*

In Column 52, Line 37, delete "4410" and insert --4500-- therefor

In Column 52, Line 40, delete "4410" and insert --4500-- therefor